United States Patent [19]

Schmidt et al.

[11] Patent Number: 4,973,685
[45] Date of Patent: Nov. 27, 1990

[54] HETEROANNELLATED PHENYLGLYCINE-β-LACTAM ANTIBIOTICS

[75] Inventors: Gunter Schmidt; Karl G. Metzger, both of Wuppertal; Hans-Joachim Zeiler, Velbert, all of Fed. Rep. of Germany

[73] Assignee: Bayer Aktiengesellschaft, Leverkusen, Fed. Rep. of Germany

[21] Appl. No.: 250,597

[22] Filed: Sep. 28, 1988

[30] Foreign Application Priority Data

Oct. 5, 1987 [DE] Fed. Rep. of Germany ....... 3733626

[51] Int. Cl.$^5$ .......................................... C07D 501/12
[52] U.S. Cl. .................................. 540/227; 540/220
[58] Field of Search ................ 540/227, 222; 514/202, 514/206

[56] References Cited

U.S. PATENT DOCUMENTS

| | | | |
|---|---|---|---|
| 4,539,149 | 9/1985 | Milner | 540/221 |
| 4,734,407 | 3/1988 | Schmidt et al. | 514/196 |
| 4,748,163 | 5/1988 | Schmidt et al. | 540/222 |

Primary Examiner—Mukund J. Shah
Assistant Examiner—C. L. Cseh
Attorney, Agent, or Firm—Sprung Horn Kramer & Woods

[57] ABSTRACT

Heteroannellated penicillins and cephalosporins of the formula

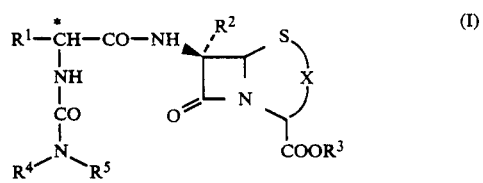

in which $R^1$—stands for a radical of the formula

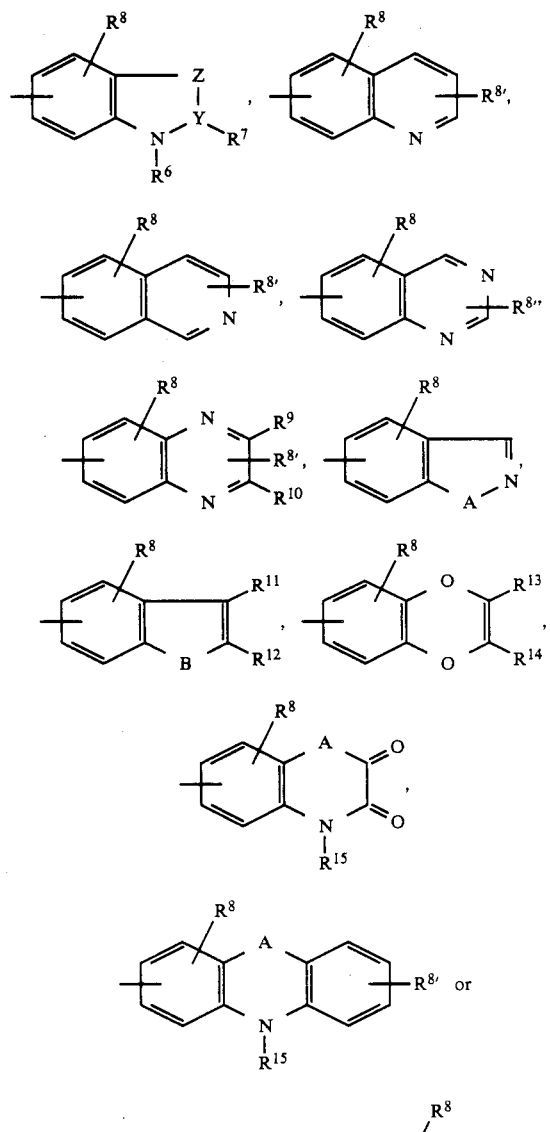

10 Claims, No Drawings

HETEROANNELLATED PHENYLGLYCINE-β-LACTAM ANTIBIOTICS

The invention relates to β-lactam antibiotics which contain heteroannellated phenylglycine derivatives in the side chain, processes for their preparation and their use as medicaments, in particular as antibacterially active agents.

It is known that various representative of 6-acylaminopenicillanic acids and 7-acylaminocephalosporanic acid derivatives possess a very wide spectrum of action, as, for example, piperacillin, [U.S. Pat. No. 4,087,424 (1978)], mezlocillin, [DE No. 2,152,968 (1973)], BRL No. 36,650* [EP No. 71,395 (1982)], cefoperazone (T 1551) [DE No. 2,841,706 (1978); DE No. 2,600,880 (1976)].

(*) Beecham's parenteral Penicillin BRL 36.650

The present invention relates to heteroannellated phenylglycine-β-lactam antibiotics of the general formula (I)

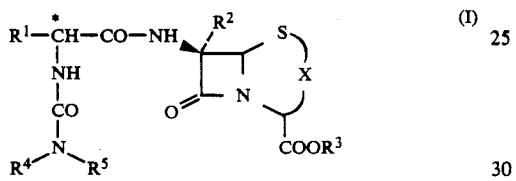

in which $R^1$—stands for a radical of the formula

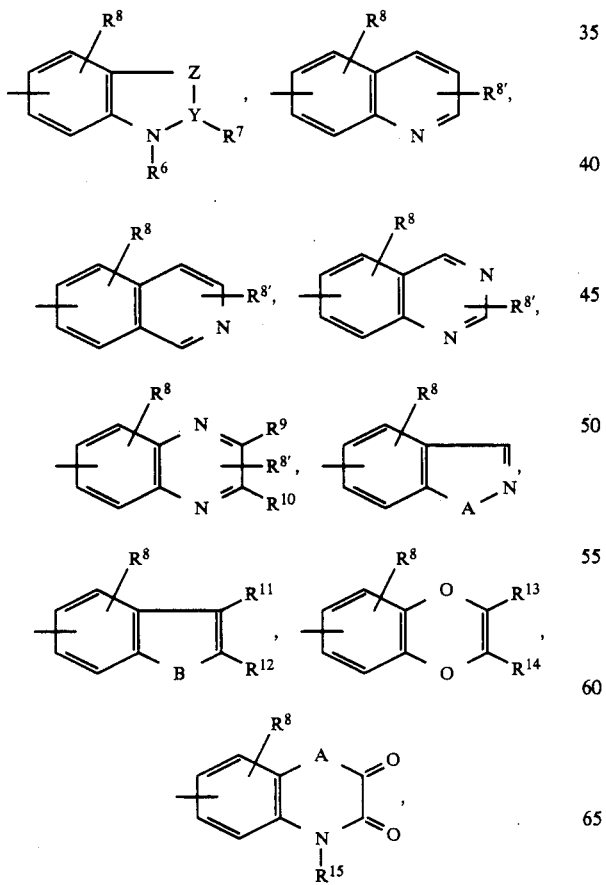

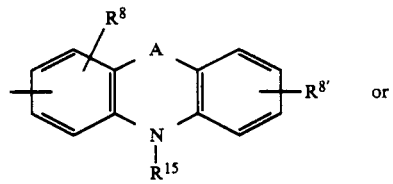

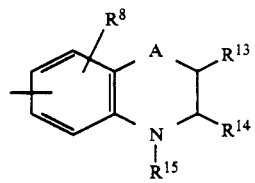

wherein
Y—stands for N or $CR^{16}$, or the grouping
Y—$R^7$—stands for $>$=O or $>$N—$R^7$
Z—stands for O, S or —$NR^{17}$,
A—stands for O, S or —$NR^{18}$,
B—stands for O or —$NR^{15}$,
$R^6$—stands for hydrogen or
  stands for hydroxyl or amino, or
  stands for straight-chain, branched or cyclic alkyl or alkenyl having up to 10 carbon atoms which is optionally substituted by halogen, optionally substituted amino, hydroxyl, cyano or $C_6$–$C_{10}$-aryl, or
  stands for optionally substituted $C_6$–$C_{10}$-aryl,
$R^7$—stands for hydrogen, or
  stands for optionally substituted $C_6$–$C_{10}$-aryl, or
  stands for straight-chain, branched or cyclic alkyl or alkenyl having up to 10 carbon atoms which is optionally substituted by halogen, hydroxyl, alkoxy or alkoxycarbonyl each having up to 6 carbon atoms, cyano, carboxyl, optionally substituted $C_6$–$C_{10}$-aryl, sulpho or by an optionally substituted amino group, or
$R^6$ and $R^7$ together complete a double bond,
$R^8$ and $R^{8'}$ are identical or different and
  stand for hydrogen, or
  stand for straight-chain, branched or cyclic alkyl, alkoxy or alkylthio each having up to 8 carbon atoms, or
  stand for trifluoromethyl or trifluoromethoxy, or
  stand for hydroxyl, mercapto, nitro, cyano or halogen, or
  stand for an optionally substituted amino group,
$R^9$ and $R^{10}$ are identical or different and
  stand for hydrogen, or
  stand for optionally substituted $C_6$–$C_{10}$-aryl, or
  stand for an optionally substituted amino group, or
  stand for hydroxyl, or
  stand for straight-chain, branched or cyclic alkoxy having up to 8 carbon atoms, or
  stand for acyl or acyloxy each having up to 7 carbon atoms, or
  stand for straight-chain, branched or cyclic, optionally substituted alkyl having up to 12 carbon atoms,
$R^{11}$ and $R^{12}$ are identical or different and
  stand for hydrogen, or
  stand for optionally substituted $C_6$–$C_{10}$-aryl, or
  stand for heterocyclyl, or
  stand for hydroxyl, or
  stand for an optionally substituted amino group, or stand for straight-chain, branched or cyclic alkoxy having up to 8 carbon atoms, or stand for acyl or acyloxy each having up to 7 carbon atoms, or stand for alkoxycarbonyl having up to 8 carbon atoms, or stand for optionally substituted straight-chain, branched or cyclic alkyl having up to 12 carbon atoms, or $R^{11}$ and $R^{12}$ together stand for the grouping of the formula

$R^{13}$ and $R^{14}$ are identical or different and
  stand for hydrogen, or
  stand for optionally substituted straight-chain, branched or cyclic alkyl having up to 12 carbon atoms, or
  stand for optionally substituted $C_6$–$C_{10}$-aryl, or
  stand for alkoxycarbonyl having up to 8 carbon atoms,
$R^{15}$ stands for hydrogen, or
  stand for optionally substituted $C_6$–$C_{10}$-aryl, or
  stands for straight-chain, branched or cyclic alkyl having up to 8 carbon atoms,
$R^{16}$ has any of the meanings of $R^7$ and in addition
  stands for halogen, or
  stands for straight-chain, branched or cyclic alkoxy or alkylthio each having up to 8 carbon atoms, or
  stands for an optionally substituted amino group, or
  stands for straight-chain, branched or cyclic alkylsulphonyl having up to 8 carbon atoms, or
  stands for phosphono, sulpho or sulphamoyl, or
  stands for mercapto, hydroxyl, phenylthio or phenoxy, or
  stands for guanidino, amidino, hydrazino or hydroxylamino, or
  stands for optionally substituted heterocyclyl, or
  stands for optionally substituted heterocyclyloxy or heterocyclylthio,
$R^{17}$ has any of meanings of $R^{16}$ but does not complete a double bond with $R^7$, or
$R^{16}$ and $R^{17}$ together stand for a $C_2$–$C_4$-methylene chain which is optionally interrupted by oxygen or sulphur, and
$R^{18}$ has any of the meanings of $R^{15}$ and can be identical or different thereto,
$R^2$—stands for hydrogen, or
  stands for straight-chain, branched or cyclic alkoxy or alkylthio each having up to 5 carbon atoms, or
  stands for an optionally substituted amino group, or
  stands for formamido,
$R^3$—stands for hydrogen, or
  stands for a carboxyl protective group, or
  stands for an ester radical which is cleavable in vivo,
  stands for a group of the formula

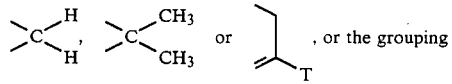

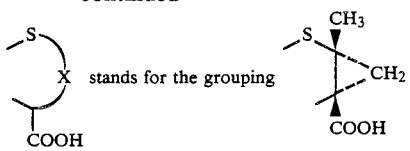

wherein
T—denotes hydrogen or halogen, or
  denotes straight-chain, branched or cyclic alkoxy or alkylthio each having up to 6 carbon atoms, or
  denotes straight-chain, branched or cyclic alkyl, alkenyl or alkinyl each having up to 7 carbon atoms, which can be optionally substituted by halogen, hydroxyl, alkoxy or alkylthio having up to 5 carbon atoms, aminocarbonyloxy, acyloxy having up to 10 carbon atoms, or by a pyridinium radical which can be monosubstituted or polysubstituted, or by a radical of the formula

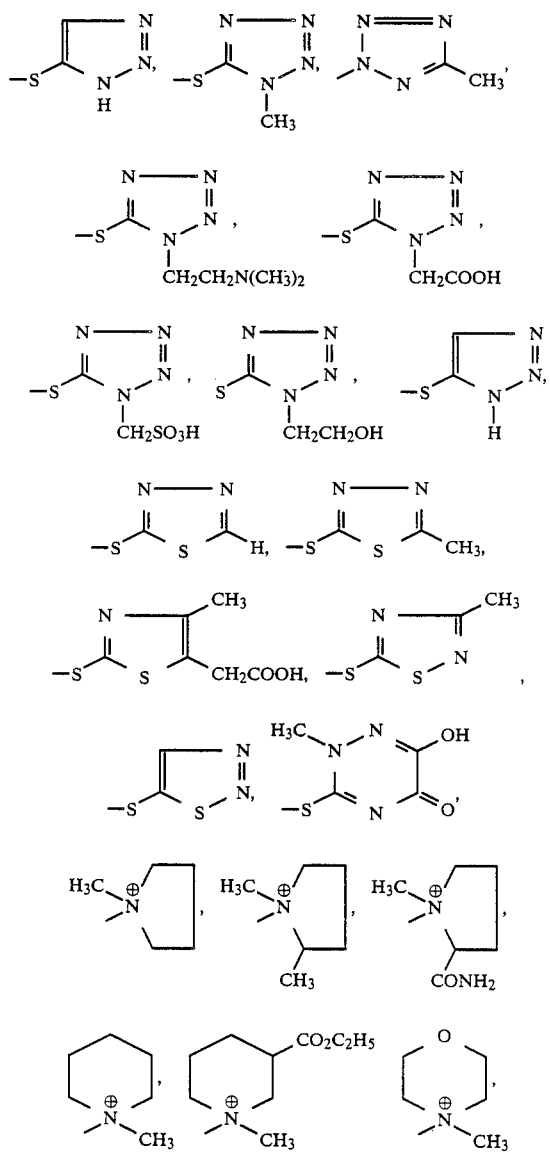

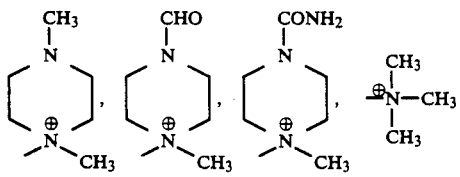

R⁴—stands for hydrogen, or
stands for straight-chain, branched or cyclic alkyl having up to 8 carbon atoms, or
stands for optionally substituted $C_6$–$C_{10}$-aryl, R⁵—stands for hydrogen, or
stands for straight-chain, branched or cyclic alkyl having up to 8 carbon atoms, or
stands for a 5- to 6-membered heterocyclic radical which can contain one or two nitrogen atoms, an oxygen and/or a sulphur atom as hetero atoms and which can be substituted by identical or different, straight-chain, branched or cyclic alkyl, alkenyl or alkinyl each having up to 6 carbon atoms, cycloalkyl having 3 to 7 carbon atoms, alkoxy, alkenyloxy, alkylthio, alkenylthio, alkylsulphonyl or alkenylsulphonyl each having up to 6 carbon atoms, by aryl, aryloxy, arylthio or arylsulphonyl each having 6 to 10 carbon atoms, by an optionally substituted amino group, by oxo, hydroxyl, mercapto, cyano, nitro, by alkylimino having up to 6 carbon atoms or arylimino having 6 to 10 carbon atoms, or R⁴ and R⁵, together with the nitrogen atom, form a ring of the formula

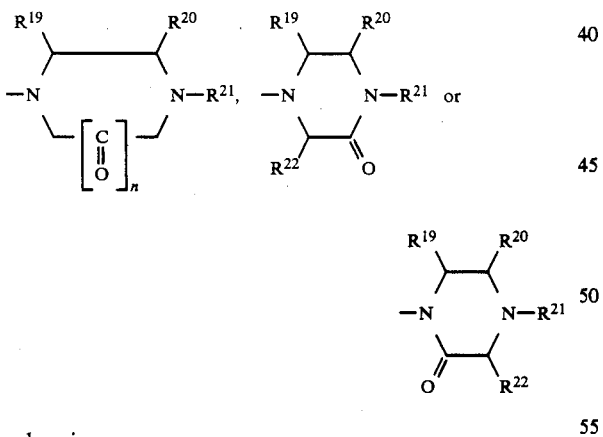

wherein
R¹⁹ and R²⁰ are identical or different and denote hydrogen, straight-chain, branched or cyclic alkyl or alkoxy each having up to 4 carbon atoms, hydroxyl, amino, $C_6$–$C_{10}$-aryl or halogen, or
denote the grouping of the formula

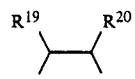

or a grouping of the formula

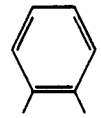

R²¹—denotes hydrogen, or
denotes straight-chain or branched alkyl or alkenyl each having up to 10 carbon atoms, or
denotes cycloalkyl having 3 to 7 carbon atoms, where one or two $CH_2$ groups can be replaced by CO, CS, $CO_2$, O or S in the said radicals, or
denotes optionally substituted $C_6$–$C_{10}$-aryl or $C_7$–$C_{14}$-aralkyl, or
denotes a heterocyclic radical from the series comprising thienyl, furyl, pyridyl, pyrimidyl, oxazolyl, thiazolyl, oxadiazolyl, thiadiazolyl, benzoxazolyl, benzothiazolyl, benzoxadiazolyl, benzothiadiazolyl, quinolyl, isoquinolyl or indolyl, where the said heterocycles may be monosubstituted, disubstituted or trisubstituted by identical or different, straight-chain, branched or cyclic alkyl, alkoxy, alkylthio or alkylsulphonyl each having up to carbon atoms, by trifluoromethyl, trifluoromethoxy, halogen, nitro, cyano, $C_6$–$C_{10}$-aryl or $C_7$–$C_{14}$-aralkyl, or R²¹—denotes a group of the formula

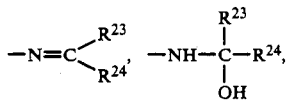

$-SO_2-R^{25}$, $-COR^{25}$ or $-CSR^{25}$,

R²²—denotes hydrogen or straight-chain, branched or cyclic alkyl having up to 6 carbon atoms, R²³ and R²⁴ are identical or different and denote hydrogen, cyano, carboxyl, alkoxycarbonyl having up to 6 carbon atoms, or
denote straight-chain or branched alkyl or alkenyl each having up to 8 carbon atoms, or
denote cycloalkyl having 3 to 7 carbon atoms, or
denote optionally substituted $C_6$–$C_{10}$-aryl or $C_7$–$C_{14}$-aralkyl, or
denote a heterocycle from the series comprising furyl, thienyl, pyridyl, pyrimidyl, oxazolyl, thiazolyl, oxadiazolyl, thiadiazolyl, benzoxazolyl or benzothiazolyl, where the said heterocycles may be monosubstituted, disubstituted or trisubstituted by identical or different, straight-chain, branched or cyclic alkyl, alkoxy or alkylthio each having up to 6 carbon atoms, by halogen, nitro, cyano, trifluoromethyl or trifluoromethoxy, or R²³ and R²⁴, together with the carbon atom, form a 3- to 7-membered heterocyclic ring which can contain up to two nitrogens, an oxygen and/or a sulphur atom as heteroatoms, which can be saturated or unsaturated and fused to benzene, and which can be monosubstituted, disubstituted or trisubstituted by straight-chain or branched alkyl or alkoxy each having up to 8 carbon atoms, by cycloalkyl having 3 to 7 carbon atoms, by halogen, cyano, nitro, trifluoromethyl or trifluoromethoxy, and $R^{25}$—denotes hydroxyl, straight-chain or branched alkyl, alkenyl or alkoxy each having up to 8 carbon atoms, or
denotes cycloalkyl having 3 to 7 carbon atoms, or
denotes optionally substituted $C_6$–$C_{10}$-aryl or $C_7$–$C_{14}$-aralkyl, or
denotes an optionally substituted amino group, or
denotes a heterocyclic ring from the series comprising furyl, thienyl, pyridyl, pyrimidyl, thiazolyl, oxazolyl, thiadiazolyl or oxadiazolyl, where the said heterocyclic radicals can be monosubstituted, disubstituted or trisubstituted by identical or different, straight-chain or branched alkyl, alkoxy or alkylthio each having up to 6 carbon atoms, by halogen, nitro, cyano, trifluoromethyl or trifluoromethoxy,
and their salts.

In the context of the abovementioned definition, aryl or aralkyl in general stands for a phenyl or benzyl radical, where the phenyl radical can be monosubstituted to tetrasubstituted, preferably monosubstituted, disubstituted or trisubstituted, by identical or different substituents. Substituents which may be mentioned are: halogen, preferably fluorine, chlorine or bromine, straight-chain, branched or cyclic alkyl, alkoxy, alkylthio or alkylsulphonyl each having up to 10 carbon atoms, preferably up to 6 carbon atoms, halogenoalkyl, halogenoalkoxy or halogenoalkylthio each having up to 7 carbon atoms, preferably having up to 5 carbon atoms and having up to 5, preferably up to 3 chlorine and/or fluorine atoms, or nitro, cyano, benzyl, sulpho, amidino, sulphamoyl, carbamoyl or an optionally substituted amino group.

Optionally substituted alkyl in the context of the abovementioned definition in general stands for straight-chain, branched or cyclic alkyl preferably having up to 10 carbon atoms, suitable substituents being: halogen, alkoxy or alkylthio each having up to 8 carbon atoms, preferably having up to 6 carbon atoms, halogenoalkylthio or halogenoalkoxy each having up to 8 carbon atoms and up to 5, preferably up to 3 fluorine and/or chlorine atoms, nitro, cyano, an optionally substituted amino group, optionally substituted aryl, sulpho, sulphamoyl, alkylsulphonyl having up to 6 carbon atoms, preferably having up to 4 carbon atoms, hydroxyl, mercapto, acyloxy or acylthio each having up to 7 carbon atoms, carbamoyloxy, carboxyl, alkoxycarbonyl having up to 8 carbon atoms, preferably having up to 6 carbon atoms, phenoxy, phenylthio, benzyloxy or benzylthio.

An optionally substituted amino group in the scope of the abovementioned definition in general stands for a radical of the formula

where
$R^{26}$ and $R^{27}$ are identical or different and stand for hydrogen, or
stand for straight-chain, branched or cyclic alkyl having up to 10 carbon atoms, preferably having up to 6 carbon atoms, or
stand for $C_6$–$C_{10}$-aryl, preferably for phenyl, or
stand for $C_7$–$C_{14}$-aralkyl, preferably $C_7$–$C_{10}$-aralkyl, particularly preferably for benzyl, or
stand for acyl having up to 10 carbon atoms, preferably having up to 8 carbon atoms, particularly preferably for benzoyl or acetyl.

The term heterocyclyl, heterocyclyloxy or heterocyclylthio in the context of the abovementioned meaning stands for saturated or unsaturated heterocycles having up to 3 nitrogen atoms, an oxygen atom and/or a sulphur atom, which are optionally bonded via oxygen or sulphur, preferably for pyrrolyl, pyrrolidinyl, pyrazolyl, imidazolyl, pyridyl, pyridazinyl, pyrimidyl, pyrazinyl, quinolyl, isoquinolyl, indolyl, quinoxalyl, quinazolyl, piperidinyl, morpholinyl, piperazinyl, thiomorpholinyl, furyl, thienyl, oxazolyl, thiazolyl, isoxazolyl, thiadiazolyl, triazolyl or tetrazolyl.

If these heterocycles are substituted, then they are monosubstituted, disubstituted or trisubstituted, preferably monosubstituted or disubstituted, by identical or different, straight-chain or branched alkyl, alkylthio or alkoxy each having up to 4 carbon atoms, preferably having 1 or 2 carbon atoms, halogen, preferably fluorine, chlorine or bromine, nitro, cyano, hydroxyl, amino, trifluoromethyl, trifluoromethoxy or trifluoromethylthio.

Carboxyl protective group in the scope of the abovementioned definition stands for the carboxyl protective groups customary in $\beta$-lactam chemistry. Easily cleavable groups may preferably be mentioned, such as, for example: methyl, ethyl, tert.-butyl, decyl, 2-chloroethyl, 2,2,2-trichloroethyl, cyanoethyl, diphenylmethyl, triphenylmethyl, acetoxymethyl, allyl, benzyl, 4-methoxyphenyl, 4-nitrobenzyl, 2-nitrobenzyl, 4-methoxybenzyl, 2,4-dimethoxybenzyl, trimethylsilylethyl, trimethylsilyl, tert.-butyldimethylsilyl, acetonyl, 1-phenoxyethyl or 2-methyl-2-propenyl.

If $R^3$ stands for an ester radical which is easily cleavable in vivo, then pharmaceutically tolerable ester radicals which are easily hydrolyzed in vivo to free carboxyl groups ($R^3$=H) are meant thereby.

Such ester radicals are well known in the $\beta$-lactam field. In most cases, they improve the absorption properties of the $\beta$-lactam compounds. In addition, the radical $R^3$ should be of such a type that it imparts pharmaceutically acceptable properties to a compound of the formula (I) and on cleavage in vivo releases pharmaceutically acceptable fragments.

Examples of such groups are found in DE-OS (German Published Specification) No. 2,517,316. Preferred ester groups which are cleavable in vivo are those of the following formulae:

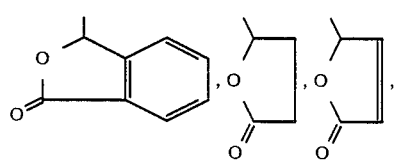

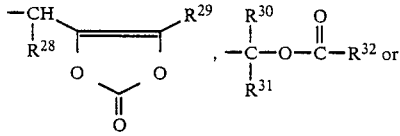

-continued

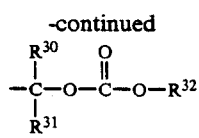

wherein $R^{28}$ and $R^{29}$ are identical or different and stand for hydrogen, phenyl or stand for $C_1$-$C_4$-alkyl, preferably for methyl, $R^{30}$ and $R^{31}$ are identical or different and stand for hydrogen or stand for $C_1$-$C_4$-alkyl, preferably methyl, and $R^{32}$—stands for $C_1$-$C_6$-alkyl, preferably for $C_1$-$C_4$-alkyl.

The compounds of the general formula (I) according to the invention can be present, depending upon the meaning of $R^3$ and T, as free acids, as esters, as internal salts

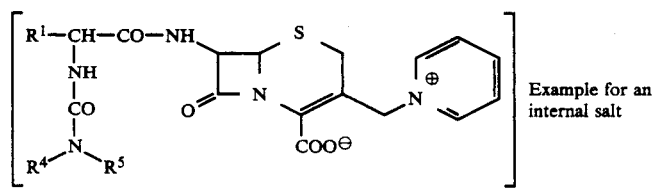

Example for an internal salt or as non-toxic, physiologically acceptable salts having a cation

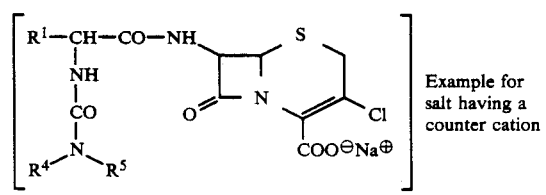

Example for salt having a counter cation or when T is a positively charged radical, as non-toxic, physiologically acceptable salts having a counter anion

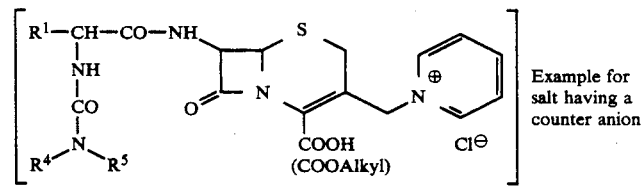

Example for salt having a counter anion

Counter cations which may be mentioned are preferably alkali metal or alkaline earth metal cations such as, for example, sodium ions, potassium ions, magnesium ions or calcium ions, or aluminium ions or ammonium ions, and also non-toxic substituted ammonium ions from amines such as dilower alkylamines, trilower alkylamines, procaine, dibenzylamine, N,N'-dibenzylethylenediamine, N-benzyl-β-phenylethylamine, N-methylmorpholine, 1-ephenamine, dihydroabietylamine, N,N'-bisdihydroabietylethylenediamine, N-lower alkylpiperidine or other amines which can be used for the formation of salts of β-lactam compounds.

Counter anions which may be preferably mentioned are inorganic or organic acid radicals such as, for example, chloride, bromide, iodide, sulphate, hydrogen sulphate, phosphate, hydrogen phosphate, carbonate, hydrogen carbonate, or sulphonates such as methylsulphonate, ethylsulphonate, toluenesulphonate, benzenesulphonate, naphthalene disulphonate, or carboxylates such as acetate, formate, oxalate, tartrate, citrate, maleate, fumarate, benzoate, succinate or lactate.

Because of the presence of the asymmetrical carbon atom designated by * (see formula I), the β-lactam antibiotics of the general formula (I) include the D-, L- and D,L-forms. Both the diastereomer mixtures and also the D-form and the L-form of the compounds according to the invention may be employed for the treatment of bacterial infectious diseases. The D-form of the compounds according to the invention is particularly preferred.

Compounds of the general formula (I) which may be mentioned as preferred are those in which $R^1$—stands for a group of the formula

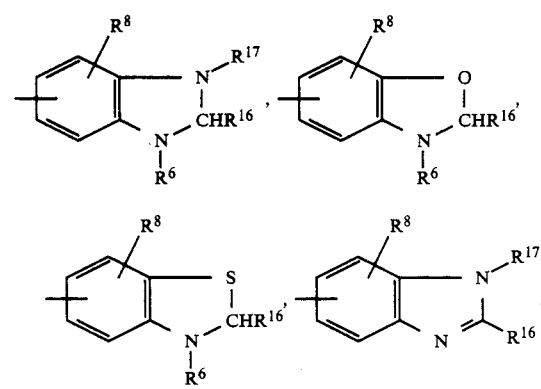

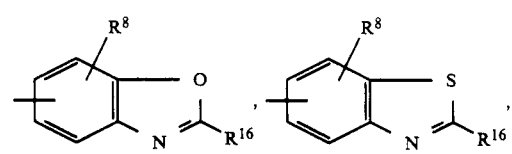

-continued

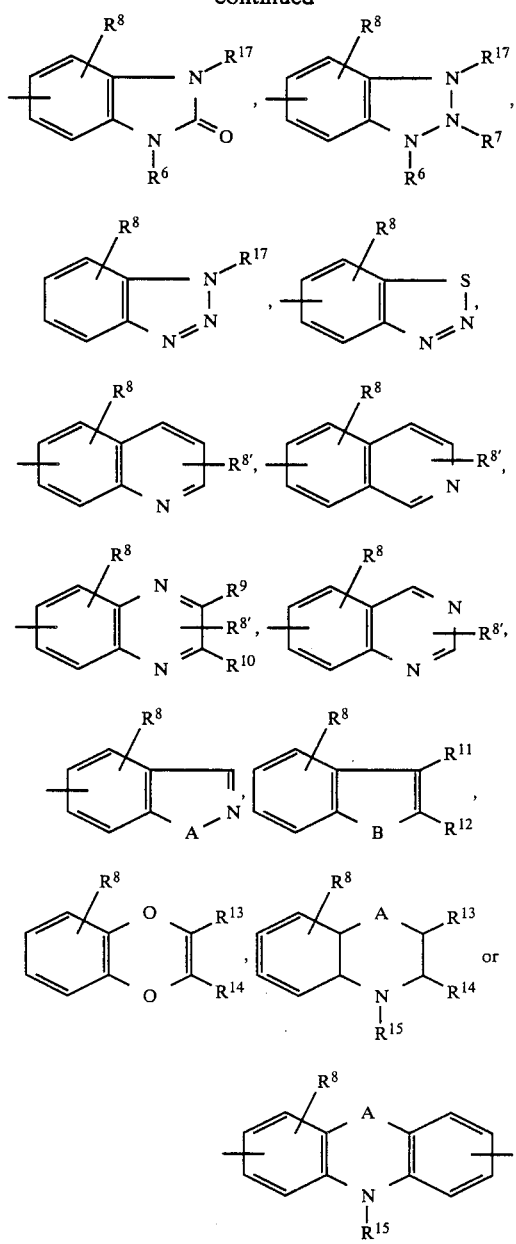

wherein $R^6$—stands for hydrogen, or
stands for hydroxyl or amino, or
stands for straight-chain, branched or cyclic alkyl or alkenyl each having up to 8 carbon atoms, which are optionally substituted by one or more fluorine, chlorine, bromine, optionally substituted amino, hydroxyl or phenyl substituents, or
stands for optionally substituted phenyl, $R^7$—stands for hydrogen, or
stands for optionally substituted phenyl, or
stands for straight-chain, branched or cyclic alkyl or alkenyl each having up to 8 carbon atoms, which is optionally substituted by one or more fluorine, chlorine, bromine, alkoxy having up to 4 carbon atoms, hydroxyl, carboxyl, phenyl, sulpho or an optionally substituted amino group, $R^8$ and $R^{8'}$ are identical or different and stand for hydrogen, or
stand for straight-chain or branched alkyl, alkoxy or alkylthio each having up to 6 carbon atoms, or
stand for trifluoromethyl or trifluoromethoxy, or
stand for hydroxyl, mercapto, nitro, cyano, fluorine, chlorine or bromine, or
stand for an optionally substituted amino group, $R^9$ and $R^{10}$ are identical or different and stand for hydrogen, or
stand for phenyl which is optionally monosubstituted or disubstituted identically or differently by fluorine, chlorine, bromine, alkyl, alkoxy or alkylthio each having up to 4 carbon atoms, halogenoalkyl, halogenoalkoxy or halogenoalkylthio each having up to 3 carbon atoms and having one to three fluorine, by nitro, cyano, amino or dimethylamino, or
stand for an optionally substituted amino group having the abovementioned meaning, or
stand for hydroxyl or alkoxy having up to 6 carbon atoms, or
stand for benzyloxy or alkanoyloxy having up to 4 carbon atoms, or
stand for straight-chain, branched or cyclic alkyl having up to 8 carbon atoms, which is optionally substituted by one or more fluorine, chlorine, bromine, alkoxy or alkylthio each having up to 4 carbon atoms, halogenoalkoxy, halogenoalkylthio each having up to 4 carbon atoms and one to three halogen atoms, by nitro, cyano an optionally substituted amino group having the abovementioned meaning, phenyl, sulpho, sulphamoyl, alkylsulphonyl having up to 2 carbon atoms, hydroxyl, mercapto, benzoyloxy, alkanoyloxy having up to 4 carbon atoms, carbamoyloxy or alkoxycarbonyl having up to 4 carbon atoms, $R^{11}$ and $R^{12}$ are identical or different and
stand for hydrogen, or
stand for phenyl which is optionally monosubstituted or disubstituted identically or differently by fluorine, chlorine, bromine, alkyl, alkoxy or alkylthio each having up to 4 carbon atoms, halogenoalkyl, halogenoalkoxy or halogenoalkylthio each having up 3 carbon atoms and having one to three halogen atoms, by nitro, cyano, dimethylamino or amino, or
stand for hydroxyl, or
stand for pyridyl, thienyl, furyl or pyrimidyl, or
stand for an optionally substituted amino group having the abovementioned meaning, or
stand for straight-chain, branched or cyclic alkoxy having up to 6 carbon atoms, or
stand for benzoyloxy, alkanoyloxy having up to 4 carbon atoms, or
stand for benzoyl or acetyl, or
stand for alkoxycarbonyl having up to 6 carbon atoms, or
stand for straight-chain, branched or cyclic alkyl having up to 8 carbon atoms and optionally substituted one to three times by fluorine, chlorine, bromine, alkoxy or alkylthio each having up to 4 carbon atoms, halogenoalkoxy or halogenoalkylthio each having up to 4 carbon atoms and having one to three halogen atoms, by nitro, cyano, an optionally substituted amino group having the abovementioned meaning, phenyl, sulpho, sulphamoyl, alkylsulphonyl having up to 2 carbon atoms, hydroxyl, mercapto, benzyloxy, alkanoyloxy having up to 4 carbon atoms, carbamoyloxy, alkoxycarbonyl having up to 4 carbon atoms, phenyloxy, phenylthio, benzyloxy or benzylthio, or R$^{11}$ and R$^{12}$ together stand for a grouping of the formula

R$^{13}$ and R$^{14}$ are identical or different and
stand for hydrogen, or
stand for straight-chain, branched or cyclic alkyl having up to 8 carbon atoms, which is optionally substituted once or more by fluorine, chlorine, bromine, alkoxy or alkylthio each having up to 4 carbon atoms, halogenoalkoxy or halogenoalkylthio each having up to 4 carbon atoms and having one to three halogen atoms, by nitro, cyano, an optionally substituted amino group having the abovementioned meaning, phenyl, sulpho, sulphamoyl, alkylsulphonyl having up to 2 carbon atoms, hydroxyl, mercapto, benzoyloxy, alkanoyloxy having up to 4 carbon atoms, carbamoyloxy or alkoxycarbonyl having up to 4 carbon atoms, or
stand for phenyl, which is optionally monosubstituted or disubstituted identically or differently by fluorine, chlorine, bromine, alkyl, alkoxy or alkylthio each having up to 4 carbon atoms, halogenoalkyl, halogenoalkoxy or halogenoalkylthio each having up 3 carbon atoms and one to three halogen atoms, by nitro, cyano, amino or dimethylamino, or
stand for alkoxycarbonyl having up to 6 carbon atoms, A—stands for O, S or —NR$^{18}$,
B—stands for O or —NR$^{15}$,
R$^{15}$—stands for hydrogen, or
stands for phenyl, or
stands for straight-chain, branched or cyclic alkyl having up to 6 carbon atoms,
R$^{16}$ has the same meaning as R$^7$ and in addition
stands for fluorine, chlorine, bromine, or
stands for alkoxy, alkylthio or alkylthio or alkylsulphonyl each having up to 6 carbon atoms, or
stands for an optionally substituted amino group, or
stands for phosphono, sulpho, sulphamoyl, hydroxyl, mercapto, phenylthio or phenoxy, or
stands for guanidino, hydrazino or hydroxylamino, or
stands for optionally substituted heterocyclyl, heterocyclyloxy or heterocyclylthio,
R$^{17}$ has the same meaning as R$^{16}$, but does not complete a double bond with R$^7$, or
R$^{16}$ and R$^{17}$ together stand for a C$_2$-C$_4$-methylene chain which is optionally interrupted by sulphur, and
R$^{18}$ has the same meaning as R$^{15}$ and can be identical or different to this,
R$^2$—stands for hydrogen, or
stands for methoxy or methylthio, or stands for amino, alkylamino or dialkylamino each having up to 3 carbon atoms per alkyl group, phenylamino, benzylamino or acetamido, or
stands for formamidino,
R$^3$—stands for hydrogen, or
stands for methyl, ethyl, tert.-butyl, 2-chloroethyl, 2,2,2-trichloroethyl, cyanoethyl, diphenylmethyl, triphenylmethyl, acetoxymethyl, allyl, benzyl, 4-methoxy-benzyl, 2,4-dimethoxybenzyl, 1-phenoxyethyl, 2-methyl-2-propenyl, 4-nitrobenzyl, 2-nitrobenzyl, trimethylsilylethyl or tert.-butyldimethylsilylethyl, or
stands for a radical of the formula

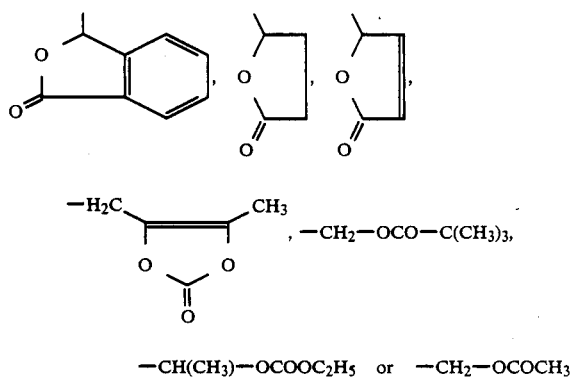

—CH(CH$_3$)—OCOOC$_2$H$_5$ or —CH$_2$—OCOCH$_3$

X—stands for a group of the formula

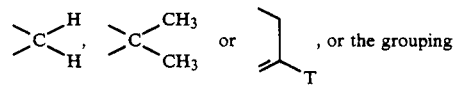

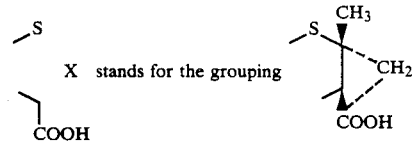

wherein
T—denotes hydrogen or fluorine, chlorine or bromine, or
denotes straight-chain, branched or cyclic alkoxy or alkylthio each having up to 3 carbon atoms, or
denotes straight-chain or branched alkyl or alkenyl each having up to 5 carbon atoms, which is optionally substituted once or more by fluorine, chlorine, bromine, alkoxy or alkylthio each having up to 3 carbon atoms, aminocarbonyloxy, acetyloxy, benzoyloxy of by a radical of the formula

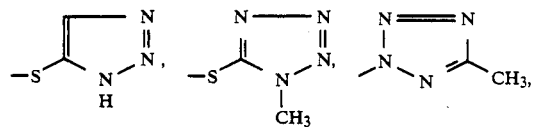

-continued

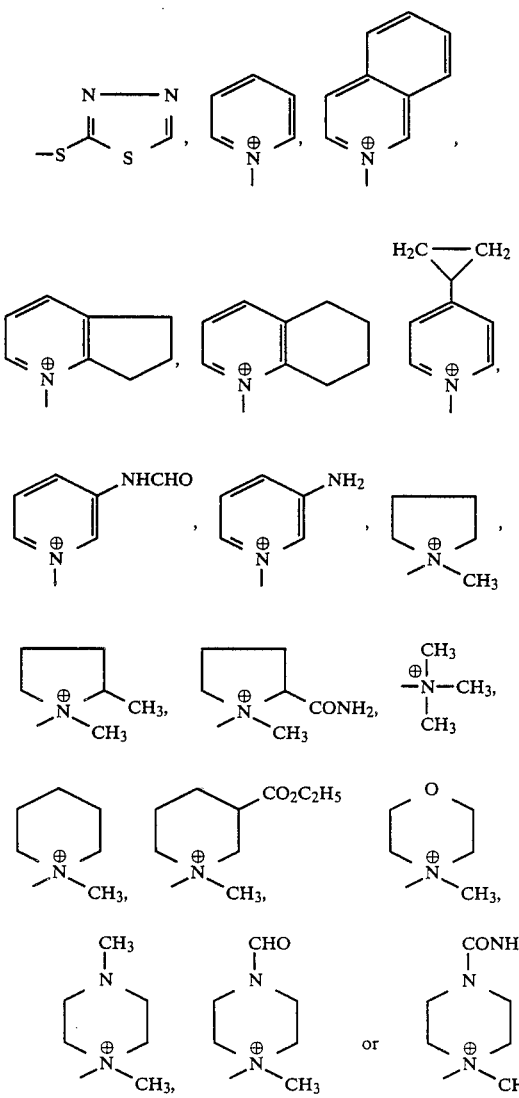

R[4]—stands for hydrogen, or
stands for straight-chain or branched alkyl having up to 4 carbon atoms, or
R[5]—stands for hydrogen, or
stands for straight-chain or branched up to 4 carbon atoms, or alkyl having
stands for a 5- to 6-membered heterocyclic ring which can contain a nitrogen, oxygen or sulphur atom as heteroatoms and which can be monosubstituted or disubstituted by identical or different alkyl or alkenyl having up to 4 carbon atoms, by cyclopropyl, cyclopentyl or cyclohexyl, by alkoxy, alkenyloxy, alkylsulphonyl or alkenylsulphonyl each having up to 4 carbon atoms, phenyl, phenyloxy, phenylsulphonyl or by amino, alkylamino or dialkylamino each having up to 3 carbon atoms per alkyl group, by oxo, alkylimino having up to 3 carbon atoms or phenylimino, or
R[4] and R[5], together with the nitrogen atom, form a ring of the formula

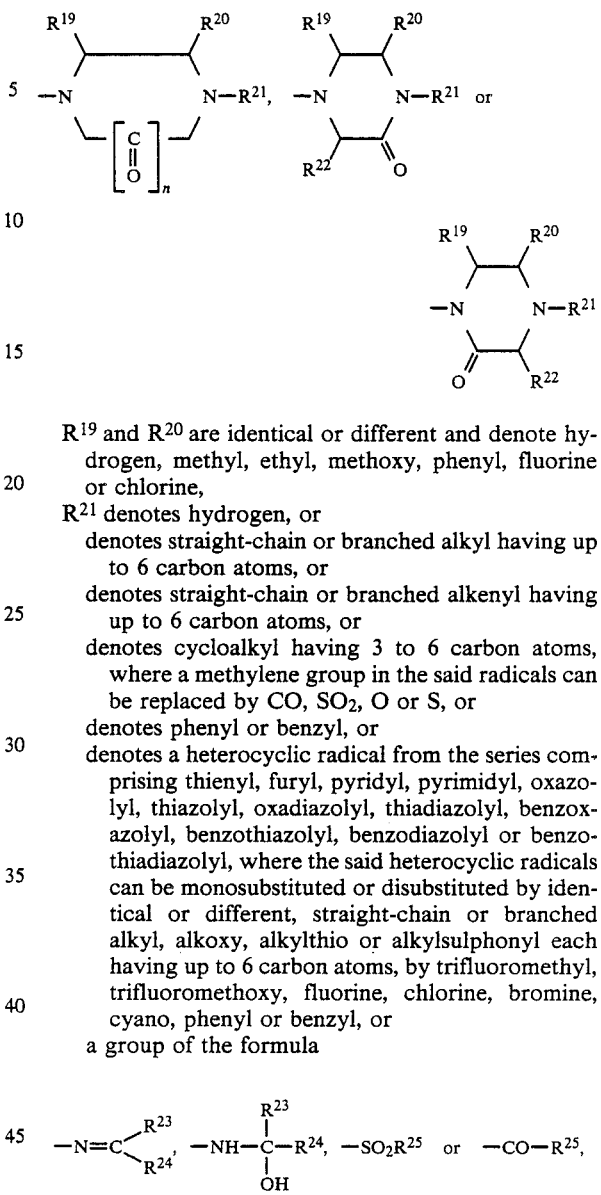

R[19] and R[20] are identical or different and denote hydrogen, methyl, ethyl, methoxy, phenyl, fluorine or chlorine,
R[21] denotes hydrogen, or
denotes straight-chain or branched alkyl having up to 6 carbon atoms, or
denotes straight-chain or branched alkenyl having up to 6 carbon atoms, or
denotes cycloalkyl having 3 to 6 carbon atoms, where a methylene group in the said radicals can be replaced by CO, SO$_2$, O or S, or
denotes phenyl or benzyl, or
denotes a heterocyclic radical from the series comprising thienyl, furyl, pyridyl, pyrimidyl, oxazolyl, thiazolyl, oxadiazolyl, thiadiazolyl, benzoxazolyl, benzothiazolyl, benzodiazolyl or benzothiadiazolyl, where the said heterocyclic radicals can be monosubstituted or disubstituted by identical or different, straight-chain or branched alkyl, alkoxy, alkylthio or alkylsulphonyl each having up to 6 carbon atoms, by trifluoromethyl, trifluoromethoxy, fluorine, chlorine, bromine, cyano, phenyl or benzyl, or
a group of the formula $$-N=C{\overset{R^{23}}{\underset{R^{24}}{\diagdown}}}, \quad -NH-\underset{\underset{OH}{|}}{\overset{\overset{R^{23}}{|}}{C}}-R^{24}, \quad -SO_2R^{25} \quad \text{or} \quad -CO-R^{25},$$

wherein
R[22]—denotes hydrogen, or straight-chain or branched alkyl having up to 4 carbon atoms,
R[23] and R[24] are identical or different and denote hydrogen, or
denote alkoxycarbonyl having up to 4 carbon atoms, or
denote straight-chain or branched alkyl or alkenyl having up to 6 carbon atoms, or
denote cycloalkyl having 3 to 6 carbon atoms, or
denote phenyl or benzyl, or
denote a heterocyclic radical from the series comprising furyl, pyridyl, pyrimidyl, thienyl, oxazolyl or thiazolyl, which can optionally be monosubstituted or disubstituted by identical or different alkyl or alkoxy each having up to 4 carbon atoms, fluorine, chlorine, bromine, nitro, cyano, trifluoromethyl or trifluoromethoxy, or
R[23] and R[24], together with the carbon atom, form a 5- or 6-membered heterocyclic ring which can contain up to two nitrogen atoms, one oxygen atom and/or one sulphur atom as heteroatoms, which can be saturated or unsaturated and which can be monosubstituted or disubstituted by identical or different alkyl or alkoxy having up to 6 carbon atoms, cyclopropyl, cyclopentyl or cyclohexyl, or by fluorine, chlorine, bromine, cyano, nitro, trifluoromethyl or trifluoromethoxy, $R^{25}$ stands for hydroxyl or alkoxy having up to 4 carbon atoms, or stands for alkyl or alkenyl having up to 6 carbon atoms, stands for cycloalkyl having 3 to 6 carbon atoms, or stands for optionally substituted phenyl or benzyl, or stands for optionally substituted amino, or stands for a heterocyclic radical from the series comprising furyl, pyridyl, pyrimidyl, thiazolyl, oxazolyl, thiadiazolyl or oxadiazolyl, where the said heterocycles can be monosubstituted or disubstituted by identical or different alkyl or alkoxy having up to 4 carbon atoms, fluorine, chlorine, bromine, nitro, cyano, trifluoromethyl or trifluoromethoxy, and their salts.

Compounds of the general formula (I) which may be mentioned as particularly preferred are those in which $R^1$—stands for a group of the formula

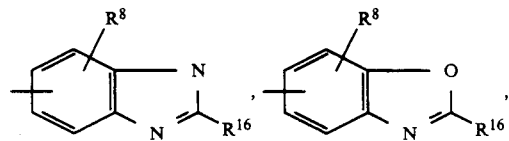

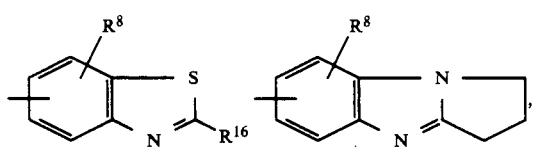

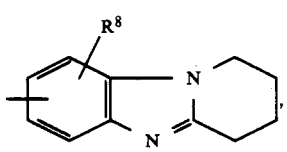

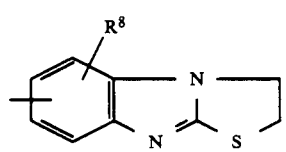

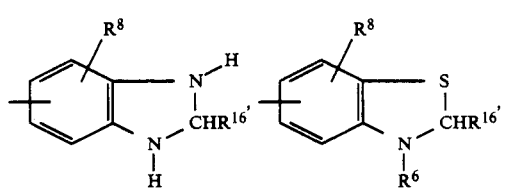

-continued

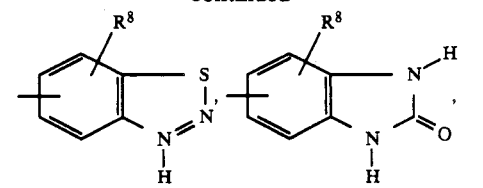

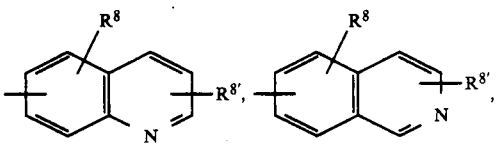

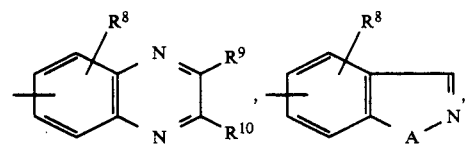

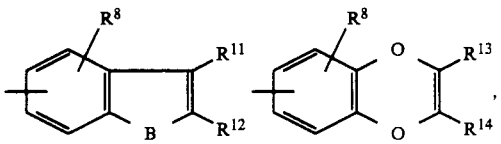

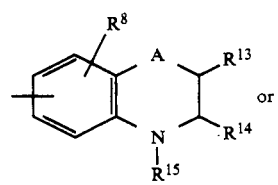

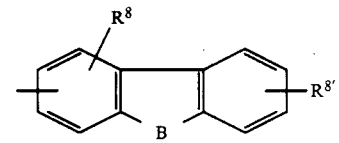

wherein $R^6$—stands for hydrogen, or stands for straight-chain, branched or cyclic alkyl or alkenyl having up to 6 carbon atoms, which is optionally substituted by fluorine, amino, hydroxyl or phenyl, or stands for optionally substituted phenyl, $R^8$ and $R^{8'}$ are identical or different and stand for hydrogen, or stand for straight-chain or branched alkyl, alkoxy or alkylthio each having up to 4 carbon atoms, or stand for trifluoromethyl or trifluoromethoxy, or stand for hydroxyl, nitro, cyano, fluorine or chlorine, or stand for amino, methylamino, dimethylamino, phenylamino or acetamido, $R^9$ and $R^{10}$ are identical or different and stand for hydrogen or, stand for phenyl which is optionally substituted by chlorine, fluorine, alkyl having up to 4 carbon atoms, methoxy, methylthio, trifluoromethyl, trifluoromethoxy, trifluoromethylthio, nitro, cyano, amino or dimethylamino, or stand for amino, methylamino, dimethylamino, phenylamino or acetamido, or stand for hydroxyl, or stand for alkoxy having up to 4 carbon atoms, or
stand for benzoyloxy or acetoxy, or
stand for straight-chain, branched or cyclic alkyl or alkenyl each having up to 6 carbon atoms, which can be substituted by fluorine, chlorine, methoxy, methylthio, trifluoromethoxy or cyano, $R^{11}$ and $R^{12}$ are identical or different and
stand for hydrogen, or
stand for phenyl which is optionally substituted by fluorine, chlorine, alkyl having up to 4 carbon atoms, methoxy, methylthio, trifluoromethyl, trifluoromethoxy, trifluoromethylthio, nitro, cyano, amino or dimethylamino, or
stand for pyridyl, thienyl, furyl, pyrimidyl or hydroxyl, or
stand for amino, methylamino, dimethylamino, phenylamino or acetamido, or
stand for alkoxy having up to 4 carbon atoms, or
stand for benzoyloxy or acetoxy, or
stand for benzoyl or acetyl, or
stand for alkoxycarbonyl having up to 4 carbon atoms, or
stand for straight-chain, branched or cyclic alkyl or alkenyl having up to 6 carbon atoms, which is optionally substituted by fluorine, chlorine, methoxy, methylthio, trifluoromethoxy, cyano, phenyloxy or benzyloxy, $R^{13}$ and $R^{14}$ are identical or different and
stand for hydrogen, or
stand for straight-chain, branched or cyclic alkyl or alkenyl having up to 6 carbon atoms, which is optionally substituted by fluorine, chlorine, methoxy, methylthio, trifluoromethoxy or cyano, or
stand for phenyl which is optionally substituted by fluorine, chlorine, alkyl having up to 4 carbon atoms, methoxy, methylthio, trifluoromethyl, trifluoromethoxy, trifluoromethylthio, nitro, cyano, amino or dimethylamino, or
stand for alkoxycarbonyl having up to 4 carbon atoms, stands for O, S or $-NR^{18}$,
stands for O or $-NR^{15}$,
stands for hydrogen, or
stands for phenyl, or
stands for straight-chain or branched alkyl having up to 4 carbon atoms, $R^{16}$ stands for hydrogen, or
stands for straight-chain or branched alkyl or alkenyl each having up to 4 carbon atoms, which is optionally substituted by fluorine, chlorine, alkoxy having up to 4 carbon atoms, hydroxyl, carboxyl, phenyl, sulpho, amino, alkylamino or dialkylamino each having up to 3 carbon atoms per alkyl group, phenylamino, benzylamino or by acetamido, or
stands for fluorine, chlorine or bromine, or
stands for alkoxy or alkylthio each having up to 4 carbon atoms, or
stands for phenyl, or
stands for amino, alkylamino or dialkylamino each having up to 3 carbon atoms per alkyl group, phenylamino, benzylamino or acetamido, or
stands for alkylsulphonyl having up to 4 carbon atoms, or
stands for sulpho or sulphamoyl, or
stands for hydroxyl, mercapto, phenyloxy or phenylthio, or stands for guanidino, hydrazino or hydroxylamino, or
stands for pyrrolyl, pyrrolidinyl, pyrazolyl, imidazolyl, pyridyl, quinolyl, isoquinolyl, furyl, thienyl, morpholinyl, piperidinyl, piperazinyl, or pyrimidyl, each of which can be substituted by fluorine, chlorine, methyl, nitro, cyano, hydroxyl, trifluoromethyl, methoxy or amino, or
stands for pyridylthio or pyridyloxy, $R^{17}$—has the same meaning as $R^{16}$ and can be identical or different to $R^{16}$, and $R^{18}$—has the same meaning as $R^{15}$ and is identical or different to $R^{15}$, $R^2$—stands for hydrogen, or
stands for methoxy or methylthio, or
stands for amino, methylamino, dimethylamino, phenylamino, benzylamino or acetamido, or
stands for formamidino, $R^3$—stands for hydrogen, or
stands for methyl, ethyl, tert.-butyl, 2,2,2-trichloroethyl, allyl, acetoxymethyl, 4-nitrobenzyl, 2-nitrobenzyl, 4-methoxybenzyl, benzyl or trimethylsilylethyl, or
stands for a radical of the formula

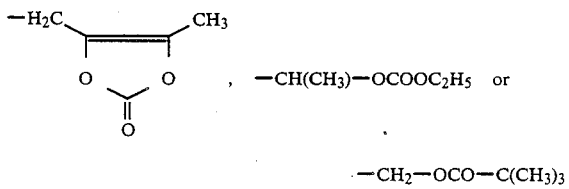

X—stands for a group of the formula

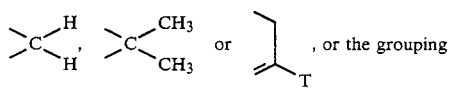

, or the grouping

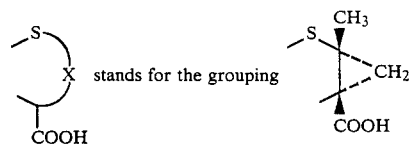

X stands for the grouping wherein
T—denotes hydrogen, chlorine, fluorine, methyl, methoxy, methylthio, trifluoromethyl, methoxymethyl, vinyl, carbamoyloxymethyl or acetoxymethyl, or
denotes a group of the formula

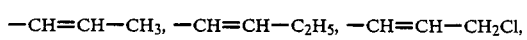

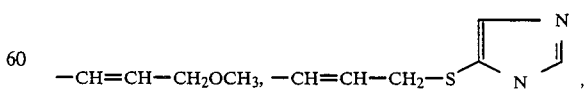

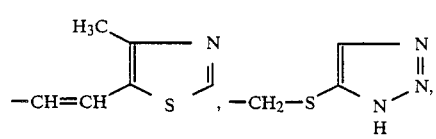

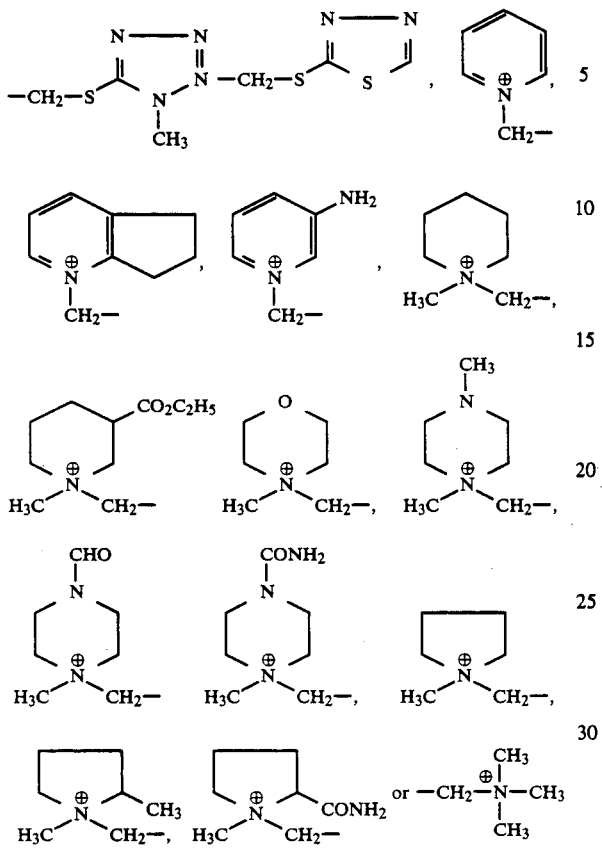

and $R^4$ and $R^5$, together with the nitrogen atoms, form a ring of the formula

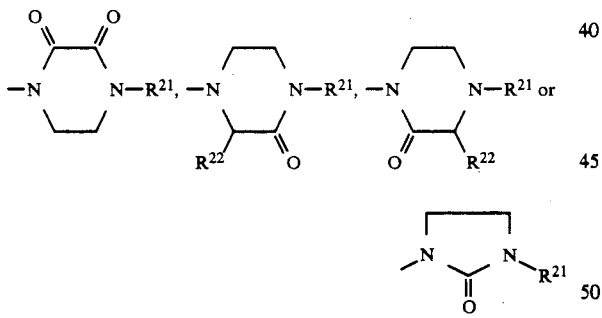

wherein $R^{21}$ denotes hydrogen or alkyl having up to 4 carbon atoms, or
denotes cyclopropyl, cyclopentyl or cyclohexyl, or
denotes phenyl, or
denotes a heterocyclic radical from the series comprising furyl, pyridyl, pyrimidyl, thiazolyl, benzothiazolyl, thiadiazolyl or benzothiadiazolyl, where the said heterocycles can be substituted by straight-chain or branched alkyl, alkenyl, alkoxy, alkylthio or alkylsulphonyl each having up to 4 carbon atoms, by trifluoromethyl, fluorine or chlorine, or
denotes a group of the formula

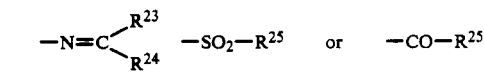

$R^{22}$ denotes hydrogen or methyl, $R^{23}$ and $R^{24}$ are identical or different and denote hydrogen, or
denote straight-chain or branched alkyl or alkenyl each having up to 4 carbon atoms, or
denote cyclopropyl, cyclopentyl or cyclohexyl, or
denote phenyl or benzyl, or
denote a heterocyclic ring from the series comprising furyl, pyridyl or pyrimidyl, $R^{23}$ and $R^{24}$, together with the carbon atom, form a ring from the series comprising furyl, pyridyl, pyrimidyl, oxazolyl, thiazolyl, oxadiazolyl or thiadiazolyl, and $R^{25}$—denotes methoxy or ethoxy, or
denotes straight-chain or branched alkyl or alkenyl each having up to 4 carbon atoms, or
denotes cyclopropyl, cyclopentyl or cyclohexyl, or
denotes phenyl or benzyl, or
denotes amino, alkylamino or dialkylamino each having up to 3 carbon atoms per alkyl group, or
denotes a heterocyclic ring from the series comprising furyl, pyridyl, pyrimidyl or quinolyl, where the heterocyclic rings can be substituted by methyl, ethyl, propyl, isopropyl, methoxy, fluorine, chlorine or trifluoromethyl,
and their salts.

Moreover, a process for the preparation of the heteroannelliertephenylglycine-β-lactam antibiotics of the general formula (I) according to the invention has been found, which is characterized in that carboxylic acids of the general formula (II)

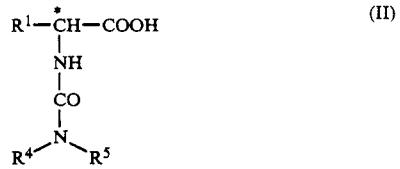

in which $R^1$, $R^4$ and $R^5$ have the abovementioned meaning, are reacted, after activation of the carboxyl group by conversion into a mixed anhydride, for example using ethyl chloroformate or isobutyl chloroformate or methanesulphonyl chloride, or by converting into the acid halide, or by converting into an activated ester, for example using diyl carbodiimide (DCC), if appropriate in the presence of N-hydroxybenzotriazole, with the β-lactamamines of the general formula (III)

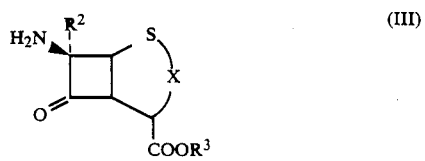

in which $R^2$, $R^3$ and X have the abovementioned meaning, then if appropriate cleaving off protective groups and preparing the desired salts or the free acids from the salts.

The process according to the invention can be illustrated by the following equation:

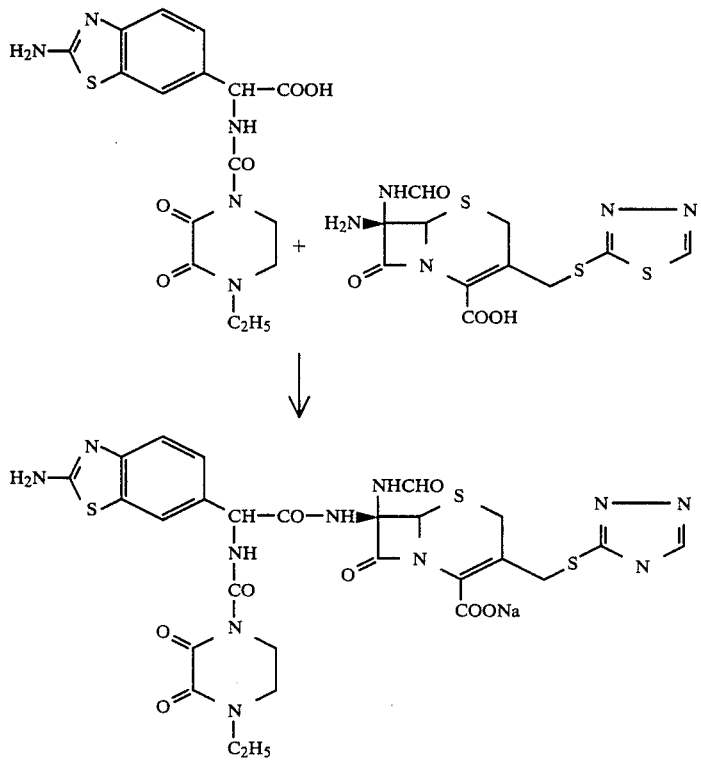

When carrying out the process, it has proved advantageous to activate the carboxylic acid and then to couple it with the β-lactamamines which are brought into solution as salts with amine. The activation with sulphonic acid derivatives of the general formula (IV) or with chloroformic acid esters, preferably ethyl chloroformate, to give anhydrides of the general formula (Va, b), as illustrated in the following equation, is particularly advantageous.

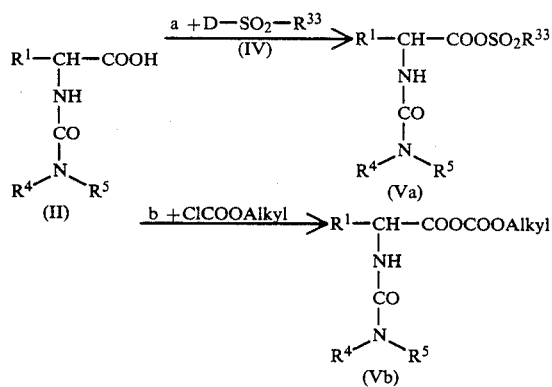

In this connection, in the formula (IV) or (Va)
D—stands for the radical $R^{33}$—$SO_2$—O— or halogen and
$R^{33}$—stands for alkyl having up to 10 carbon atoms which is optionally substituted by fluorine, chlorine, cyano, phenyl, alkoxycarbonyl or alkoxy each having up to 4 carbon atoms, or
stands for phenyl which is optionally substituted by fluorine, chlorine, bromine, cyano, alkyl, alkoxy, alkylthio, alkoxycarbonyl or alkylcarbonyl each having up to 4 carbon atoms, nitro, trifluoromethyl or phenyl.

When $R^{33}$ is substituted, preferably one to three substituents, particularly preferably the abovementioned substituents, are present.

Very particularly preferably, $R^{33}$ represents a methyl or p-tolyl radical.

The mixed anhydrides of the general formula (Va, b) are prepared by dissolving the carboxylic acids of the general formula (II) and 1 to 1.4 equivalents of an amine in a solvent and allowing to react with 1 to 1.2 equivalents of a sulphonic acid derivative of the formula (IV) or a chloroformic acid ester.

Suitable solvents are all solvents which are not changed under the reaction conditions. These preferably include ethers such as, for example, diethyl ether, dioxane or tetrahydrofuran, or chlorinated hydrocarbons such as methylene chloride, chloroform or carbon tetrachloride, or amides such as dimethylformamide or hexamethylphosphoric triamide, or acetonitrile, or acetone. Likewise, it is possible to employ mixtures of the said solvents.

Suitable amines are tertiary amines such as, for example, triethylamine, ethyldiisopropylamine or tributylamine, but also sterically hindered secondary amines such as, for example, diisopropylamine. Likewise, mixtures of the said amines can be employed.

The reaction can be carried out at temperatures between −80° C. and room temperature. The activation is advantageously carried out using methanesulphonyl chloride
in dimethylformamide at −40° C. to −60° C. during the course of 0.2 to 24 hours, preferably 0.25 to 5 hours.

For dissolving the β-lactamamines of the general formula (III), the solvents mentioned in the preparation of the compound of the formula (V) or water, and also the amines mentioned there as bases, can also be used.

Activation of the carboxylic acid of the general formula (II) by converting into an activated ester with, for example, dicyclohexyl carbodiimide, if appropriate in the presence of N-hydroxysuccinimide or 1-hydroxybenzotriazole, is particularly advantageous.

Suitable solvents in this connection are all solvents which are also suitable for the preparation of anhydrides of the general formula (V) and which are already shown therein. The reactions can be carried out at temperatures between −30° C. and +100° C. The mixture is advantageously activated using 1-hydroxybenzotriazole and dicyclohexylcarbodiimide in dimethylformamide at room temperature for 2 to 6 hours. The product is then filtered off with suction from precipitated dicyclohexylurea and reacted during the course of 2 to 24 hours with the β-lactamamine of the general formula (III) in the form of a solution of its amine salts. For dissolving the β-lactamamines of the general formula (III), the solvents mentioned in the preparation of the compound of the formula (V) can be used and also the amines mentioned therein can be used as bases.

The carboxylic acids of the general formula (II) employed as starting compounds are known or can be prepared by known methods [German Offenlegungsschrift No. 3,509,618; German Offenlegungsschrift No. 3,508,258].

The β-lactamamines of the general formula (III) employed as starting materials are known or can be prepared by known methods [U.S. Pat. No. 3,925,372; German Offenlegungsschrift No. 2,606,196; U.S. Pat. No. 3,994,884; British Pat. No. 1,546,622 ; P. H. Miltner et al., J. Chem. Soc. Chem. Commun. 1984, 1335; German Offenlegungsschrift No. 3,509,618; German Offenlegungsschrift No. 3,508,258].

Moreover, the compounds of the general formula (I) can be prepared according to a further process variation by reacting compounds of the general formula (VI)

in which

R$^4$ and R$^5$ have the abovementioned meaning, and

W—stands for halogen, azide or a nucleofugic leaving group, in the presence of a solvent and, if appropriate, an acid-binding agent at temperatures of about −20° C. to about +50° C. with compounds of the general formula (VII)

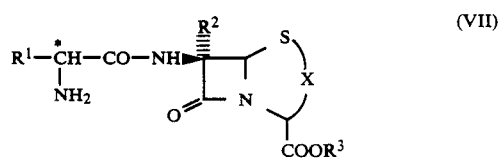

in which

R$^1$, R$^2$, R$^3$ and X have the abovementioned meaning, if desired, converting the β-lactam antibiotics obtained into their non-toxic pharmaceutically acceptable salts after cleaving off protective groups, or preparing the free acids from the optionally obtained salts.

The process variation according to the invention can be illustrated by the following equation:

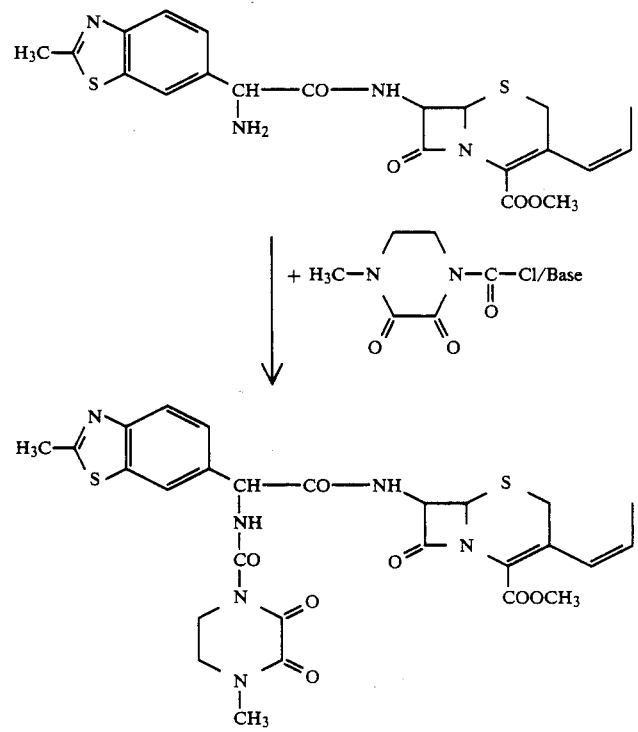

If W stands for halogen, it preferably stands for chlorine or bromine, particularly preferably for chlorine.

Nucleofugic leaving groups in the definition of W are taken to mean all nucleofugic groups customarily used in organic chemistry and primarily those which are described in Angewandten Chemie 81, 543 (1969).

The compounds of the general formula (VII) employed as starting materials are known or can be prepared by known methods [German Offenlegungsschrift No. 3,509,618; German Offenlegungsschrift No. 3,508,258].

The compounds of the general formula (VI) employed as starting materials are known or can be prepared by known methods [German Offenlegungsschrift No. 2,512,998, U.S. Pat. No. 4,087,424].

The following compounds may be mentioned in addition to the experimental examples as new active compounds according to the invention from the penicillin series:

TABLE 1

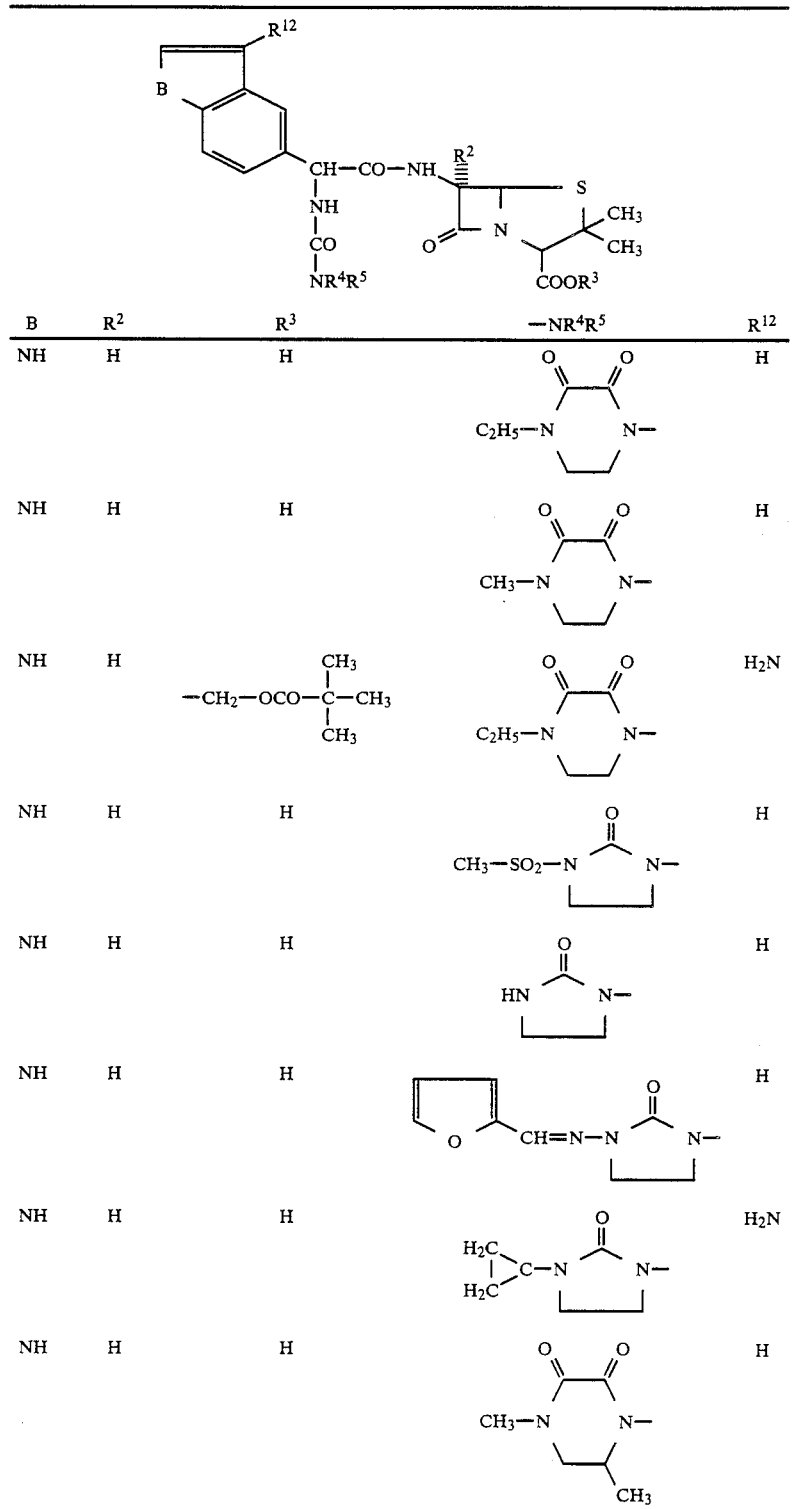

TABLE 1-continued

[Structure: substituted phenyl-CH(NHCONR⁴R⁵)-CO-NH-C(R²)-β-lactam-thiazolidine-COOR³ with R¹² and B substituents on the aromatic ring with vinyl group]

| B | R² | R³ | —NR⁴R⁵ | R¹² |
|---|---|---|---|---|
| O | NH—CHO | H | 1-ethyl-2,3-dioxopiperazin-4-yl (C₂H₅—N ring with two C=O and N—) | H |
| O | NH—CHO | H | 1-methyl-2,3-dioxopiperazin-4-yl (CH₃—N ring) | H |
| O | NH—CHO | —CH₂—OCO—C(CH₃)₃ | 1-ethyl-2,3-dioxopiperazin-4-yl | H₂N |
| O | NH—CHO | H | 3-methylsulfonyl-2-oxoimidazolidin-1-yl (CH₃—SO₂—N—C(=O)—N—) | H |
| O | NH—CHO | H | 2-oxoimidazolidin-1-yl (HN—C(=O)—N—) | H |
| O | NH—CHO | H | 3-(furfurylidene-amino)-2-oxoimidazolidin-1-yl (furan-CH=N—N—C(=O)—N—) | H |
| O | NH—CHO | H | 2-oxoimidazolidin-1-yl (HN—C(=O)—N—) | H₂N |
| O | NH—CHO | H | 1-methyl-2,3-dioxo-5-methylpiperazin-4-yl (CH₃—N ring with CH₃ substituent) | H |
| NH | NH—CHO | H | 1-ethyl-2,3-dioxopiperazin-4-yl | H |

TABLE 1-continued
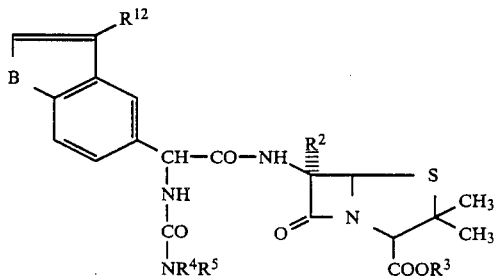
| B | R² | R³ | —NR⁴R⁵ | R¹² |
|---|---|---|---|---|
| NH | NH—CHO | H | 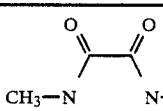 | H |
| NH | NH—CHO | $-CH_2-OCO-C(CH_3)_3$ | 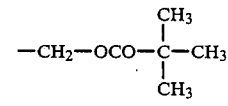 | H₂N |
| NH | NH—CHO | H | 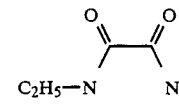 | H |
| NH | NH—CHO | H | 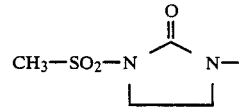 | H |
| NH | NH—CHO | H | 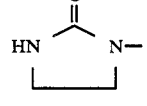 | H |
| NH | NH—CHO | H | 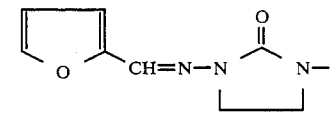 | H₂N |
| NH | NH—CHO | H | 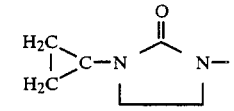 | H |
| O | H | H | 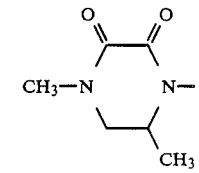 | H |
| O | H | H | 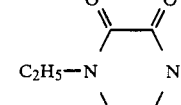 | H |

TABLE 1-continued
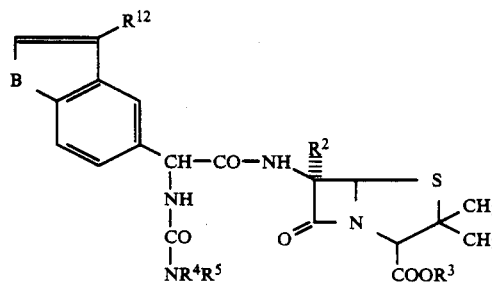
| B | R² | R³ | —NR⁴R⁵ | R¹² |
|---|---|---|---|---|
| O | H | —CH₂—OCO—C(CH₃)₃ | 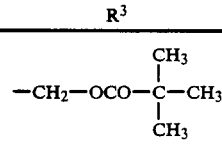 | H₂N |
| O | H | H | 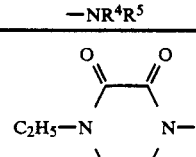 | H |
| O | H | H | 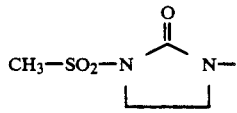 | H |
| O | H | H | 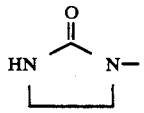 | H |
| O | H | H | 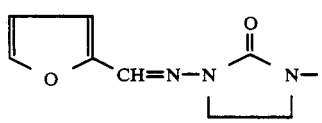 | H₂N |
| O | H | H | 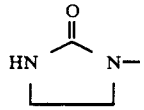 | H |

TABLE 2
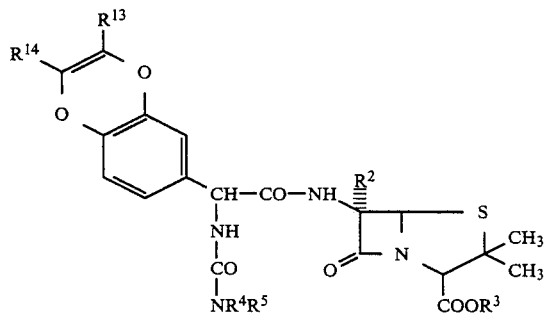
| R² | R³ | NR⁴R⁵ | R¹³ | R¹⁴ |
|---|---|---|---|---|
| H | H | 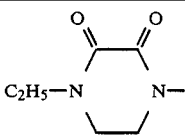 C₂H₅—N(C=O)(C=O)N— | H | H |
| H | —CH₂—OCO—CH₃ | CH₃—SO₂—N(C=O)N— | H | H |
| H | H | CH₃—N(C=O)(C=O)N— | CH₃ | CH₃ |
| H | H | HN(C=O)N— | H | H |
| H | H | CH₃—SO₂—N—CH₂—C(=O)—N— | CH₃ | CH₃ |
| H | H | CH₃—CH₂—N—CH₂—C(=O)—N— | H | H |
| H | H | (cyclopentyl)N—CH₂—C(=O)—N— | H | H |
| NH—CHO | H | C₂H₅—N(C=O)(C=O)N— | H | H |
| NH—CHO | —CH₂—OCO—CH₃ | CH₃—SO₂—N(C=O)N— | H | H |

TABLE 2-continued

| R² | R³ | NR⁴R⁵ | R¹³ | R¹⁴ |
|---|---|---|---|---|
| NH—CHO | H | CH₃—N[2,3-dioxopiperazin-1-yl]N— (4-methyl-2,3-dioxopiperazin-1-yl) | CH₃ | CH₃ |
| NH—CHO | H | HN[2-oxoimidazolidin-1-yl]N— | H | H |
| NH—CHO | H | CH₃—SO₂—N[3-oxopiperazin-1-yl]N— | CH₃ | CH₃ |
| NH—CHO | H | CH₃—CH₂—N[3-oxopiperazin-1-yl]N— | H | H |
| NH—CHO | H | cyclopentyl-N[3-oxopiperazin-1-yl]N— | H | H |

TABLE 3

| R² | R³ | NR⁴R⁵ | R¹⁶ |
|---|---|---|---|
| H | H | C₂H₅—N[2,3-dioxopiperazin-1-yl]N— | H₂N |

TABLE 3-continued

[Structure shown: R16-C(=N-)-S- attached to benzene ring with CH(NH-CO-NR4R5)-CO-NH- linked to β-lactam/thiazolidine penicillin core with R2, and C(CH3)2-CH(COOR3)]

| R² | R³ | NR⁴R⁵ | R¹⁶ |
|---|---|---|---|
| H | H | furan-2-yl-CH=N-N(-CO-N<)- (cyclic ureido with furfurylidene) | H |
| H | H | CH₃-SO₂-N(-CO-N<)- (cyclic) | CH₃ |
| H | H | H₂N-CO-N(-CO-CH(CH₃)-N<)- (cyclic) | cyclopropyl |
| H | -CH₂-O-CO-C(CH₃)₃ | C₂H₅-N(-CO-CO-)N- (dioxopiperazine) | NH₂ |
| H | H | CH₃-CO-N(-CO-CO-)N- (dioxopiperazine) | CH₃-NH |
| H | H | CH₃-SO₂-N(-CO-N<)- (cyclic) | H₂N |
| H | H | CH₃-CH₂-N(-CO-CO-)N- (dioxopiperazine) | 4-pyridyl |
| H | H | furan-2-yl-CH=N-N(-CO-N<)- (cyclic) | H₂N |
| NH-CHO | H | C₂H₅-N(-CO-CO-)N- (dioxopiperazine) | H₂N |

TABLE 3-continued

[Structure shown at top: a benzothiazoline-type aryl group with R16 substituent, connected via CH(NH-CO-NR4R5)-CO-NH- to a β-lactam bearing R2, fused to a thiazolidine with gem-dimethyl, COOR3]

| R² | R³ | NR⁴R⁵ | R¹⁶ |
|---|---|---|---|
| NH—CHO | H | furan-2-yl-CH=N—N(CO)N— (cyclic urea, 5-membered) | H |
| NH—CHO | H | CH₃—SO₂—N(CO)N— (cyclic urea) | CH₃ |
| NH—CHO | H | H₂N—CO—N(CO)—CH(CH₃)—N— (cyclic) | cyclopropyl |
| NH—CHO | —CH₂—O—CO—C(CH₃)₃ | C₂H₅—N(CO-CO)N— (piperazinedione) | NH₂ |
| NH—CHO | H | CH₃—CO—N(CO-CO)N— (piperazinedione) | CH₃—NH |
| NH—CHO | H | CH₃—SO₂—N(CO)N— (cyclic urea) | H₂N |
| NH—CHO | H | CH₃—CH₂—N(CO-CO)N— (piperazinedione) | 4-pyridyl |
| NH—CHO | H | furan-2-yl-CH=N—N(CO)N— (cyclic urea) | H₂N |

TABLE 4

| R² | R³ | NR⁴R⁵ | R¹⁶ |
|---|---|---|---|
| H | H | (piperazine-2,3-dione with C₂H₅-N and N-) | H₂N |
| H | H | furan-CH=N-N(urea ring)N- | H |
| H | H | CH₃-SO₂-N(C(=O))N- (imidazolidinone) | CH₃ |
| H | H | H₂N-CO-N(piperazine-2,3-dione)N- | cyclopropyl |
| H | -CH₂-O-CO-C(CH₃)₃ | (piperazine-2,3-dione with C₂H₅-N and N-) | NH₂ |
| H | H | CH₃-CO-N(piperazine-2,3-dione)N- | CH₃-NH |
| H | H | CH₃-SO₂-N(C(=O))N- (imidazolidinone) | H₂N |
| H | H | CH₃-CH₂-N(piperazine-2,3-dione)N- | 4-pyridyl |
| H | H | furan-CH=N-N(imidazolidinone)N- | H₂N |

TABLE 4-continued

[Structure: benzoxazole bearing $R^{16}$ substituent connected via CH(NHCONR$^4$R$^5$)—CO—NH— to a β-lactam with $R^2$, fused to thiazolidine with gem-dimethyl and COOR$^3$]

| R² | R³ | NR⁴R⁵ | R¹⁶ |
|---|---|---|---|
| NH—CHO | H | piperazine-2,3-dione with C₂H₅—N on one N | H₂N |
| NH—CHO | H | furan-2-yl-CH=N—N(CO)—N— (imidazolidinone) | H |
| NH—CHO | H | CH₃—SO₂—N(CO)N— (imidazolidinone) | CH₃ |
| NH—CHO | H | H₂N—CO—N—CH(CH₃)—CO—N— (piperazine) | cyclopropyl |
| NH—CHO | —CH₂—O—CO—C(CH₃)₃ | piperazine-2,3-dione with C₂H₅—N | NH₂ |
| NH—CHO | H | piperazine-2,3-dione with CH₃—CO—N | CH₃—NH |
| NH—CHO | H | CH₃—SO₂—N(CO)N— (imidazolidinone) | H₂N |
| NH—CHO | H | piperazine-2,3-dione with CH₃—CH₂—N | 4-pyridyl |
| NH—CHO | H | furan-2-yl-CH=N—N(CO)—N— (imidazolidinone) | H₂N |

TABLE 5

| $R^2$ | $R^3$ | $NR^4R^5$ | $R^{16}$ |
|---|---|---|---|
| H | H | $C_2H_5$-N, piperazine-2,3-dione N— | $H_2N$ |
| H | H | furan-CH=N-N(CO)-N— (cyclic) | H |
| H | H | $CH_3$-$SO_2$-N-(CO)-N— (cyclic) | $CH_3$ |
| H | H | $H_2N$-CO-N-(CO-CH(CH_3))-N— (piperazinone) | cyclopropyl |
| H | $-CH_2-O-CO-C(CH_3)_3$ | $C_2H_5$-N, piperazine-2,3-dione N— | $NH_2$ |
| H | H | $CH_3$-CO-N, piperazine-2,3-dione N— | $CH_3$-NH |
| H | H | $CH_3$-$SO_2$-N-(CO)-N— (cyclic) | $H_2N$ |
| H | H | $CH_3$-$CH_2$-N, piperazine-2,3-dione N— | 4-pyridyl |
| H | H | furan-CH=N-N-(CO)-N— (cyclic) | $H_2N$ |

TABLE 5-continued
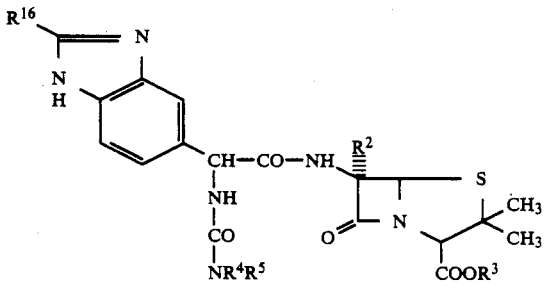
| R² | R³ | NR⁴R⁵ | R¹⁶ |
|---|---|---|---|
| NH—CHO | H | 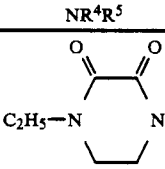 | H₂N |
| NH—CHO | H | 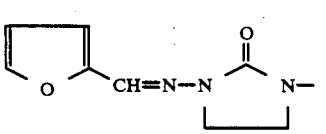 | H |
| NH—CHO | H | 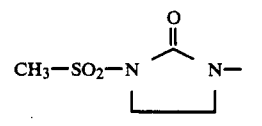 | CH₃ |
| NH—CHO | H | 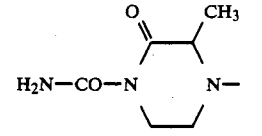 |  |
| NH—CHO | $-CH_2-O-CO-C(CH_3)_3$ | 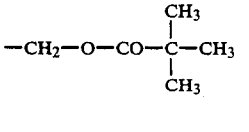 | NH₂ |
| NH—CHO | H | 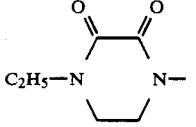 | CH₃—NH |
| NH—CHO | H | 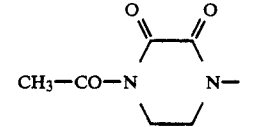 | H₂N |
| NH—CHO | H | 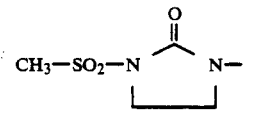 | 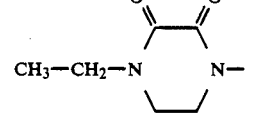 |
| NH—CHO | H | 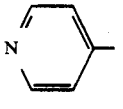 | H₂N |
The following compounds may be mentioned in addition to the experimental examples as new active compounds from the cephalosporin series:

TABLE 6
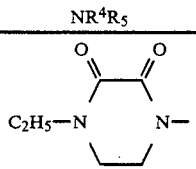
| A | R² | NR⁴R⁵ | R¹² | T |
|---|----|-------|-----|---|
| NH | H | 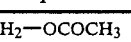 | H | $-CH_2-OCOCH_3$ |
| NH | H | 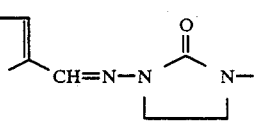 | H | 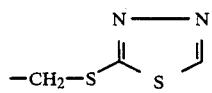 |
| NH | H | 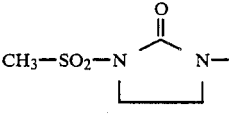 | $NH_2$ | 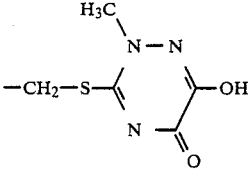 |
| NH | H | 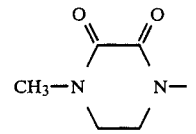 | H | 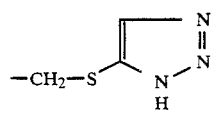 |
| NH | H | 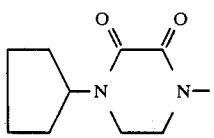 | $NH_2$ | 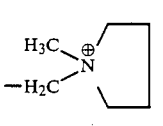 |
| NH | H | 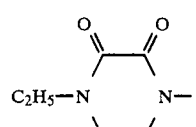 | $CH_3$ | 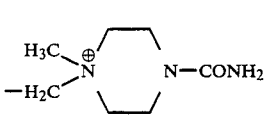 |
| NH | H | 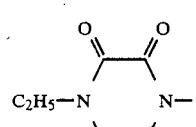 | H | 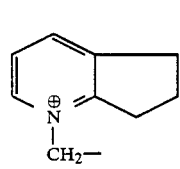 |
| O | NH—CHO | 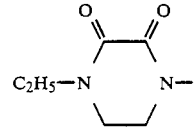 | H | $-CH_2-OCOCH_3$ |
| O | NH—CHO | 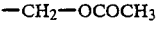 | H | 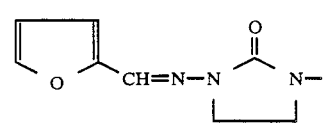 |

TABLE 6-continued
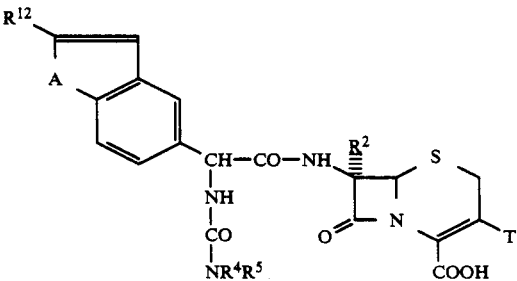
| A | R² | NR⁴R₅ | R¹² | T |
|---|----|-------|-----|---|
| O | NH—CHO | 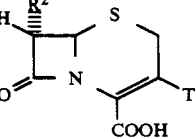 | NH₂ | 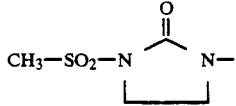 |
| O | NH—CHO | 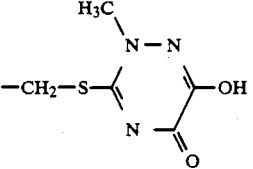 | H | 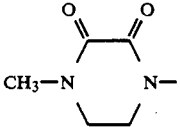 |
| O | NH—CHO | 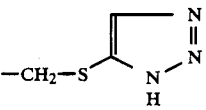 | NH₂ | 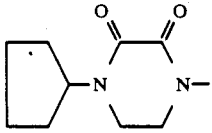 |
| O | NH—CHO | 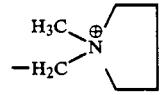 | CH₃ | 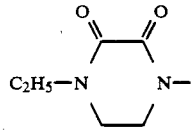 |
| O | NH—CHO |  | H | 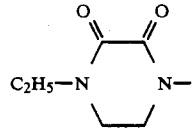 |
| O | H | 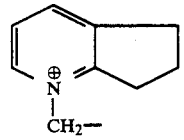 | H | —CH₂—OCOCH₃ |
| O | H | 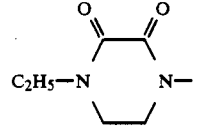 | H | 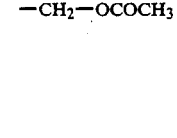 |
| O | H | 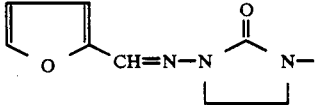 | NH₂ | 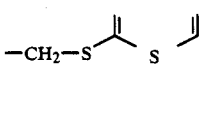 |

TABLE 6-continued
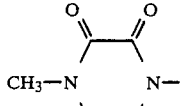
| A | R² | NR⁴R₅ | R¹² | T |
|---|---|---|---|---|
| O | H | 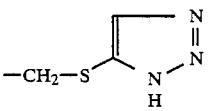 | H | 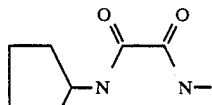 |
| O | H | 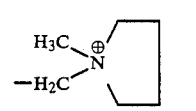 | NH₂ | 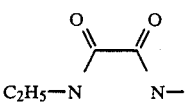 |
| O | H | 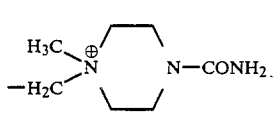 | CH₃ | 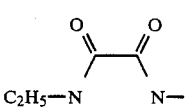 |
| O | H | 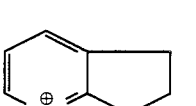 | H | 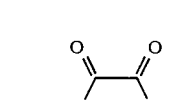 |
| NH | NH—CHO | 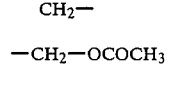 | H | —CH₂—OCOCH₃ |
| NH | NH—CHO | 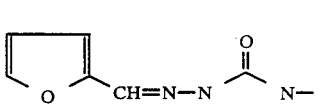 | H | 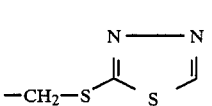 |
| NH | NH—CHO | 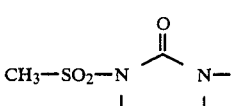 | NH₂ | 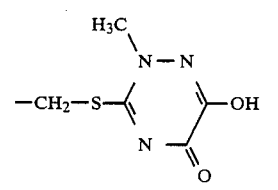 |
| NH | NH—CHO | 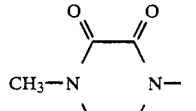 | H | 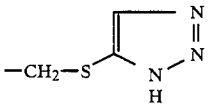 |
| NH | NH—CHO | 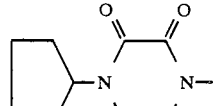 | NH₂ | 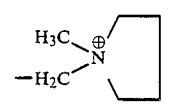 |

TABLE 6-continued

[Structure: bicyclic aromatic (A-containing) with R12 substituent, connected via CH(NHCONR4R5)-CO-NH- to β-lactam-thiazine with COOH and T substituent]

| A | R² | NR⁴R₅ | R¹² | T |
|---|----|----|-----|---|
| NH | NH—CHO | [piperazine-2,3-dione with C₂H₅-N] | CH₃ | [H₃C-N⁺(CH₂-)(piperazine)-N-CONH₂] |
| NH | NH—CHO | [piperazine-2,3-dione with C₂H₅-N] | H | [cyclopenta-fused pyridinium with -CH₂-] |

TABLE 7

[Structure: catechol-type aromatic with R¹³, R¹⁴ on dioxole-like ring, connected via CH(NHCONR⁴R⁵)-CO-NH- to β-lactam with COOR³ and T substituent]

| R² | R³ | NR⁴R⁵ | R¹³ | R¹⁴ | T |
|----|----|-------|-----|-----|---|
| H | H | [CH₃—SO₂—N, C(=O), N— imidazolidinone] | H | H | —CH₂—OCOCH₃ |
| H | H | [piperazine-2,3-dione with C₂H₅-N] | H | H | —CH₂—S—[1,3,4-thiadiazole] |
| H | H | [cyclopropyl-imidazolidinone: H₂C-C(H₂C)-N, C(=O), N—] | CH₃ | CH₃ | —CH₂—S—[tetrazole-N-CH₃] |
| H | H | [piperazine-2,3-dione with C₂H₅-N] | H | H | —CH₂—N⁺(pyridinium) |

TABLE 7-continued
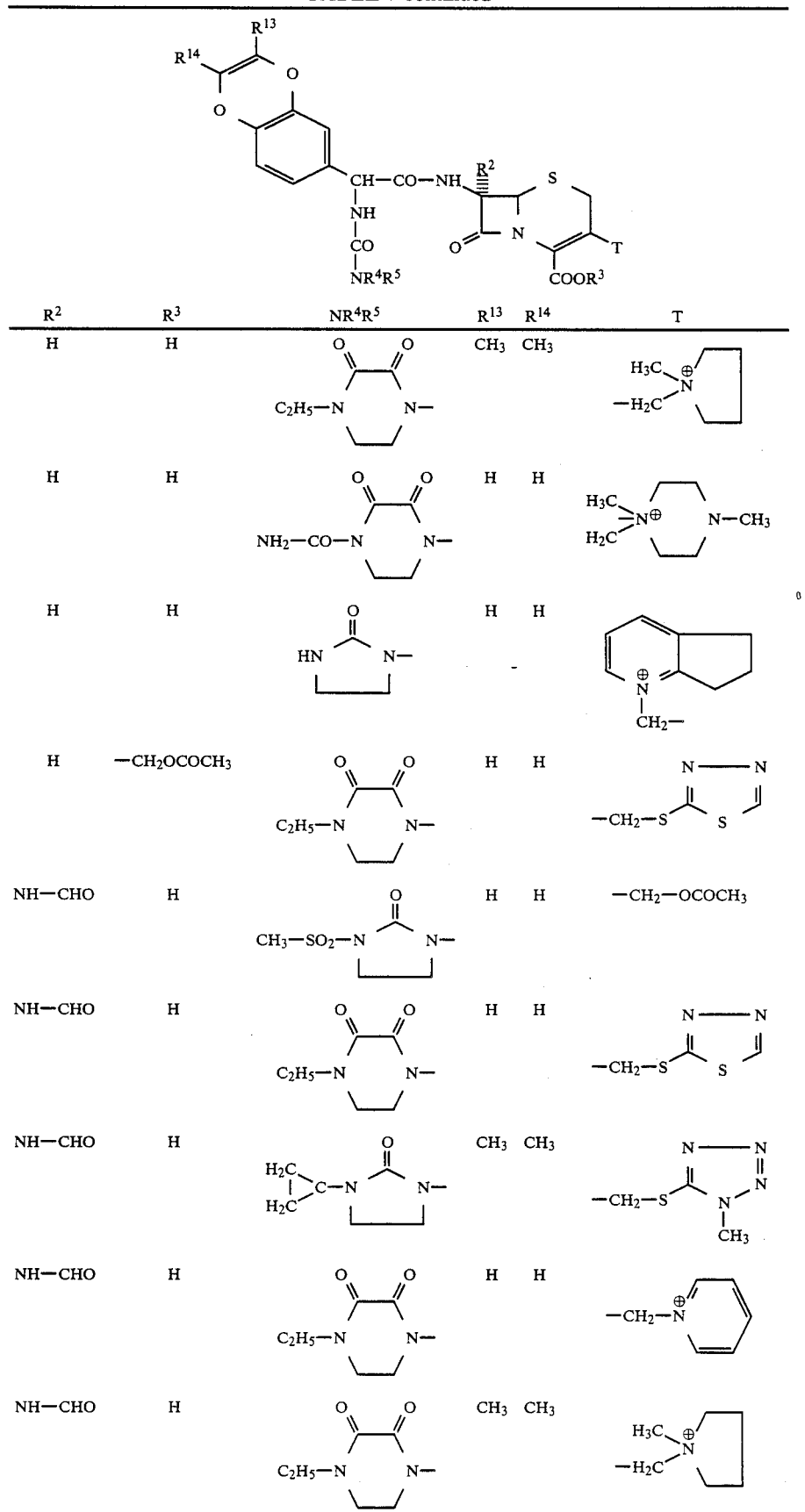

TABLE 7-continued
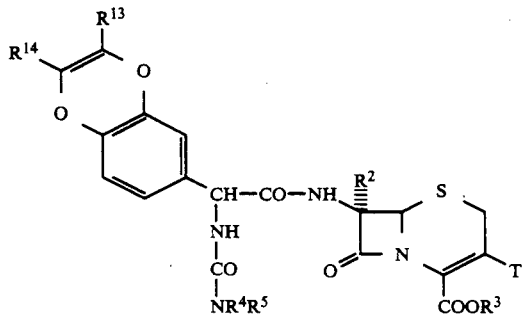
| R² | R³ | NR⁴R⁵ | R¹³ | R¹⁴ | T |
|---|---|---|---|---|---|
| NH—CHO | H | 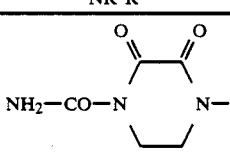 | H | H | 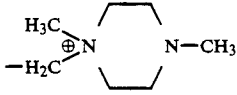 |
| NH—CHO | H | 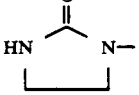 | H | H | 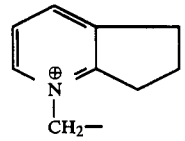 |
| NH—CHO | —CH₂OCOCH₃ | 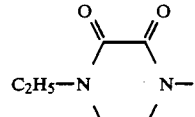 | H | H | 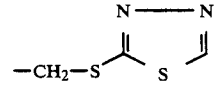 |
TABLE 8
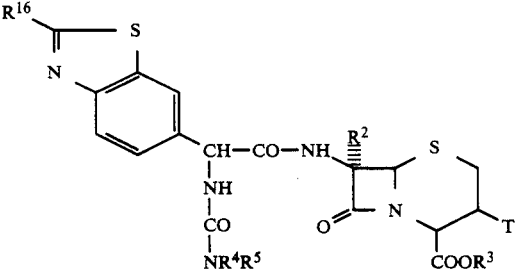
| R² | R³ | NR⁴R⁵ | R¹⁶ | T |
|---|---|---|---|---|
| H | H | 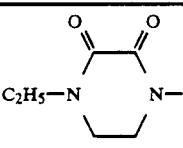 | H₂N | 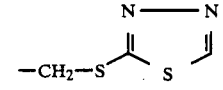 |
| H | H | 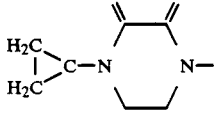 | H₂N | 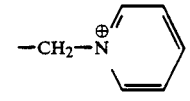 |
| H | H | 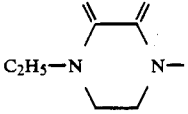 | CH₃ | —CH₂—OCOCH₃ |

TABLE 8-continued

[Structure shown at top of table: a compound with R¹⁶-C(=N)-S attached to a benzothiazole-like ring linked via CH to C(=O)-NH, with NH-CO-NR⁴R⁵ branch, connected to a β-lactam bearing R² and S-CH₂-CH(T)-COOR³]

| R² | R³ | NR⁴R⁵ | R¹⁶ | T |
|----|----|----|-----|---|
| H | H | 1-ethyl-2,3-dioxopiperazin-4-yl | NH₂ | -CH₂-S-(1-methylpyridinium-4-yl) |
| H | H | 1-ethyl-2,3-dioxopiperazin-4-yl | NH₂ | 1-(carboxymethyl)-4-(methylthio)pyridinium |
| H | H | 1-ethyl-2,3-dioxopiperazin-4-yl | cyclopropyl (H₂C-CH₂-C-) | 1-methyl-1-(pyrrolidinium)methyl (H₃C-N⁺(CH₂-)pyrrolidine) |
| H | H | 1-(furan-2-ylmethylene-hydrazinocarbonyl)imidazolidin-3-yl | H₂N-CH₂- | -CH₂-S-(1,2,3-thiadiazol-4-yl) |
| H | H | 1-(methylsulfonylaminocarbonyl)imidazolidin-3-yl | 4-pyridyl | -CH₂-N⁺(pyridinium) |
| H | H | 1-ethyl-2,3-dioxopiperazin-4-yl | H₃C-CH(NH₂)- | -CH₂-N⁺(CH₃)(morpholino) |
| H | H | 1-(methylsulfonylaminocarbonyl)imidazolidin-3-yl | H | -CH₂-S-(1,3,4-thiadiazol-2-yl) |
| H | H | 1-acetyl-2,3-dioxopiperazin-4-yl | NH₂ | -CH₂-N⁺(CH₃)₃ |
| H | H | 1-(1-cyclopropyl)-2-oxoimidazolidin-3-yl | H₂N-SO₂ | -CH₂-OCOCH₃ |

TABLE 8-continued

[Structure: R16-substituted benzothiazole-CH(NHCONR4R5)-CO-NH-C(R2)(azetidinone-S-CH2-CH(T)-COOR3)]

| $R^2$ | $R^3$ | $NR^4R^5$ | $R^{16}$ | T |
|---|---|---|---|---|
| H | H | 1-ethyl-4-yl-2,3-dioxopiperazine | phenyl | -CH2-(1,2,3-thiadiazol-5-yl) |
| H | -CH2OCOCH3 | 1-ethyl-4-yl-2,3-dioxopiperazine | NH2 | -CH2-N⊕(thieno[3,2-b]pyridinium) with CH3 |
| NH-CHO | H | 1-ethyl-4-yl-2,3-dioxopiperazine | H2N | -CH2-S-(1,3,4-thiadiazol-2-yl) |
| NH-CHO | H | 1-(1-methylcyclopropyl)-4-yl-2,3-dioxopiperazine | H2N | -CH2-N⊕(pyridinium) |
| NH-CHO | H | 1-ethyl-4-yl-2,3-dioxopiperazine | CH3 | -CH2-OCOCH3 |
| NH-CHO | H | 1-ethyl-4-yl-2,3-dioxopiperazine | NH2 | -CH2-S-(1-methylpyridinium-4-yl) |
| NH-CHO | H | 1-ethyl-4-yl-2,3-dioxopiperazine | NH2 | -CH2-S-(4-yl)-pyridinium-N-CH2COOH |
| NH-CHO | H | 1-ethyl-4-yl-2,3-dioxopiperazine | 1-methylcyclopropyl | -CH2-N⊕(CH3)2-CH2- (cyclic) |

TABLE 8-continued

| R² | R³ | NR⁴R⁵ | R¹⁶ | T |
|---|---|---|---|---|
| NH—CHO | H | furan-CH=N-N(–)C(O)N(–) (cyclic) | H₂N—CH₂— | —CH₂—S-(1,2,3-thiadiazol-5-yl) |
| NH—CHO | H | CH₃—SO₂—N(–)C(O)N(–) (cyclic) | 4-pyridyl | —CH₂—N⁺(pyridinium) |
| NH—CHO | H | C₂H₅—N(–)C(O)C(O)N(–) (cyclic) | H₃C-CH(NH₂)– | —CH₂—N⁺(CH₃)(morpholino) |
| NH—CHO | H | CH₃—SO₂—N(–)C(O)N(–) (cyclic) | H | —CH₂—S-(1,3,4-thiadiazol-2-yl) |
| NH—CHO | H | CH₃—CO—N(–)C(O)C(O)N(–) (cyclic) | NH₂ | —CH₂—N⁺(CH₃)₃ |
| NH—CHO | H | (CH₂CH₂)C—N(–)C(O)N(–) (cyclic, cyclopropyl) | H₂N—SO₂ | —CH₂—OCOCH₃ |
| NH—CHO | H | C₂H₅—N(–)C(O)C(O)N(–) (cyclic) | phenyl | —CH₂-(isothiazol-5-yl) |
| NH—CHO | —CH₂OCOCH₃ | C₂H₅—N(–)C(O)C(O)N(–) (cyclic) | NH₂ | —CH₂—N⁺(dihydrothieno[3,2-b]pyridinium) |

TABLE 9

| R² | R³ | NR⁴R⁵ | R¹⁶ | T |
|---|---|---|---|---|
| H | H | (2,3-dioxo-4-ethylpiperazin-1-yl) | H₂N | -CH₂-S-(1,3,4-thiadiazol-2-yl) |
| H | H | (2,3-dioxo-4-(1-methylcyclopropyl)piperazin-1-yl) | H₂N | -CH₂-N⁺(pyridinium) |
| H | H | (2,3-dioxo-4-ethylpiperazin-1-yl) | CH₃ | -CH₂-OCOCH₃ |
| H | H | (2,3-dioxo-4-ethylpiperazin-1-yl) | NH₂ | -CH₂-S-(1-methylpyridinium-4-yl) |
| H | H | (2,3-dioxo-4-ethylpiperazin-1-yl) | NH₂ | 1-(carboxymethyl)-4-(thiomethyl)pyridinium |
| H | H | (2,3-dioxo-4-ethylpiperazin-1-yl) | (1-methylcyclopropyl) | -CH₂-N⁺(dimethylpyrrolidinium) |
| H | H | (furan-2-yl-CH=N-N-CO-N-, cyclic) | H₂N-CH₂- | -CH₂-S-(1,2,3-thiadiazol-4-yl) |
| H | H | (CH₃-SO₂-N-CO-N-, cyclic) | 4-pyridyl | -CH₂-N⁺(pyridinium) |
| H | H | (2,3-dioxo-4-ethylpiperazin-1-yl) | H₃C-CH(NH₂)- | -CH₂-N⁺(methylmorpholinium) |

TABLE 9-continued

| $R^2$ | $R^3$ | $NR^4R^5$ | $R^{16}$ | T |
|---|---|---|---|---|
| H | H | $CH_3-SO_2-N\overset{O}{\underset{\_\_\_}{\diagdown}}N-$ (imidazolidinone) | H | $-CH_2-S-\underset{S}{\overset{N=N}{\diagup}}$ (thiadiazole) |
| H | H | $CH_3-CO-N\overset{O\ O}{\underset{\_\_\_}{\diagdown}}N-$ (dioxopiperazine) | $NH_2$ | $-CH_2-\overset{\oplus}{N}(CH_3)_3$ |
| H | H | $\overset{H_2C}{\underset{H_2C}{>}}C-N\overset{O}{\underset{\_\_\_}{\diagdown}}N-$ | $H_2N-SO_2$ | $-CH_2-OCOCH_3$ |
| H | H | $C_2H_5-N\overset{O\ O}{\underset{\_\_\_}{\diagdown}}N-$ | (phenyl) | $-CH_2-\underset{S}{\overset{N=N}{\diagup}}$ (isothiazole) |
| H | $-CH_2OCOCH_3$ | $C_2H_5-N\overset{O\ O}{\underset{\_\_\_}{\diagdown}}N-$ | $NH_2$ | $-CH_2-\overset{\oplus}{N}$(thienopyridinium) |
| NH—CHO | H | $C_2H_5-N\overset{O\ O}{\underset{\_\_\_}{\diagdown}}N-$ | $H_2N$ | $-CH_2-S-\underset{S}{\overset{N=N}{\diagup}}$ |
| NH—CHO | H | $\overset{H_2C}{\underset{H_2C}{>}}C-N\overset{O\ O}{\underset{\_\_\_}{\diagdown}}N-$ | $H_2N$ | $-CH_2-\overset{\oplus}{N}$(pyridinium) |
| NH—CHO | H | $C_2H_5-N\overset{O\ O}{\underset{\_\_\_}{\diagdown}}N-$ | $CH_3$ | $-CH_2-OCOCH_3$ |
| NH—CHO | H | $C_2H_5-N\overset{O\ O}{\underset{\_\_\_}{\diagdown}}N-$ | $NH_2$ | $-CH_2-S-\underset{}{}\overset{\oplus}{N}-CH_3$ |

TABLE 9-continued
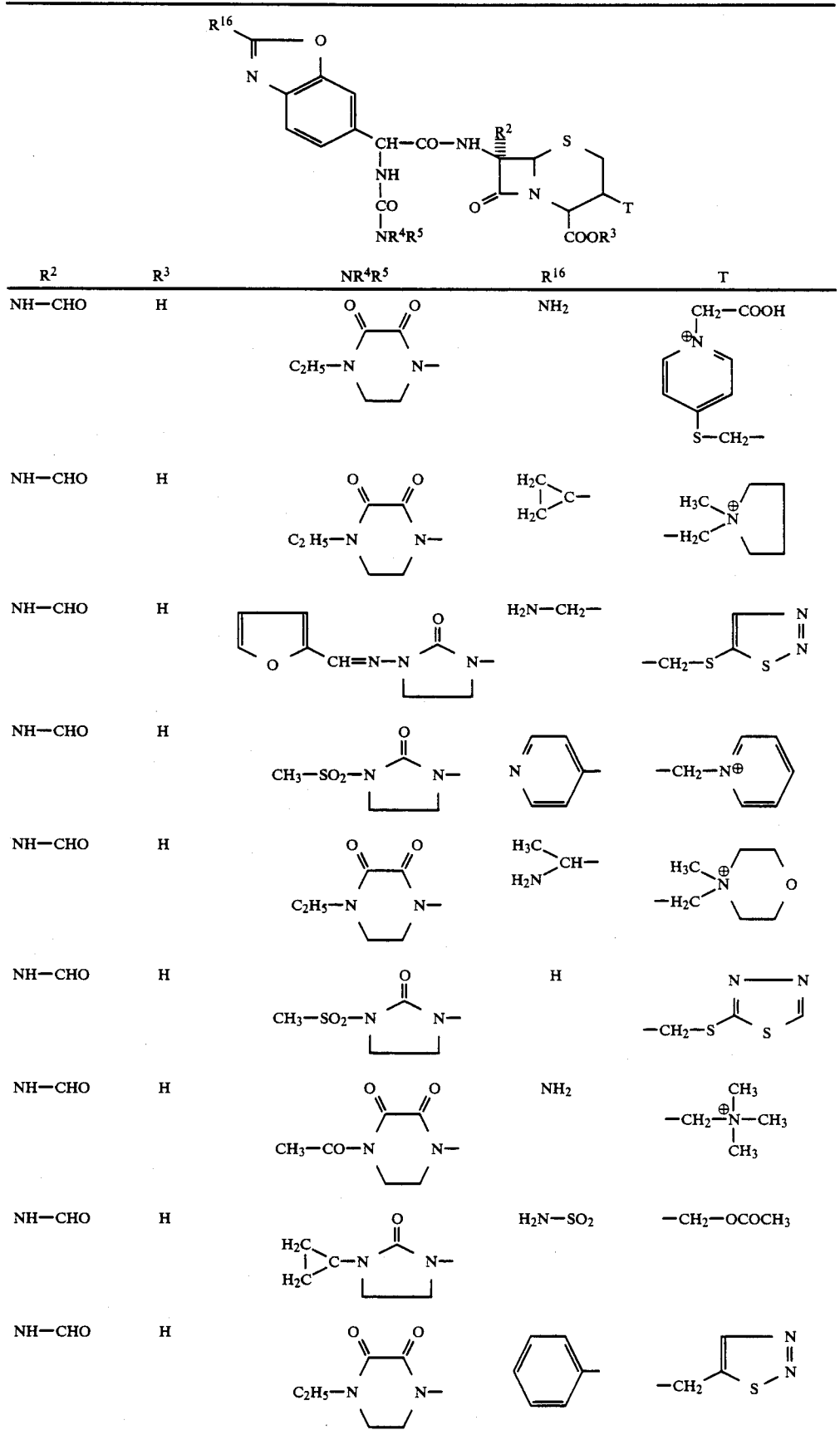

TABLE 9-continued

| R² | R³ | NR⁴R⁵ | R¹⁶ | T |
|---|---|---|---|---|
| NH—CHO | —CH₂OCOCH₃ | C₂H₅—N(C=O)(C=O)N— (piperazine-2,3-dione) | NH₂ | —CH₂—[thieno-pyridinium] |

TABLE 10

| R² | R³ | NR⁴R⁵ | R¹⁶ | T |
|---|---|---|---|---|
| H | H | C₂H₅—N(C=O)(C=O)N— | H₂N | —CH₂—S—[1,3,4-thiadiazole] |
| H | H | (H₂C-CH₂)C—N(C=O)(C=O)N— | H₂N | —CH₂—N⊕(pyridinium) |
| H | H | C₂H₅—N(C=O)(C=O)N— | CH₃ | —CH₂—OCOCH₃ |
| H | H | C₂H₅—N(C=O)(C=O)N— | NH₂ | —CH₂—S—[pyridinium]⊕N—CH₃ |
| H | H | C₂H₅—N(C=O)(C=O)N— | NH₂ | [pyridinium-CH₂COOH with 4-S—CH₂—] |

TABLE 10-continued

| R² | R³ | NR⁴R⁵ | R¹⁶ | T |
|---|---|---|---|---|
| H | H | (ethyl-substituted piperazine-2,3-dione) | cyclopropyl-C | (1-methylpyrrolidinium-methyl) |
| H | H | (furfurylidene-hydrazino-imidazolidinone) | H₂N—CH₂— | —CH₂—S—(1,2,3-thiadiazol-5-yl) |
| H | H | (methylsulfonyl-imidazolidinone) | 4-pyridyl | —CH₂—N⁺(pyridinium) |
| H | H | (ethyl-substituted piperazine-2,3-dione) | H₃C-CH(NH₂)— | (N-methyl-morpholinium-methyl) |
| H | H | (methylsulfonyl-imidazolidinone) | H | —CH₂—S—(1,3,4-thiadiazol-2-yl) |
| H | H | (acetyl-substituted piperazine-2,3-dione) | NH₂ | —CH₂—N⁺(CH₃)₃ |
| H | H | (cyclopropyl-substituted imidazolidinone) | H₂N—SO₂ | —CH₂—OCOCH₃ |
| H | H | (ethyl-substituted piperazine-2,3-dione) | phenyl | —CH₂—(1,2-thiazol-5-yl) |
| H | —CH₂OCOCH₃ | (ethyl-substituted piperazine-2,3-dione) | NH₂ | —CH₂—(thieno[3,2-b]pyridinium) |

TABLE 10-continued

[Structure shown: core scaffold with R¹⁶-C(=N)-NH- group on aniline ring, connected via CH-CO-NH to β-lactam with R² substituent, S-containing dihydrothiazine with =CH-T and COOR³; CH also bears NH-CO-NR⁴R⁵]

| R² | R³ | NR⁴R⁵ | R¹⁶ | T |
|---|---|---|---|---|
| NH—CHO | H | 4-ethyl-2,3-dioxopiperazin-1-yl | H₂N | —CH₂—S—(1,3,4-thiadiazol-2-yl) |
| NH—CHO | H | 4-(1-cyclopropyl)-2,3-dioxopiperazin-1-yl | H₂N | —CH₂—N⁺(pyridinium) |
| NH—CHO | H | 4-ethyl-2,3-dioxopiperazin-1-yl | CH₃ | —CH₂—OCOCH₃ |
| NH—CHO | H | 4-ethyl-2,3-dioxopiperazin-1-yl | NH₂ | —CH₂—S—(1-methylpyridinium-4-yl) |
| NH—CHO | H | 4-ethyl-2,3-dioxopiperazin-1-yl | NH₂ | —CH₂—S—(1-carboxymethylpyridinium-4-yl) |
| NH—CHO | H | 4-ethyl-2,3-dioxopiperazin-1-yl | 1-aminocyclopropyl (H₂C-CH₂-C-) | —CH₂—N⁺(CH₃)(pyrrolidinyl) |
| NH—CHO | H | 3-(furan-2-ylmethylenehydrazinocarbonyl)-2-oxoimidazolidin-1-yl | H₂N—CH₂— | —CH₂—S—(isothiazol-5-yl with N=N) |
| NH—CHO | H | 3-(methylsulfonyl)-2-oxoimidazolidin-1-yl | 4-pyridyl | —CH₂—N⁺(pyridinium) |
| NH—CHO | H | 4-ethyl-2,3-dioxopiperazin-1-yl | CH₃—CH(NH₂)— | —CH₂—N⁺(CH₃)(morpholinyl) |

TABLE 10-continued

[Structure: substituted phenyl with R16-amidine group, CH(NHCONR4R5)-CO-NH- attached to β-lactam with R2, S, and cephem ring with COOR3 and T substituent]

| R² | R³ | NR⁴R⁵ | R¹⁶ | T |
|---|---|---|---|---|
| NH—CHO | H | CH₃—SO₂—N⟨imidazolidin-2-on-1-yl⟩N— | H | —CH₂—S—(1,3,4-thiadiazol-2-yl) |
| NH—CHO | H | CH₃—CO—N⟨2,3-dioxopiperazin-1-yl⟩N— | NH₂ | —CH₂—N⁺(CH₃)₃ |
| NH—CHO | H | (H₂C)₂C—N⟨imidazolidin-2-on-1-yl⟩N— | H₂N—SO₂ | —CH₂—OCOCH₃ |
| NH—CHO | H | C₂H₅—N⟨2,3-dioxopiperazin-1-yl⟩N— | C₆H₅— | —CH₂—(1,2,3-thiadiazol-4-yl) |
| NH—CHO | —CH₂OCOCH₃ | C₂H₅—N⟨2,3-dioxopiperazin-1-yl⟩N— | NH₂ | —CH₂—N⁺(thieno[3,2-b]pyridinium) |

The following compounds in the form of their sodium salts may be mentioned individually as new active compounds:

D-6-[α-(4-ethyl-2,3-dioxo-1-piperazino-carbonylamino)-α-(indol-5-yl)glycyl]penicillanic acid D-6-[α-(imidazolidin-2-on-1-yl)carbonylamino-α-(indol-5-yl)glycylamido]penicillanic acid D-6-[α(4-ethyl-2,3-dioxo-1-piperazino-carbonylamino)-α-(benzofur-5-yl)glycylamido]penicillanic acid 6α-formamido-6β-{D-α-[(4-ethyl-2,3-dioxo-piperazin-1-yl)-carbonylamino]-α-(benzofur-5-yl)glycylamido}-penicillanic acid D-6-[α-(2-oxo-3-furylideneamino-imidazoliden-1-yl-carbonylamino)-α-(benzofur-5-yl)-glycylamido]-penicillanic acid D-6-[α-(4-methyl-2,3-dioxo-1-piperazino-carbonylamino)-α-(1,4-benzodioxin-6-yl)glycylamido]-penicillanic acid 6α-formamido-6β-{D-α-[4-ethyl-2,3-dioxo-piperazin-1-yl)-carbonylamino]-α-(1,4-benzodioxin-6-yl)glycylamido}-penicillanic acid D-6-[α(4-ethyl-2,3-dioxo-1-piperazino-carbonylamino)-α-(2-methylbenzothiazol-6-yl)glycylamido]penicillanic acid 6α-formamido-6β-{D-α-[(4-ethyl-2,3-dioxo-piperazin-1-yl)-carbonylamino]-α-(2-methylbenzothiazol-6-yl)glycylamido}penicillanic acid 6α-formamido-6β-{D-α-[(4-ethyl-2,3-dioxopiperazin-1-yl)-carbonylamino]-α-(2-aminobenzothiazol-6-yl)glycylamido}penicillanic acid 6α-formamido-6β-{D-α-[(3-methylsulphonyl-imidazolidin-2-on-1-yl)carbonylamino]-α-(2-aminobenzothiazol-6-yl)glycylamido}penicillanic acid D-6-[α-(-4-ethyl-2,3-dioxo-1-piperazino-carbonylamino)-α-(2-cyclopropylbenzothiazol-6-yl)glycylamido]penicillanic acid D-6-[α-(4-ethyl-2,3-dioxo-1-piperazino-carbonylamino)-α-(2-aminobenzoxazol-5-yl)glycylamido]penicillanic acid D-6-[α-(4-ethyl-2,3-dioxo-1-piperazino-carbonylamino)-α-(2-aminobenzoxazol-6-yl)glycylamido penicillanic acid 6α-formamido-6β-{D-α-[(3-methylsulphonyl-imidazolidin-2-on-1-yl)carbonylamino]-α-(2-aminobenzoxazol-6-yl)glycylamido}penicillanic acid 6α-formamido-6β-{D-α-[(4-ethyl-2,3-dioxopiperazin-1-yl)-carbonylamino]-α-(2-aminobenzoxazol-6-yl)glycylamido}-penicillanic acid D-6-[α-(4-ethyl-2,3-dioxo-1-piperazino-carbonylamino)-α-(2-amino-1H-benzimidazol-5-yl)glycylamido penicillanic acid 6α-formamido-6β-{D-α-[4-ethyl-2,3-dioxopiperazin-1-yl)-carbonylamino]-α-(2-amino-1H-benzimidazol-5-yl)glycylamido}penicillanic acid D-6-[α-(3-methylsulphonyl-imidazolidin-2-on-1-yl-carbonylamino)-α-(2-methyl-1H-benzimidazol-5-yl)glycylamido]penicillanic acid 6α-formamido-6β-{D-α-[(3-ethyl-2,3-dioxopiperazin-yl)-carbonylamino]-α-(2-methyl-1H-benzimidazol-5-yl)glycylamido} penicillanic acid D-6-[α-(4-ethyl-2,3-dioxo-1-piperazino-carbonylamino)-α-(2-cyclopropyl-1H-benzimidazol-5-yl)glycylamido]penicillanic acid D-7-[α-(4-ethyl-2,3-dioxo-1-piperazino-carbonylamino)-α-(indol-5-yl)glycylamido]-3-acetoxymethyl-3-cephem-4-carboxylic acid 7β-{D-α-[(4-ethyl-2,3-dioxopiperazin-1-yl)carbonylamino]-α-(indol-5-yl)glycylamido}-7α-formamido-3-(pyridiniomethyl)-3-cephem-4-carboxylic acid 7β-{D-α-[(4-ethyl-2,3-dioxopiperazin-1-yl)carbonylamino]-α-(indol-5-yl)glycylamido}-7-α-formamido-3-[(1,3,4-thiadiazol-2-yl)thiomethyl]-3-cephem-4-carboxylic acid D-7-[α-(4-ethyl-2,3-dioxo-1-piperazino-carbonylamino)-α-(benzofur-5-yl)glycylamido)-3-(pyridiniomethyl)-3-cephem-4-carboxylic acid 7β-{D-α-(4-ethyl-2,3-dioxo-1-piperazino-carbonylamino-α-(benzofur-5-yl)glycylamido}-7α-formamido-3-(1-methyl-1H-tetrazol-5-yl-thiomethyl)-3-cephem-4-carboxylic acid D-7-[α-(2-oxo-3-furylideneamino-imidazolidin-1-yl-carbonylamino)-α-(benzofur-5-yl)glycylamido]-3-[(1,3,4-thiadiazol-2-yl)thiomethyl]-3-cephem-4-carboxylic acid 7β-[D-α-(4-ethyl-2,3-dioxo-1-piperazino-carbonylamino)-α-(benzofur-5-yl)glycylamido]-7α-formamido-3-[(1,3,4-thiadiazol-2-yl)thiomethyl]-3-cephem-4-carboxylic acid D-7-[α-(4-ethyl-2,3-dioxo-1-piperazino-carbonylamino)-α-(1,4-benzodioxin-6-yl)glycylamido]-3-(pyridiniomethyl)- 3-cephem-4-carboxylic acid 7β-[D-α-(ethyl-2,3-dioxo-1-piperazino-carbonylamino)-α-(1,4-benzodioxin-6-yl)glycylamido]-7α-formamido-3-(1-methyl-1H-tetrazol-5-yl-thiomethyl)-3-cephem-4-carboxylic acid D-7-[α-(4-ethyl-2,3-dioxo-1-piperazino-carbonylamino)-α-(2-methylbenzothiazol-6-yl)glycylamido]-3-(pyridiniomethyl)-3-cephem-4-carboxylic acid 7β-[D-α-(4-ethyl-2,3-dioxo-1-piperazino-carbonylamino)-α-(2-cyclopropylbenzothiazol-6-yl)glycylamido]-7α-formamido-3-[(1,3,4-thiadiazol-2-yl)thiomethyl]-3-cephem-4-carboxylic acid 7β-[D-α(3-Cyclopropyl-imidazolidin-2-on-1-yl-carbonylamino)-α-(2-aminobenzothiazol-6-yl)glycylamido]-7α-formamido-3[(1,3,4-thiadiazol-2-yl)thiomethyl]-3-cephem-4-carboxylic acid D-7-[α-(4-ethyl-2,3-dioxo-1-piperazino-carbonylamino)-α-(2-aminobenzoxazol-5-yl)glycylamido]-3-(pyridiniomethyl)-3-cephem-4-carboxylic acid D-7-[α-(4-ethyl-2,3-dioxo-1-piperazino-carbonylamino)-α-(2-aminobenzoxazol-5-yl)glycylamido]-3-[(1-methyl-1-pyrrolidinium)methyl]-3-cephem-4-carboxylic acid D-7-[α-(4-ethyl-2,3-dioxo-1-piperazino-carbonylamino)-α-(2-amino-1H-benzimidazol-5-yl)glycylamido]-3-acetoxymethyl-3-cephem-4-carboxylic acid 7β-[D-α-(4-ethyl-2,3-dioxopiperazin-1-yl)carbonylamino)-α-(2-amino-1H-benzimidazol-5-yl)glycylamido]-7α-formamido-3-(pyridiniomethyl)-3-cephem-4-carboxylic acid 7β-{D-α-[(4-ethyl-2,3-dioxopiperazin-1-yl)-carbonylamino]-α-(2-methyl-1H-benzimidazol-5-yl)glycylamido}-7α-formamido-3-(1-methyl-1H-tetrazol-5-yl-thiomethyl)-3-cephem-4-carboxylic acid D-7-[α-(4-ethyl-2,3-dioxo-1-piperazino-carbonylamino)-α-(2-amino-1H-benzimidazol-5-yl)glycylamido]-7α-formamido-3-[(2,3-cyclopenteno-1-pyridinio)methyl]-3-cephem-4-carboxylic acid D-7-[α-(2-oxo-3-furylideneamino-imidazolidin-1-yl-carbonylamido)-α-(2-amino-1H-benzimidazol-5-yl)glycylamido]-7α-formamido-3-[(1,3,4-thiadiazol-2-yl)thiomethyl]-3-cephem-4-carboxylic acid The compounds of the general formula I according to the invention exhibit a wide antibacterial spectrum against gram positive and gram negative bacteria, combined with low toxicity. These properties make possible their use as chemotherapeutic active compounds in human and veterinary medicine.

The compounds according to the invention are active against a very wide spectrum of microorganisms. Gram negative and gram positive bacteria and bacteria-like microorganisms can be controlled with their aid, and the diseases produced by these pathogens can also be prevented, improved and/or cured.

The compounds according to the invention are particularly active against bacteria and bacteria-like microorganisms. They are therefore particularly well suited in human and veterinary medicine for the prophylaxis and chemotherapy of local and systemic infections which are produced by these pathogens.

For example, local and/or systemic diseases which are caused by the following pathogens or by mixtures of the following pathogens can be treated and/or prevented: gram positive cocci, for example staphylococci (*Staph. aureus, Staph. epidermis*) and streptococci (*Strept. agalactiae, Strept. faecalis, Strept. pneumoniae, Strept. pyogenes*); gram negative cocci (*Neisseria gonorrhoeae*) and also gram negative rods such as Enterobacteriaceae, for example *Escherichia coli, Haemophilus influenzae,* Citrobacter (*Citrob. freundii, Citrob. divernis*), Salmonella and Shigella; furthermore Klebsiella (*Klebs. pneumoniae, Klebs. oxytoca*), Enterobacter (*Ent. aerogenes, Ent. agglomerans*), Hafnia, Serratia (*Serr. marcescens*), Proteus (*Pr. mirabilis, Pr. rettgeri, Pr. vulgaris*), Providencia, Yersinia, and also the order Acinetobacter. Moreover, the antibacterial spectrum comprises the order Pseudomonas (*Ps. aeruginosa, Ps. maltophilia*) and also strictly anaerobic bacteria such as, for example, *Bacteroides fragilis, representatives of the order Peptococcus, Peptostreptococcus and also the order Clostridium; furthermore mycoplasma (M. pneumoniae, M. hominis, M. urealyticum*) and also mycobacteria, for example Mycobacterium tuberculosis. The substances according to the invention act in particular against staphylococci, streptococci, enterococci and *Haemophilus influenzae*. On parenteral or, in particular, oral administration, the new compounds are highly active against microorganisms such as staphylococci, streptococci, Enterobacteriaceae, *Escherichia coli*, Klebsiella, Salmonella, Shigella and Proteus.

The above enumeration of pathogens is merely for example and in no way to be conceived as limiting. Examples of diseases which may be caused by the said pathogens or mixed infections and which may be prevented, improved or cured by the compounds according to the invention are, for example: infectious diseases in humans, such as, for example, otitis, pharyngitis, pneumonia, peritonitis, pyelonephritis, cystitis, endocarditis, systemic infections, bronchitis (acute, chronic), septic infections, diseases of the upper airways, diffuse panbronchiolitis, pulmonary emphysema, dysentery, enteritis, hepatic abscesses, urethritis, prostatitis, epididymitis, gastrointestinal infections, bone and joint infections, cystic fibrosis, skin infections, post-operative wound infections, abscesses, phlegmon, wound infections, infected burns, scalds, infections in the oral region, infections after dental operations, ostgeomyelitis, septic arthritis, cholecystitis, peritonitis with appendicitis, cholangitis, intra-abdominal abscesses, pancreatitis, sinusitis, mastoiditis, mastitis, tonsillitis, typhus, meningitis and infections of the nervous systems, salpingitis, endometritis, genital infections, pelviperitonitis and eye infections.

In addition to humans, bacterial infections can also be treated in other species. Examples which may be mentioned are:

pig: coli-diarrhoea, enterotoxaemia, sepsis, dysentery, salmonellosis, metritis-mastitis-agalactia syndrome, mastitis; ruminants (cow, sheep, goat): diarrhoea, sepsis, bronchopneumonia, salmonellosis, pasteurellosis, mycoplasmosis, genital infections;

horse: bronchopneumonia, joint-ill, puerperal and postpuerperal infections, salmonellosis;

dog and cat: bronchopneumonia, diarrhoea, dermatitis, otitis, urinary infection, prostatitis;

poultry (hen, turkey, quail, pigeon, ornamental birds, others): mycoplasmosis, *E. coli* infections, chronic airway diseases, salmonellosis, pasteurellosis, psittacosis.

Bacterial diseases in the rearing and keeping of productive and ornamental fish can likewise be treated, where the antibacterial spectrum is widened beyond the previously mentioned pathogens to further pathogens such as, for example, pasteurella, brucella, campylobacter, listeria, erysipelothrix, corynebacteria, borellia, treponema, nocardia, rikettsia and yersinia.

In the following table, the minimum inhibitory concentrations (MIC values, μg/ml) are given for Examples 1, 3 and 4 in comparison with piperacillin. The MIC values are determined by the agar dilution test with the aid of a multipoint inoculator, the reading taking place after 18 to 24 hours' incubation at 37° C. Isosensitest agar is used as the growth medium.

| Bacteria | Example 1 | Example 3 | Example 4 | Piperacillin |
|---|---|---|---|---|
| E. coli T7 | 32 | >128 | 128 | 128 |
| E. coli A261 | 16 | 16 | 32 | 16 |
| E. coli Neum. | 0,5 | 0,125 | <0,06 | 0,125 |
| E. coli 183/58 | 4 | 32 | 2 | 0,5 |
| E. coli F14 | >128 | >128 | >128 | >128 |
| E. coli C165 | 0,5 | 0,5 | 0,25 | 0,5 |
| E. coli 4322 | 0,5 | 0,25 | 0,125 | 0,25 |

-continued

| Bacteria | Example 1 | Example 3 | Example 4 | Piperacillin |
|---|---|---|---|---|
| Klebs. 57. USA | 16 | 128 | 16 | 16 |
| Klebs. 63 | 1 | 2 | 0,5 | 0,5 |
| Klebs. 1852 | 16 | >128 | 64 | 64 |
| Klebs. 6097 | 2 | 8 | 1 | 1 |
| Serratia 16001 | 16 | 2 | 1 | 1 |
| Serratia 16002 | 8 | 4 | 1 | 2 |
| Provid. 12012 | 8 | 8 | 2 | 1 |
| Prot. morg. 932 | 32 | 4 | 16 | 4 |
| Prot. vulg. 9023 | 4 | 1 | 1 | 0,5 |
| Prot. vulg. 1017 | 32 | 2 | 4 | 4 |
| Prot. vulg N6 | 1 | 0,25 | 0,5 | 0,25 |
| Prot. rettg. 10007 | 2 | 1 | 0,25 | 0,25 |
| Prot. mir. 1235 | 2 | 0,25 | 0,25 | <0,06 |
| Staph. 1756 | 32 | 64 | 64 | 128 |
| Staph. 133 | 1 | 0,5 | 0,5 | 0,5 |
| Staph. 25455 | 2 | 1 | 2 | 2 |
| Staph. 25470 | >128 | 64 | 64 | 128 |
| Staph. E 25185 | 1 | 1 | 0,25 | 0,5 |
| Strept. faec 27101 | 128 | 32 | 32 | 32 |
| Strept. faec 113 | 8 | 2 | 2 | 2 |
| Enterococc. 9790 | 16 | 8 | 8 | 8 |
| Enterococc. 27158 | 4 | 4 | 4 | 4 |
| Psdm. F41 | 2 | 2 | 8 | 8 |
| Psdm. Walter | 2 | 2 | 8 | 8 |
| Psdm. 7035 | 2 | 2 | 4 | 8 |
| Psdm. 7451 | 8 | 4 | 8 | 16 |
| Enterob. cl. 5605 | >128 | >128 | 64 | 32 |
| Enterob. Cl. 5744 | 2 | 32 | 4 | 4 |
| Acinetob. 14061 | 4 | 4 | 2 | 8 |

The present invention includes pharmaceutical preparations which contain one or more active compounds according to the invention or which consist of one or more active compounds according to the invention in addition to non-toxic, inert pharmaceutically suitable excipients.

The present invention also includes pharmaceutical preparations in dosage units. This means that the preparations are in the form of individual portions, for example tablets, dragees, capsules, pills, suppositories and ampoules, whose active compound content corresponds to a fraction or a multiple of an individual dose. The dosage units may contain, for example, 1, 2, 3 or 4 individual doses or ½, ⅓ or ¼ of an individual dose. An individual dose preferably contains the amount of active compound which is administered in one application and which usually corresponds to a whole, a half, a third or a quarter of a daily dose.

Non-toxic, inert pharmaceutically suitable excipients are taken to mean solid, semi-solid or liquid diluents, fillers or formulation auxiliaries of any type.

Preferred pharmaceutical preparations which may be mentioned are tablets, dragees, capsules, pills, granules, suppositories, solutions, suspensions and emulsions, pastes, ointments, gels, creams, lotions, powders or sprays.

Tablets, dragees, capsules, pills and granules may contain the active compound(s) in addition to the customary excipients, such as (a) fillers and extenders, for example starches, lactose, sucrose, glucose, mannitol and silica, (b) binders, for example carboxymethylcellulose, alginates, gelatin, polyvinylpyrrolidone, (c) humectants, for example glycerol, (d) disintegrants, for example agar-agar, calcium carbonate and sodium bicarbonate, (e) solution retardants, for example paraffin and (f) absorption accelerators, for example quaternary ammonium compounds, (g) wetting agents, for example cetyl alcohol, glycerol monostearate, (h) adsorption agents, for example kaolin and bentonite and (i) lubricants, for example talc, calcium stearate and magnesium stearate and solid polyethylene glycols or mixtures of the substances mentioned under (a) to (i).

The tablets, dragees, capsules, pills and granules may be provided with the customary coatings and shells containing, if appropriate, opacifying agents and can be so composed that they release the active compound(s), if appropriate with a delay, only or preferably in a certain part of the intestinal tract, in which case, for example, polymeric substances and waxes can be used as embedding materials.

If appropriate, the active compound(s) may also be present in micro-encapsulated form with one or more of the abovementioned excipients.

In addition to the active compound(s), suppositories may contain the customary water-soluble or water-insoluble excipients, for example polyethylene glycols, fats, for example cocoa fat and higher esters (for example $C_{14}$-alcohol with $C_{16}$-fatty acid) or mixtures of these substances.

Ointments, pastes, creams and gels may contain the customary excipients in addition to the active compound(s), for example animal and vegetable fats, waxes, paraffins, starch, tragacanth, cellulose derivatives, polyethylene glycols, silicones, bentonites, silica, talc and zinc oxide or mixtures of these substances.

Powders and sprays may contain the customary excipients in addition to the active compound(s), for example lactose, talc, silica, aluminum hydroxide, calcium silicate and polyamide powder or mixtures of these substances. Sprays may additionally contain the customary propellants, for example chlorofluorohydrocarbons.

Solutions and emulsions may contain the customary excipients, such as solvents, solubilizers and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, corn germ oil, olive oil, castor oil and sesame oil, glycerol, glycerol formal, tetrahydrofurfuryl alcohol, polyethylene glycols and fatty acid esters of sorbitan or mixtures of these substances in addition to the active compound(s).

For parenteral administration, the solutions and emulsions may also be present in sterile and blood-isotonic form.

Suspensions may contain the customary excipients, such as liquid diluents, for example water, ethyl alcohol, propylene glycol, suspending agents, for example ethoxylated isostearyl alcohols, polyoxyethylene sorbitol and sorbitan esters, microcrystalline cellulose, aluminum metahydroxide, bentonite, agar-agar and tragacanth or mixtures of these substances in addition to the active compound(s).

The said formulation forms may also contain colorants, preservatives and also odor -improving and flavor-improving additives, for example peppermint oil and eucalyptus oil and sweeteners, for example saccharine.

The therapeutically active compounds should preferably be present in the abovementioned pharmaceutical preparations in a concentration of about 0.1 to 99.5, preferably 0.5 to 95% by weight, of the total mixture.

The abovementioned pharmaceutical preparations may also contain further pharmaceutical active compounds in addition to the active compounds according to the invention.

The preparation of the abovementioned pharmaceutical preparations takes place in a customary manner by known methods, for example by mixing the active compounds(s) with the excipient(s).

The preparations mentioned may be used in humans and animals either orally, rectally, parenterally (intravenously, intramuscularly, subcutaneously), intracisternally, intravaginally, interperitoneally, locally (powders, ointments, drops) and for the therapy of infections in hollow spaces and body cavities. Suitable preparations are injection solutions, solutions and suspensions for oral therapy, gels, pour on formulations, emulsions, ointments or drops. For local therapy, ophthalmological and dermatological formulations, silver salts and other salts, ear drops, eye ointments, powders or solutions may be used. In animals, the administration may also take place in suitable formulations via the feed or drinking water.

Furthermore, gels, powders, tablets, delayed-release tablets, premixes, concentrates, granules, pellets, tablets, boli, capsules, aerosols, sprays and inhalants may be used in human$ and animals. Furthermore, the compounds according to the invention may be incorporated into other excipients such as, for example, plastics, (plastic chains for local therapy), collagen or bone cement.

In general, it has proved advantageous both in human and veterinary medicine to administer the active compound(s) in total amounts of about 0.5 to about 500, preferably 5 to 100 mg/kg of body weight every 24 hours, if appropriate in the form of several individual doses, to attain the desired results. An individual dose preferably contains the active compound(s) in amounts of about 1 to about 80, in particular 3 to 30 mg/kg of body weight. However, it may be necessary to depart from the dosages mentioned, depending on the type and the body weight of the subject to be treated, the nature and severity of the disase, the type of composition and the administration of the medicament and also the time period or interval within which the administration takes place.

Thus in some cases it may be necessary to manage with less than the abovementioned amount of active compound, whereas in other cases the abovementioned amount of active compound must be exceeded. The optimum dosage required in each case and the type of administration of the active compound can easily be established by one skilled in the art on the basis of his expert knowledge.

The new compounds may be given in the customary concentrations and preparations together with the feed or feed preparations or with the drinking water. Infection by gram negative or gram positive bacteria can thus be prevented, improved and/or cured and promotion of growth and an improvement in the utilization of the feed can thus be achieved.

The compounds according to the invention may be combined with other antimicrobial active compounds and lactamase inhibitors, for example with penicillins which are particularly resistant to penicillinase and clavulanic acid for the purpose of widening the spectrum of action and in order to attain an increase in action, specifically in $\beta$-lactamase-forming bacteria. Such a combination is, for example, that with oxacillin or dicloxacillin.

The compounds according to the invention may also be combined with aminoglycoside antibiotics, such as, for example, gentamicin, sisomicin, kanamicin, amikacin or tobramycin, for the purpose of widening the spectrum of action and in order to achieve an increase in action.

PREPARATION EXAMPLES

The invention is further illustrated by the following examples.

EXAMPLE 1

Sodium D-7-[α-(4-ethyl-2,3-dioxo-1-piperazino-carbonylamino)-α-(2-aminobenzothiazol-6-yl)glycylamido]-3-(1-methyl-1H-tetrazol-5-yl-thiomethyl)-3-cephem-4-carboxylate

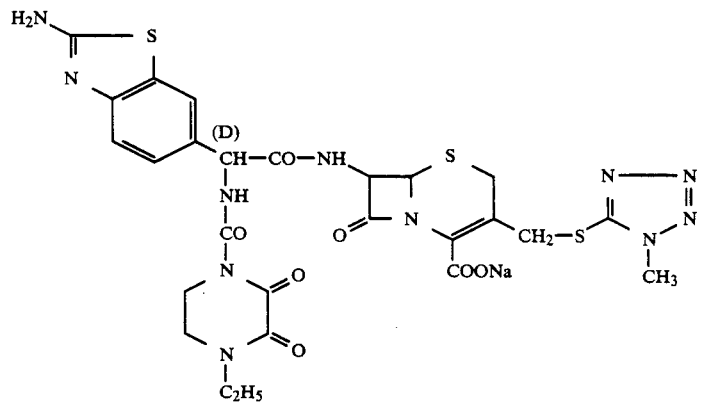

(a) D-7-[2-(aminobenzothiazol-6-yl)glycyl-amidoj-3-(1-methyl-1H-tetrazol-5-yl-thiomethyl)-3-cephem-4-carboxylic acid Activation of the precursor acid:

5 g (0.0155 mol) of D-α-t-butyloxycarbonylamino-α-(2-aminobenzothioazol-6-yl)acetic acid are dissolved in 25 ml of dimethylformamide in the presence of 2.69 ml (0.0155 mol) of ethyldiisopropylamine at room temperature, 1.20 ml (0.0155 mol) of mesyl chloride are added dropwise at −50° C. and the mixture is stirred at −50° C. for 40 minutes.

Preparation of the amino component:

5.96 g (0.0155 mol) of t-butyl 7-amino-3-(1-methyl-1H-tetrazol-5-yl-thiomethyl)-3-cephem-4-carboxylate are dissolved in 15 ml of tetrahydrofuran and 20 ml of methylene chloride, 2.69 ml (0.0155 mol) of ethyldiisopropylamine are added at room temperature and the product is injected into the mesylate of the precursor acid at −50° C.

Coupling and isolation

After addition of the amine solution the mixture is stirred for 15 minutes more at −50° C.; the temperature is then allowed to climb to 20° C. in 35 minutes without a cooling bath. The reaction solution is stirred into 100 ml of water/800 ml of ethyl acetate, the aqueous phase is separated off and the organic phase is washed three times with 100 ml each of 0.2N HCl, twice with 100 ml each of NaHCO3 solution and finally with sodium chloride solution. After drying and evaporating the ethyl acetate phase, the residue is taken up in 200 ml of trifluoroacetic acid (TFA)/methylene chloride (1:1) and stirred at room temperature for 1 hour. The trifluoroacetic acid/methylene chloride mixture is subsequently removed by distillation in vacuo and ether is added to the oily residue. The trifluoroacetate is filtered off with suction, washed with ether and dried.

Yield: 7.6 g

The trifluoroacetate salt is substantially brought into solution in 500 ml of water and 40 ml of glacial acetic acid by means of an ultrasound bath. The solution is added to a column containing 100 ml of Amberlite IRA-68 (acetate form), washed with 1000 ml of 10% strength acetic acid and lyophilized.

Yield: 5 g

The lyophilizate is dissolved in 30 ml of 50% strength acetic acid and chromatographed on a Whatman column (Magnum 500×40, partisil $C_{18}$, 50 μm) first with 3% strength acetic acid and then with 3% acetic acid with the addition of 10% acetonitrile. Yields: 1st fraction—HPLC purity: 69%. 2nd fraction—

HPLC purity: 95.2%.

Hibar 250-4, RP-8, 10 μm,

Eluent: 1000 ml of water/30 ml of acetic acid, 254 nm, 2 ml/min.

Retention 9.14

$C_{19}H_{19}N_9O_4S_3 \times 2H_2O \times CH_3COOH$ (629.64) Calc.: C 40.06, H 4.32, N 20.02, S 15.27. Found: C 40.4, H 4.1, N 19.7, S 15.3.

NMR (DCOOD): δ=3.64 (d, 1H); 3.78 (d, 1H); 4.09 (s, 3H); 4.24 (d, 1H); 4.46 (d, 1H); 5.22 (d, 1H); 5.74 (s, 1H); 5.92 (d, 1H); 7.84 (s, 2H); 8.14 (s, 1H) ppm.

(b) Sodium D-7-[α-(4-ethyl-2,3-dioxo-1-piperazino-carbonylamino)-α-(2-aminobenzothiazol-6-yl)glycylamido]-3-(1-methyl-1H-tetrazol-5-yl-thiomethyl)-3-cephem-4-carboxylate 2 g (3.17 mmol; purity 69%) of 1a are suspended in 120 ml of tetrahydrofuran/water (80:20) which is cooled to 5 to 10° C. using an ice bath and the pH is adjusted to 8.0 with stirring using triethylamine by means of an autotitrator (Memo Titrator DL 40, Mettler). 4-Ethyl-2,3-dioxo-1-piperazinocarbonyl chloride - dissolved in 60 ml of tetrahydrofuran—is added dropwise to the clear solution obtained. The pH value is kept at pH 7.5 by means of the Memo titrator by the suitable addition of 10% strength triethylamine in tetrahydrofuran. During the 90 minutes' further stirring 100 ml more of water are added in several portions. The reaction solution is subsequently diluted using about 200 ml of water and 600 ml of ethyl acetate, the pH is adjusted to 2.5 and the ethyl acetate phase is separated off. After washing the organic phase with sodium chloride solution, drying over sodium sulphate and concentrating to dryness, 1.15 g (71.0 % of theory) are obtained. The material is chromatographed on a preparative column (Hibar 250-25, RP 18, 7 μm) (see Example 2b) changing the eluent system to water/acetonitrile having a gradient of 2% to 20%.

Yield: 550 mg (34% of theory)
$C_{26}H_{27}N_{11}O_7S_3 \times 2H_2O$ (737.8)
Calc.: C 42.33, H 4.24, N 20.88, S 13.04.
Found: C 41.9, H 4.1, N 20.15, S 13.8.

EXAMPLE 2

Sodium D-7-[α-(4-ethyl-2,3-dioxo-1-piperazino-carbonylamino)-α-(2-aminobenzothiazol-6-yl)glycylamido]-3-acetoxymethyl-3-cephem-4-carboxylate

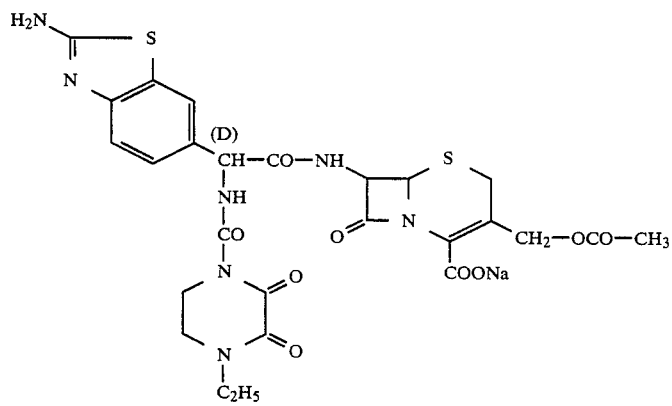

(a) D-7-[(2-Aminobenzothiazol-6-yl)glycylamido]-3-acetoxymethyl-3-cephem-4-carboxylic acid 1.62 g (5 mmol) of D-α-t-butyloxycarbonylamino-α-(2-aminobenzothiazol-6-yl)acetic acid are dissolved in 12 ml of dimethylformamide at room temperature in the presence of 0.871 ml (5 mmol) of ethyldiisopropylamine, 0.387 ml (5 mmol) of mesyl chloride is added dropwise at −50° C. and the mixture is stirred at −50° C. for 40 minutes.

Preparation of the amino component:
1.64 g (5 mmol) of t-butyl 7-amino-3-acetoxymethyl-3-cephem-4-carboxylate are dissolved in 12 ml of methylene chloride, 0.871 ml (5 mmol) of ethyldiisopropylamine are added at room temperature and the product is immediately poured into the mesylate of the precursor in a stream.

Coupling and isolation
After addition of the amine solution the mixture is stirred at −50° C. for 15 minutes more in the cooling bath. The temperature is then allowed to climb to 0° C. during the course of 45 minutes. The reaction solution is stirred into 400 ml of ethyl acetate/200 ml of water, the aqueous phase is separated off and the organic phase is washed twice with 0.2N HCl. Methanol is added in order to obtain a better phase separation. The organic phase is then washed twice with saturated NaHCO₃ solution and sodium chloride solution, dried and concentrated to dryness. The residue is treated for 20 minutes at room temperature with 50 ml of trifluoroacetic acid and 0.5 ml of anisole. The trifluoroacetic acid is then concentrated to dryness, the oily residue is triturated with ether and the trifluoroacetate salt is filtered off with suction.

Yield: 1.56 g

The trifluoroacetate is dissolved in water/acetic acid (30 ml, 1:1) and chromatographed on adsorber resin HP 20 (500 ml, dianion, Mitsubishi). The resin is eluted using water to which a continuously increasing content of acetonitrile (0% to 40%) and acetic acid (0% to 40%) is added. A total of 10 x 400 ml fractions are collected, fractions 6 and 7 containing the desired compound.

Yield: 473 mg (16.5 % of theory).
$C_{19}H_{19}N_5O_6S_2 \times 2H_2O \times CH_3COOH$ (573.56)
Calc.: C 43.98, H 4.74, N 12.21.
Found: C 43.5, H 4.5, N 12.5.

NMR (DCOOD): δ=2.16 (s, 3H); 3.45 (d, 1H); 3.68 (d, 1H); 4.96 (d, 1H); 5.17 (d, 1H); 5.20 (d, 1H); 5.71 (s, 1H); 5.92 (d, 1H); 7.78 (s, 2H); 8.1 (s, 1H) ppm.

HPLC purity: 95.5%; Hibar 250-4, RP-8, 10 μm; eluent: 1000 ml H₂O/40 ml CH₃CN/1 ml TFA, 254 nm; 4 ml/min; retention: 2.33

(b) Sodium D-7-[α-(4-ethyl-2,3-dioxo-1-piperazinocarbonylamino)-α-(2-aminobenzothiazol-6-yl)glycylamido]-3-acetoxymethyl-3-cephen-4-carboxylate 0.573 g (1 mmol) of 2a are suspended in 30 ml of tetrahydrofuran/water, cooled to 5° C. to 10° C. using an ice bath and adjusted to pH 8.0 with magnetic stirring using triethylamine by means of an autotitrator. 0.307 g (1.5 mmol) of 4-ethyl-2,3-dioxo-1-piperazinocarbonyl chloride in 20 ml of tetrahydrofuran are added dropwise to the clear solution obtained. The pH is kept at 7.5 by suitable addition of 10% strength triethylamine in tetrahydrofuran. During the subsequent stirring (90 minutes), 30 ml more of water are added. The reaction solution is now diluted with 50 ml of water/400 ml of ethyl acetate, the pH is adjusted to 2.5 and the mixture is extracted with ethyl acetate. After washing with sodium chloride solution, drying over magnesium sulphate and concentrating the organic phase, 200 mg of crude product are obtained. The aqueous phase from the ethyl acetate extraction is adjusted to pH 5 and lyophilized(yield: 24.8 g). Both substances are dissolved in 60 to 70 ml of 10% strength acetic acid (ultrasound bath), insoluble material is filtered off with suction, the filtrate is filtered once more through a Millipore filter and chromatographed on a Whatman column (Magnum 500×40 mm, partisil C₁₈, 50 μm), first using 2000 ml of 3% strength acetic acid, then 3% strength acetic acid with an increasing gradient of acetonitrile of 10% to 20% as the eluent. The desired compound is eluted using 3% strength acetic acid with the addition of 20% acetonitrile.

Yield: 187 mg

Since the eluted compound contains the 6β isomer as a by-product, the entire material is chromatographed once more on a Merck column (Hibar 250-25, RP-18, 7 μm) using the eluent 900 ml water/100 ml acetonitrile/10 ml glacial acetic acid.

Yield: 36 mg

HPLC purity: 88.8%, Hibar 250-4, RP 8, 10 μm,

Eluent: 100 ml of acetonitrile/1000 ml of water 254 nm, 2 ml/min. Retention: 5.33

NMR (DMSO): δ=1.1 (t, 3H); 2.02 (s, 3H); 3.34–3.48 (q, 2H); 3.56 (broad s, 2H); 3.9 (broad s, 2H); 4.65 (d, 1H); 4.96 (d, 1H); 5.02 (d, 1H); 5.62 (d, 1H); 5.72–5.78 (q, 1H); 7.27 (s, 2H); 7.51 (s, 2H); 7.64 (s, 1H); 9.42 (d, 1H); 9.82 (d, 1H) ppm.

EXAMPLE 3

Sodium D-6-[α-(4-ethyl-2,3-dioxo-1-piperazino-carbonylamino)-α-(2-aminobenzothiazol-6-yl)-glycylamido]-penicillanate

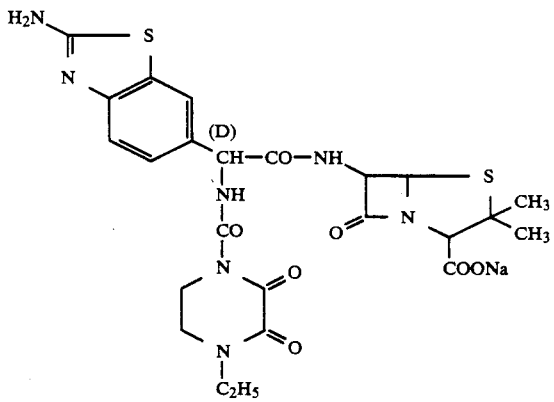

(a)
D-α-[(4-Ethyl-2,3-dioxo-piperazin-1-yl)-carbonylamino]-α-(2-aminobenzothiazol-6-yl)acetic acid A suspension of 12 g (0.0538 mol) of D-α-amino-α-(2-aminobenzothiazol-6-yl)acetic acid in 100 ml of tetrahydrofuran (THF) and 40 ml of water is brought into solution by gradual addition of 1N sodium hydroxide up to a pH of 10.5 and cooled to +5° C. to +10° C. 14.3 g (0.0699 mol) of 4-ethyl-2,3-dioxo-1-piperazinocarbonyl chloride dissolved in 80 ml of tetrahydrofuran are added dropwise to the solution. During this time, the pH of the reaction solution is kept at 7.5 to 8.0 by addition of 2N sodium hydroxide. The mixture is subsequently stirred for 2 hours more at room temperature, the pH of the solution is readjusted to 5.0 and the solution is layered onto a column filled with adsorber resin HP 20. Elution takes place using water and 50% strength acetone. The eluate, which contains the desired compound, is lyophilized.

Yield: 12.8 g (58.2% of theory)
$C_{16}H_{17}N_5O_4S \times H_2O$ (409.42)

NMR (DMSO): δ=1.08 (t, 3H); 3.32–3.44 (q, 2H); 3.56 (m, 2H); 3.9 (m, 2H); 5.32 (d, 1H); 7.2 (dd, 1H); 7.26–7.33 (t, 1H); 7.55 (s, 2H); 7.66 (weak d, 1H) ppm.

(b) Sodium D-6-[α-(4-ethyl-2,3-dioxo-1-piperazinocarbonylamino]-α-(2-aminobenzothiazol-6-yl)glycylamido]-penicillanate (mesyl chloride activation)

2.5 g (0.0061 mol) of 3a are activated in DMF at −50° C. analogously to Example 2a using 1.06 ml (0.0061 mol) of ethyldiisopropylamine and 0.472 ml (0.0061 mol) of mesyl chloride and brought to reaction with 3.47 g (0.00671 mol) of D-6-(2-aminobenzothiazol-6-glycylamido)-penicillanic acid acetate dihydrate.

$C_{24}H_{26}N_7NaO_7S_2 \times H_2O$ (629.65)

Yield: 1.6 g (41.7% of theory)

NMR (DMSO): δ=1.1 (t, 3H); 1.50 (s, 3H); 1.54 (s, 3H); 3.25–3.45 (q, 2H); 3.55 (m, 2H); 3.9 (m, 2H); 4.18 (s, 1H); 5.38 (d, 1H); 5.54 (q, 1H); 5.71 (d, 1H); 7.26 (t, 1H); 7.51 (s, 1H); 7.65 (s, 1H); 9.27 (d, 1H); 9.84 (d, 1H) ppm.

(c) Sodium D-6-[α-(4-ethyl-2,3-dioxo-1-piperazinocarbonylamino)-α-(2-aminobenzothiazol-6-yl)glycylamido]-penicillanate (acid chloride process)

0.220 mg (0.425 mmol) of D-6-(2-aminobenzothiazol-6-yl-glycylamido)-penicillanic acid as the acetate dihydrate (MW=517.59) are suspended in 10 ml of 80% strength aqueous tetrahydrofuran and brought into solution at pH 8.5 by means of a 10% strength solution of triethylamine in tetrahydrofuran. 0.174 g (0.85 mmol) of 4-ethyl-2,3-dioxo-1-piperazinocarbonyl chloride dissolved in 2 ml of tetrahydrofuran are added at 0° C. to +5° C. during the course of 20 minutes, the pH being kept at 7.5 by suitable addition of triethylamine in tetrahydrofuran. The mixture is stirred for a further 90 minutes at pH 7.5, 100 ml of water are subsequently added and tetrahydrofuran is substantially removed by distillation in vacuo. The aqueous solution remaining is lyophilized. 500 mg of lyophilizate are obtained which are dissolved in 6 ml of water, filtered through an ultrafilter and subsequently chromatographed on a preparative HPLC column (Hibar 250-25, RP 18, 7 μm) by means of 5% strength acetonitrile in water.

Yield: 165 mg

The entire material is subsequently dissolved in 50 ml of water by the addition of sodium hydrogen carbonate solution for the removal of the triethylamine, pumped onto a Merck column (Hibar 250-25, 1 RP 18, 7 μm) and then eluted using 100 ml of 0.1N hydrochloric acid and 700 ml of water. The column is subsequently turned round and the substance is washed from the column using 30% strength acetonitrile.

Yield: 120 mg (40.5% of theory)
$C_{24}H_{27}N_7O_7S_2 \times 6H_2O$ (697.752)

HPLC purity: 96.6%, Hibar 250-4, RP-8, 10 μm, Eluent: 0.05 molar ammonium acetate solution (1000 ml)/100 ml of acetonitrile, 254 nm, 3 ml/min. Retention: 9.88

NMR (DMSO): δ=1.1 (t, 3H); 1.49 (s, 3H); 1.51 (s, 3H); 3.25–3.42 (q, 2H); 3.55 (m, 2H); 3.9 (m, 2H); 4.18 (s, 1H); 5.38 (d, 1H); 5.52 (q, 1H); 5.7 (d, 1H); 7.28 (t, 1H); 7.51 (s, 1H); 7.65 (s, 1H); 9.27 (d, 1H); 9.83 (d, 1H) ppm.

EXAMPLE 4

Sodium D-6-[α-(2-oxo-3-furylideneamino-imidazolidin-1-yl-carbonylamino)-α-(2-aminobenzothiazol-6-yl)-glycylamido]-penicillanate

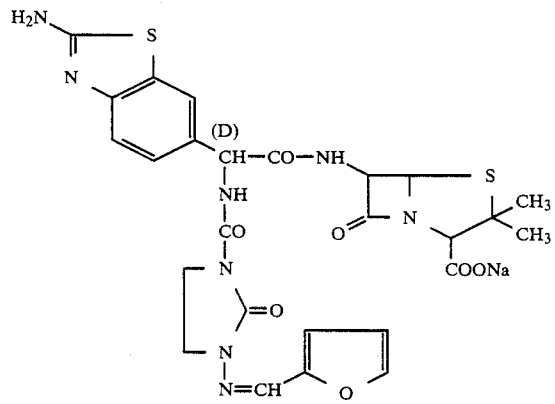

(a)

D-α-[(2-Oxo-3-furylideneamino-imidazolin-1-yl)carbonylamino]-α-(2-aminobenzothiazol-6-yl)acetic acid A suspension of 20 g (0.0896 mol) of D-α-amino-α-(2-aminobenzothiazol-6-yl)acetic acid in 200 ml of tetrahydrofuran and 120 ml of water is brought into solution by gradual addition of 2N sodium hydroxide up to a pH of 8.0. 23.8 g (0.0986 mol) of 1-chlorocarbonyl-2-oxo-3-furylideneamino-imidazolidine are subsequently introduced into the solution in portions at 5° C., the pH being simultaneously kept up at between 7.5 and 7.8 by addition of 1N sodium hydroxide. The mixture is stirred for about 2 hours more without cooling and 80 ml of tetrahydrofuran and 80 ml of water are added in small portions during the subsequent stirring. A clear solution gradually results, which is diluted using 200 ml of water and removed from tetrahydrofuran in vacuo. The remaining solution is extracted once using ethyl acetate and the aqueous phase is acidified to pH 2.0 at 0° C. with 2N hydrochloric acid. The precipitated product is filtered off with suction, washed with water and dried in vacuo.

Yield: 24.1 g (55.8% of theory)
$C_{18}H_{16}N_6O_5S \times 3\ H_2O$ (482.474)
Calc.: C 44.81, H 4.60, N 17.42, S 6.64.
Found: C 43.7, H 3.9, N 17.1, S 7.1.
NMR (DMSO): δ=3.78 (broad s, 4H); 5.38 (d, 1H); 6.66 (dd, 1H); 6.85 (d, 1H); 7.35 (dd, 1H); 7.45-7.52 (t, 1H); 7.75 (s, 1H); 7.83 (s, 2H); 8.85 (broad s, 2H); 9.08 (d, 1H) ppm.

(b) Sodium D-6-[α-(2-oxo-3-furylideneamino-imidazolidin-1-ylcarbonylamino)-α-(2-aminobenzothiazol-6-yl)glycylamido]-penicillanate Activation of the precursor acid 9.29 g (0.02 mol) of 4a (dihydrate) are dissolved in 40 ml of dimethylformamide, 2.8 ml (0.02 mol) of triethylamine are added, 4 drops of 3-dimethylamino-1-propanol and 1.92 ml (0.02 mol) of ethyl chloroformate are added at −50° C. and the mixture is stirred for 15 minutes at −40° C.

Preparation of the amino components:

4.54 g (0.021 mol) of 6-aminopenicillanic acid (6-APA) are suspended in 15 ml of water and brought into solution by dropwise addition of 2N sodium hydroxide. The solution resulting at room temperature is cooled to −10° C. and diluted using 20 ml of acetone.

Coupling and isolation

The cooled solution of 6-aminopenicillanic acid is added in a stream to the solution of the mixed anhydride of the precursor acid (a) at −50° C. and then stirred for 20 minutes without cooling, the temperature of the reaction solution gradually being increased to +5° C. The reaction solution is then stirred into 400 ml of ice water, the pH is adjusted to 2.0, and the precipitated product is filtered off with suction, washed with $H_2O$ and dried overnight in vacuo over phosphorus pentoxide.

Crude yield: 10.5 g

The material is dissolved in 50 ml of 5% strength acetonitrile with the addition of 60 ml of saturated sodium hydrogen carbonate solution (pH 8.6), filtered over silica gel and eluted on a Whatman column (Magnum M 40, 500×40, Merck filling material RP 18, 40–68 μm) using water with the addition of acetonitrile with an increasing gradient of 5% to 10% (flow rate: 40 ml/min).

Yield: 3.3 g (22.9% of theory)
$C_{26}H_{25}N_8NaO_7S_2 \times 4H_2O$ (720.723) Calc.: C 43.33, H 4.61, N 15.55, S 8.89, Na 3.18. Found: C 43.5, H 4.7, N 15.6, S 8.7, Na 3.0.

NMR (DMSO) δ=1.40 (s, 3H); 1.52 (s, 3H); 3.68-3.87 (m, 4H); 3.9 (s, 1H); 5.3 (d, 1H); 5.4-5.46 (q, 1H); 5.74 (d, 1H); 6.62 (d, 1H); 6.85 (d, 1H); 7.29 (t, 2H); 7.52 (s, 2H); 7.65 (s, 1H); 7.73 (s, 1H); 7.83 (s, 1H); 9.08 (d, 1H); 9.19 (d, 1H) ppm.

HPLC purity: 92.4%, Hibar 250-4, RP 8, 10 μm, Eluent: 800 ml of $H_2O$/200 ml of $CH_3N$/3.84 g of $CH_3COONH_4$ 254 nm, 4 ml/min. Retention: 3.69

EXAMPLE 5

Sodium D-6-[α-(imidazolidin-2-on-1-ylcarbonylamino)-α-(2-amino-benzothiazol-6-yl)glycylamido]-penicillanate

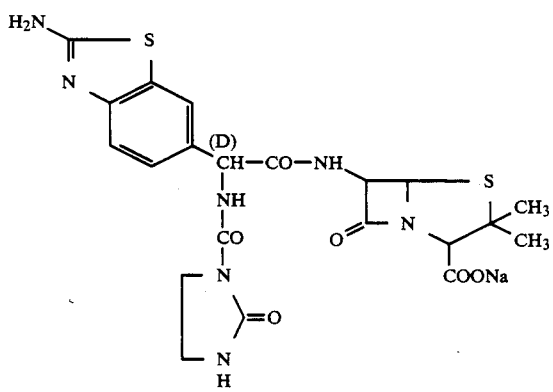

9.4 g (0.0223 mol) of D-6-(2-aminobenzothiazol-6-yl-glycylamido)penicillanic acid are suspended in 110 ml of 80% strength aqueous tetrahydrofuran and sufficient triethylamine is added with stirring at +20° C. so that a clear solution just results and the pH is between 7.5 and 8.2. The mixture is cooled to 0° C. and 3.3 g (0.0223 mol) of N-chlorocarbonylimidazolidin-2-one dissolved in 20 ml of tetrahydrofuran are added dropwise with ice cooling and vigorous stirring during the course of 30 minutes, the pH being kept between 7.5 and 8.0 by simultaneously occurring addition of triethylamine. The mixture is stirred for 30 minutes at 0° C. and subsequently for as long at room temperature until addition of triethylamine is no longer necessary to maintain the pH value of 7.5. 100 ml of water are added and tetrahydrofuran is removed by distillation in vacuo. The aqueous solution remaining is washed once with ether, covered with a layer of 300 ml of ethyl acetate, cooled to 0° C. and acidified to pH 1.5–2.0 with stirring and ice cooling using 1N hydrochloric acid. The organic phase is separated off, the filtrate is extracted once more with 200 ml of ethyl acetate and the organic extracts are combined. After drying over sodium sulphate, 22 ml of a 1 molar solution of sodium 2-ethylhexanoate in methanol-containing ether are added; the solution is concentrated almost to dryness, the residual solution is taken up in 25 ml of methanol and 400 ml of ether are added. The precipitated product is filtered off with suction, washed with ether and dried.

Yield: 6.3 g (47.8 % of theory)

$C_{21}H_{22}N_7NaO_6S_2 \times 2H_2O$ (591.604)

Calc.: C 42.64, H 4.43, N 16.57, S 10.47.

Found: C 41.9, H 4.22, N 16.1, S 9.9.

NMR (DMSO): δ=1.41 (s, 3H); 1.54 (s, 3H); 3.68–3.87 (m, 4H); 4.0 (s, 1H); 5.3 (d, 1H); 5.4–5.46 (q, 1H); 5.72 (d, 1H); 7.29 (t, 2H); 7.68 (s, 1H); 9.08 (d, 1H); 9.19 (d, 1H) ppm.

EXAMPLE 6

Sodium D-6-[α-(3-methylsulphonyl-imidazolidin-2-on-1-yl-carbonylamino)-α-(2-aminobenzothiazol-6-yl)glycylamido]penicillanate 3.5 g (0.0083 mol) of D-6-(2-aminobenzothiazol-6-ylglycylamido)penicillanic acid are suspended in 50 ml of 80% strength tetrahydrofuran and brought into solution by just the necessary amount of triethylamine (pH 7.8). 1.94 g (0.0096 mol) of 1-chlorocarbonyl-3-methylsulphonyl- imidazolidin-2-one are added in portions with ice cooling and the pH value of 7.5 is maintained by simultaneously occurring addition of 10% strength triethylamine in tetrahydrofuran. The mixture is subsequently stirred for about 2 hours in a pH range from 7.0–7.5. The mixture is diluted using 150 ml of H₂O, the pH is adjusted to 6.5, tetrahydrofuran is substantially removed by distillation in vacuo and the remaining aqueous solution is washed once with ether.

The aqueous filtrate is covered with a layer of ethyl acetate and acidified to pH 2 at 0° C. to 5° C. using 1N hydrochloric acid. The organic phase is separated off, washed with sodium chloride solution, dried over sodium sulphate and the sodium salt is then isolated analogously to Example 5b by means of 1 molar sodium 2-ethylhexanoate solution.

Yield: 2.3 g (41.4% of theory)

$C_{22}H_{24}N_7NaO_8S_3 \times 2H_2O$ (669.69)

Calc.: C 39.46, H 4.21, N 14.64, Na 3.43, S 14.36.

Found: C 38.8, H 4.4, N 14.1, Na 3.6, S 13.9.

EXAMPLE 7

7β-{D-α-[(4-Ethyl-2,3-dioxopiperazin-1-yl)carbonylamino]-α-(2-amino-1H-benzimidazol-5-ylglycylamido}-7α-formamido-3-(pyridiniomethyl)-3-cephem-4-carboxylic acid

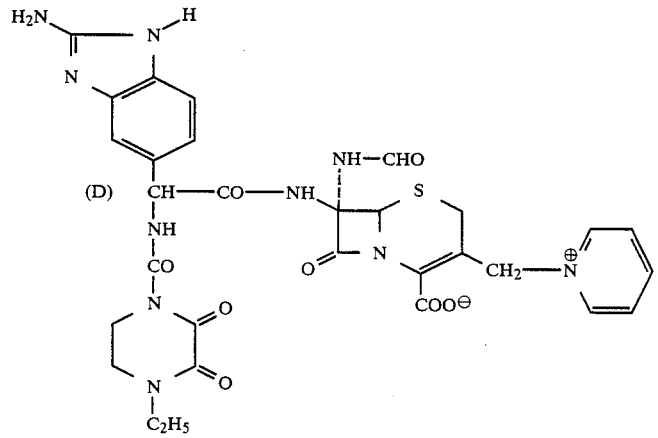

550 mg (1.05 mmol) of 7α-formamido-7β-[D-2-(amino-1H-benzimidazol-5-yl)glycylamido]-3-(pyridiniomethyl)-3-cephem-4-carboxylic acid are reacted analogously to Example 1b with 258 mg (1.26 mmol) of 4-ethyl-2,3-dioxo-1-piperazino-carbonyl chloride. After chromatography on adsorbent resin HP 20 AG (dianion, Mitsubishi) using water/acetone (1:0→10:1), 150 mg of betaine are obtained.

$C_{30}H_{30}N_{10}O_8S \times 2H_2O$ (762.72) Calc.: C 49.58, H 4.72, N 19.27, S 4.41. Found: C 48.9, H 4.6, N 18.7, S 4.2.

EXAMPLE 8

7β-{D-α-[4-Ethyl-2,3-dioxopiperazin-1-yl)carbonylamino]-α-(2-aminobenzoxazol-5-ylglycylamido}-7-α-formamido-3[(1,3,4-thiadiazol-2-yl)thiomethyl]-3-cephem-4-carboxylic acid

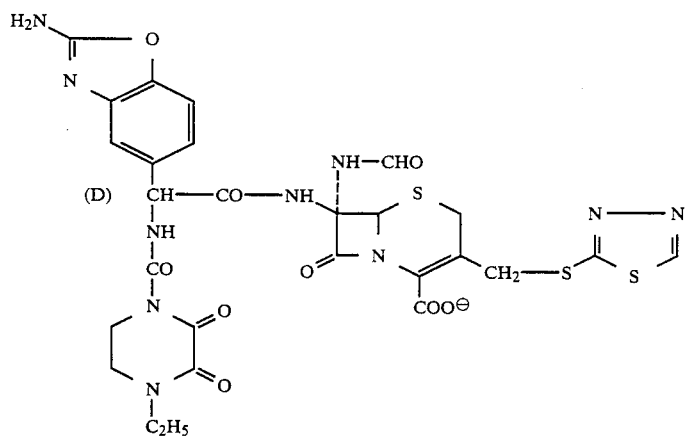

0.720 g (1.92 mmol) of D-α-[(4-ethyl-2,3-dioxopiperazin-1-yl)carbonylamino]-α-(2-aminobenzoxazol-5-yl)-acetic acid are treated at −50° C. for 40 minutes analogously to Example 2a with 0.334 ml (1.92 mmol) of ethyldiisopropylamine and 0.149 ml (1.92 mmol) of mesyl chloride and subsequently reacted with 0.788 g (2.11 mmol) of 7β-amino-7-α-formamido-3-[(1,3,4-thiadiazol-2-yl)thiomethyl]3-cephem-4-carboxylic acid. The crude betaine is chromatographed on adsorbent resin OC 1062 (Lewatite BAYER AG) using the eluent system: water/acetone (1:1→4:1). The eluate, which contains the desired compound is freed from acetone, adjusted to pH 7.8 using 1N sodium hydroxide and the solution islyophilized.

Yield: 310 mg (21.4% of theory)
$C_{27}H_{25}N_{10}NaO_9S_2 \times 2H_{20}$ (756.714)
Calc.: C 42.86, H 3.86, N 18.51, Na 3.04, S 8.47.
Found: C 41.9, H 3.5, N 18.2, Na 3.2, S 8.2.

It will be appreciated that the instant specification and claims are set forth by way of illustration and not limitation, and that various modifications and changes may be made without departing from the spirit and scope of the present invention.

EXAMPLE 9

D-7-[α-(4-ethyl-2,3-dioxo-1-piperazinocarbonylamino)-α-(benzofur-5-yl)glycylamido]-3-([1,2,5,6-tetrahydro-2-methyl-5,6-dioxo-as-triazin-3-yl)thio]methyl)-3-cephem-4-carboxylic acid disodium

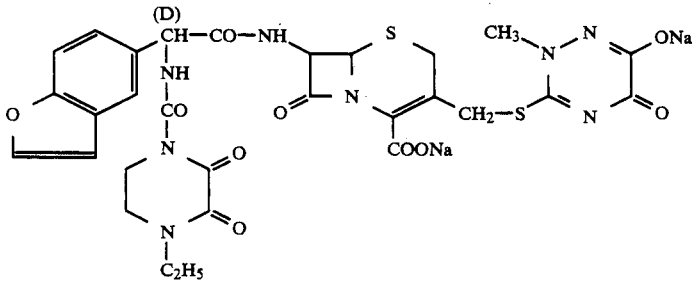

(a) Preparation of the precursor acid:

790 mg (2.2 mmol) of DL-α-[(4-ethyl-2,3-dioxo-1-piperazino)-carbonylamino]-α-(benzofur-5-yl) acetic acid were dissolved in 15 ml of dimethylformamide and 5 ml of acetonitrile with the addition of 0.31 ml (2.2 mmol) of triethylamine. Then the solution was cooled to −50° C. and 1 drop of 3-dimethylamino-1-propanol and 0.21 ml (2.2 mmol) of ethyl chloroformate were added in succession and the mixture is stirred for 30 mins. at −50° C.

(b) Preparation of the amine component 817 mg (2.2 mmol) of 7-amino-3-{[1,2,5,6-tetrahydro-2-methyl-5,6-dioxo-as-triazin-3-yl)-thio]methyl}-3-cephem-4-carboxylic acid were suspended in 10 ml of water, 10 ml of dimethylformamide and 4 ml of acetonitrile and the suspension was adjusted to a pH of 7,5 by adding 1N sodium hydroxide solution, whereupon a clear solution was formed.

(c) Coupling and isolation

After adding the amine component (b) to the solution of the mixed anhydride (a) at −50° C., the temperature of the solution was then allowed to rise to 0° C. (without a cold bath) within a period of 30 mins.

The the solution was partially evaporated diluted with about 100 ml of water and 300 ml of ethyl acetate, the pH value is adjusted to 2.5 and the ethyl acetate was separated oft. After washing the organic phase with sodium chloride solution, drying over sodium sulphate and concentrating to dryness the crude material was purified on a preparative column (Hibar 250-25, RP 18, 7 μm) using the mobile solvent system water/acetonitrile/glacial acetic acid (see Example 2b). The eluate, which contained the desired compound, was freed from organic solvent, adjusted to pH 75 with 1N sodium hydroxide solution and the solution was lyophilised.

Yield: 178 mg (10 % of theory)

$C_{29}H_{26}N_8Na_2O_{10}S_2$ $3H_2O$ (810.7) Calculated C 42.96, H 3.99, N 13.82 S 7.91. Found: C 41.2, H 3.5, N 13.62, S 6.89.

IR spectrum (Nujol): 1770, 1730, 1660 cm$^{-1}$.

EXAMPLE 10

D-7-[α-(-4-ethyl-2,3-dioxo-1-piperazino-carbonylamino)-α-(2-aminobenzothiazol-6-yl)-glycylamido]-3-{[1,2,5,6-tetrahydro-2-methyl-5,6-dioxo-as-triazin-3-yl)thio]methyl}-3-cephem-4-carboxylic acid disodium.

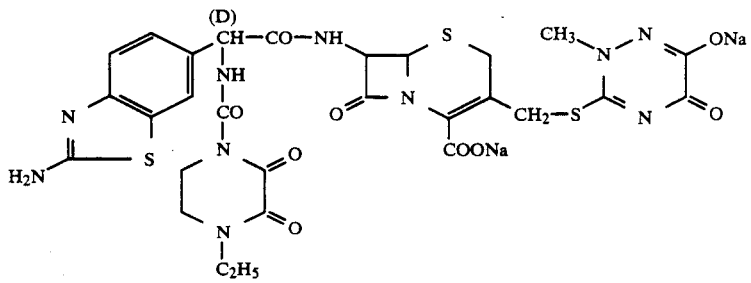

In analogy to Example 9 1.25 g (3.1 mmol) of D-α-[4-ethyl-2,3-dioxo-piperazinyl-1-yl)carbonylamino]-α-(2-aminobenzothiazol-6-yl) acetic acid monohydrate were activated with 0,434 ml (3.1 mmol) of triethylamine and 0.298 ml (3.1 mmol) of ethyl chloroformate at −50° C. and 1.15 g (3.1 mmol) of 7-amino-3-{[1,2,5,6,-tetrahydro-2-methyl-5,6-dioxo-cephemtriazin-3-yl)-thio]methyl]-3-cephem-4-carboxylic acid were then added. The crude product, which was isolated in analogy to Example 9, was dissolved in water with the addition of ammonium hydrogen carbonate and chromatographed on an adsorber resin LPG 4429 (Lewatit ® OC 1062) in aqueous acetone.

Yield: 0.95 g (38 % of theory)

$C_{28}H_{26}N_{10}Na_2O_9S_3$ $2H_2O$ (824.78) Calculated: C 40.78, H 3.67, N 16.98, S 11.66. Found: C 41.2, H 3.15, N 15.8, S 11.2.

IR Spectrum (KBr): 1775, 1740, 1695, 1670 cm$^{-1}$.

EXAMPLE 11

D-7-[α-(4-ethyl-2,3-dioxo-1-piperazinocarbonylamino)-α-(indol-5-yl)-glycylamido]-3-(1-methyl-1H-tetrazol-5-yl-thiomethyl)-3-cephem-4-carboxylic acid sodium

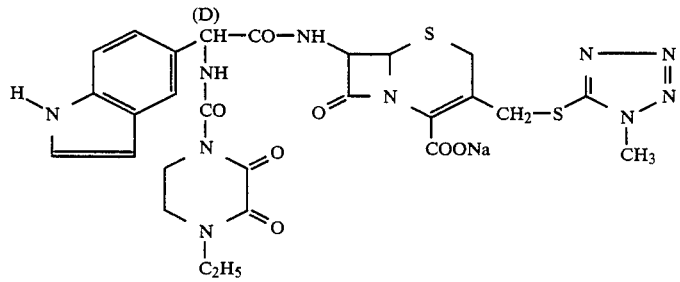

In analogy to Example 9 0.86 g (2.4 mmol) of D-α-[(4-ethyl-2,3-dioxopiperazin-1-yl)carbonylamino]-α-(indol-5-yl) acetic acid was activated with 0.336 ml (2.4 mmol) of triethylamine and 0.230 ml (2.4 mmol) of ethyl chloroformate at −50° C. in dimethylformamide/acetonitrile for 30 mins. and then 0.923 (2.4 mmol) of 7-amino-3-(1-methyl-1H-tetrazol-5-yl-thiomethyl)-3-cephem-4-carboxylic acid-t-butylester, dissolved in 8 ml of tetrahydrofuran, was added to the mixed anhydride at −50° C.

After coupling and isolating the crude cephalosporin derivative the pure end product was finally obtained by adsorber resin chromatography on OC 1062 (see Example 10).

Yield: 0.69 g (39.7 % of theory)

$C_{27}H_{27}N_{10}NaO_7S_2 \cdot 2H_2O$ (726.73) Calculated: C 44.62, H 4.29, N 19.27, S 8.82. Found: C 43.8, H 4.05, N 18.90, S 8.60.

IR spectrum (Nujol): 1780, 1715, 1685–1675 cm$^{-1}$

EXAMPLE 12

D-7[α-(4-ethyl-2,3-dioxo-1-piperazino-carbonylamino)-α-(2-aminobenzoxazol-5-yl)-glycylamido]-3-(1-methyl-1H-tetrazol-5-yl)thiomethyl)-3-cephem-4-carboxylic acid sodium In analogy to Example 9 2.1 g (5.59 mmol) of DL-α-[4-ethyl-2,3-dioxo-piperazin-1-yl)carbonylamino]-α-(2-aminobenzoxazol-5-yl) acetic acid were activated with 0.783 ml (5.59 mmol) of triethylamine and 0.537 ml (5.59 mmol) of ethyl chloroformate at −50° C. in dimethylformamide/acetonitrile for 30 mins. and the mixture was then reacted with 1.84 g (5.59 mmol of 7-amino-3-(1-methyl-1H-tetrazol-5-yl-thiomethyl)-3-cephem-4-carboxylic acid which was brought into solution in 15 ml of water, 15 ml of dimethylformamide and 8 ml of acetonitrile with the addition of 1N sodium hydroxide solution.

After coupling and isolation the crude betaine was chromatographed on an adsorber resin OC 1062 using water/acetone as the mobile solvent system (see Example 8).

Yield: 0.85 g (20.7 % of theory)

$C_{26}H_{26}N_{11}NaO_8S_2 \cdot 2H_2O$ (743.7) Calculated: C 41.99, H 4.07, N 20.72, S 8.62. Found: C 41.51, H 3.55, N 19.90, S 8.40.

IR spectrum (Nujol): 1780, 1720–1650 cm$^{-1}$

EXAMPLE 13

D-7-[α-(4-ethyl-2,3-dioxo-1-piperazine-carbonylamino)-α-(2-amino-1H-benzimidazol-5-yl)-glycylamido]-3-(1-methyl-1H-tetrazol-5-yl-thiomethyl)-3-cephem-4-carboxylic acid sodium

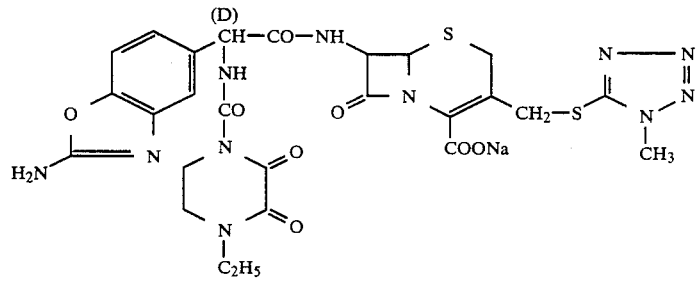

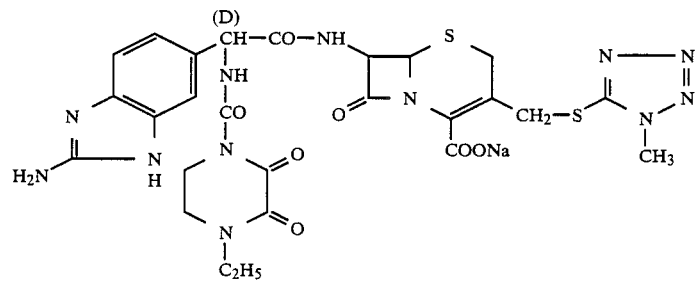

In analogy to Example 9 1.32 g (3.53 mmol) of DL-α-[(4-ethyl-2,3-dioxo-piperazin-1-yl)carbonylamino]-α-(2-amino-1H-benzimidazol-5-yl)-acetic acid were activated with 0.494 ml (3.53 mmol) of triethylamine and 0.339 ml (3.83 mmol) of ethyl chloroformate at −50° C. in dimethylformamide/acetonitrile for 30 mins. and the mixture was then reacted with 1.36 g (3.53 mmol) of 7-amino-3-(1-methyl-1H-tetrazol-5-yl-thiomethyl)-3-cephem-4-carboxylic acid 6-butyl ester dissolved in 20 ml of tetrahydrofuran at −50° C. After coupling and isolation of the crude product in analogy to Example 1 the pure D-isomeric cephalosporin derivative was obtained with the aid of preparative HPLC separation on RP-18.

Yield: 0.62 g (23.7 % of theory)

$C_{26}H_{26}N_{12}NaO_7S_2 2H_2O$ (741.72) Calculated: C 42.10, H 4.08, N 22.66, S 8.65. Found: C 41.54, H 3.75, N 22.40, S 8.41.

IR spectrum (KBr): 1775, 1720–1660 cm$^{-1}$

EXAMPLE 14

7β-(D-α-[(4-ethyl-2,3-dioxopiperazin-1-yl)carbonylamino]-α-(2-methylbenzothiazol-6-yl)glycylamido}-7α-formamido-3-(pyridinomethyl)-3-cephem-4-carboxylic acid

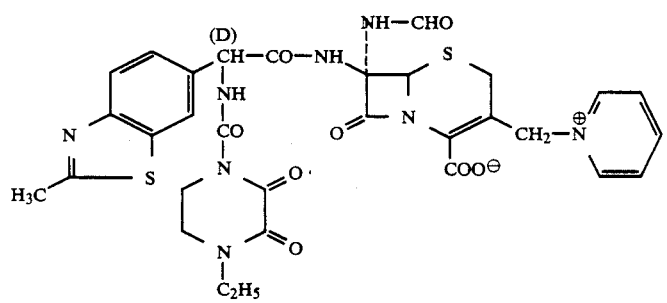

In analogy to Example 9 1.83 g (4.69 mmol) of DL-α-[(4-ethyl-2,3-dioxo-piperazin-1-yl)-carbonylamino]-α-(2-methylbenzothiazol-6-yl) acetic acid were activated with 0.657 ml (4.69 mmol) of triethylamine and 0.450 ml (4.69 mmol) of ethyl chloroformate at −50° C. in dimethylformamide/acetonitrile for 30 mins. and the mixture was then reacted with 1.57 g (4.69 mmol) of 7α-formamido-7β-amino-3-(pyridinomethyl)-3-cephem-4-carboxylic acid which were brought into solution in 10 ml of water, 15 ml of dimethylformamide and 8 ml of acetonitrile with the addition of 1N sodium hydroxide solution. After coupling and isolation the D-isomer was obtained from the crude material in analogy to Example 1 by preparative HPLC separation on RP 18.

Yield: 0.81 g (23.8 % of theory)

$C_{31}H_{30}N_8O_8S_2 H_2O$ (724.78) Calculated: C 50.55, H 4.52, N 15.72, S 9.0. Found: C 49.64, H 4.2, N 15.45, S 8.55.

IR spectrum (KBr): 1770, 1730, 1660–1630 cm$^{-1}$.

We claim:

1. A phenyl-β-lactam of the formula

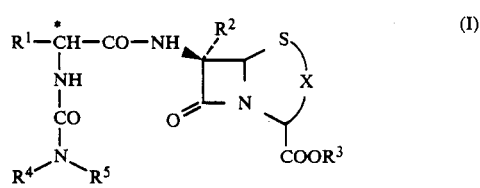

in which

R$^1$—stands for a hetero-O-containing or a hetero-S-containing radical of the formula

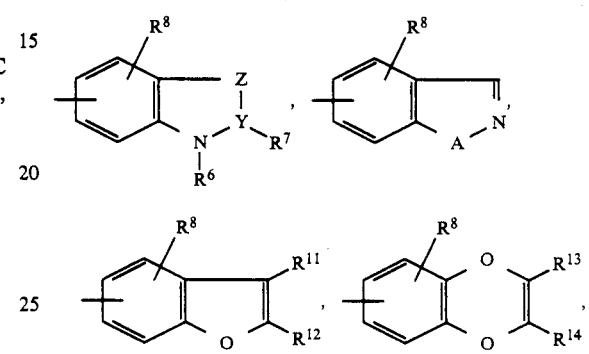

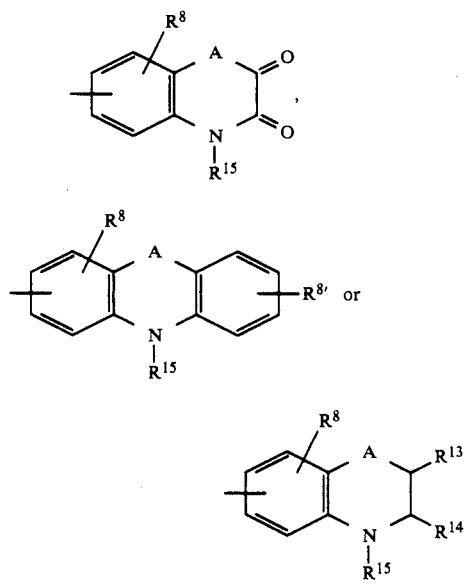

wherein

Y—stands for N or CR$^{16}$, or the grouping

Y—R$^7$—stands for >=O or >=N—R$^7$

Z—stands for O, S or —NR$^{17}$,

A—stands for O or S

R⁶—stands for hydrogen or
  stands for hydroxyl or amino, or
  stands for straight-chain, branched or cyclic alkyl or alkenyl having up to 10 carbon atoms which is optionally substituted by halogen, amino, hydroxyl, cyano or $C_6$-$C_{10}$-aryl, or
  stands for $C_6$-$C_{10}$-aryl, R⁷—stands for hydrogen, or
  stands for optionally substituted $C_6$-$C_{10}$-aryl, or
  stands for straight-chain, branched or cyclic alkyl or alkenyl having up to 10 carbon atoms which is optionally substituted by halogen, hydroxyl, alkoxy or alkoxycarbonyl each having up to 6 carbon atoms, cyano, carboxyl, $C_6$-$C_{10}$-aryl, sulpho or by an amino group, or R⁶ and R⁷ together complete a double bond, R⁸ and R⁸, are identical or different and
  stand for hydrogen, or
  stand for straight-chain, branched or cyclic alkyl, alkoxy or alkylthio each having up to 8 carbon atoms, or
  stand for trifluoromethyl or trifluoromethoxy, or
  stand for hydroxyl, mercapto, nitro, cyano or halogen, or
  stand for an amino group, R¹¹ and R¹² are identical or different and
  stand for hydrogen, or
  stand for $C_6$-$C_{10}$-aryl, or
  stand for heterocyclyl, or
  stand for hydroxyl, or
  stand for an amino group, or
  stand for straight-chain, branched or cyclic alkoxy having up to 8 carbon atoms, or
  stand for acyl or acyloxy each having up to 7 carbon atoms, or
  stand for alkoxycarbonyl having up to 8 carbon atoms, or
  stand for straight-chain, branched or cyclic alkyl having up to 12 carbon atoms, or R¹¹ and R¹² together stand for the grouping of the formula

R¹³ and R¹⁴ are identical or different and
  stand for hydrogen, or
  stand for straight-chain, branched or cyclic alkyl having up to 12 carbon atoms, or
  stand for $C_6$-$C_{10}$-aryl, or
  stand for alkoxycarbonyl having up to 8 carbon atoms, R¹⁵ stands for hydrogen, or
  stands for $C_6$-$C_{10}$-aryl, or
  stands for straight-chain, branched or cyclic alkyl having up to 8 carbon atoms, R¹⁶ has any of the meanings of R⁷ and in addition
  stands for halogen, or
  stands for straight-chain, branched or cyclic alkoxy or alkylthio each having up to 8 carbon atoms, or
  stands for an amino group, or
  stands for straight-chain, branched or cyclic alkylsulphonyl having up to 8 carbon atoms, or
  stands for phosphono, sulpho or sulphamoyl, or
  stands for mercapto, hydroxyl, phenylthio or phenoxy, or
  stands for guanidino, amidino, hydrazino or hydroxylamino, or
  stands for optionally substituted heterocyclyl, or
  stands for pyrrolyl, pyrrolidinyl, pyrazolyl, imidazolyl, pyridinyl, quinolyl, isoquinolyl, furyl, thienyl, morpholinyl, piperidinyl, piperazinyl, or pyrimidyl, each of which can be substituted by fluorine, chlorine, methyl, nitro, cyano, hydroxyl, trifluoromethyl, methoxy or amino, or
  stands for pyridylthio or pyridyloxy, R¹⁷ has any of the meanings of R¹⁶, but does not complete a double bond with R⁷, or R¹⁶ and R¹⁷ together stand for a $C_2$-$C_4$-methylene chain which is optionally interrupted by oxygen or sulphur, and R¹⁸ has any of the meanings of R¹⁵ and can be identical or different thereto, R²—stands for hydrogen, or
  stands for straight-chain, branched or cyclic alkoxy or alkylthio each having up to 5 carbon atoms, or
  stands for an amino group, R³—stands for hydrogen, or
  stands for a carboxyl protective group, or
  stands for an ester radical which is cleavable in vivo, X—stands for a group of the formula

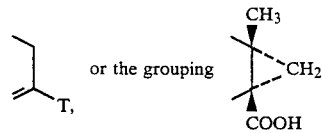

wherein
T—denotes hydrogen or halogen, or
  denotes straight-chain, branched or cyclic alkoxy or alkylthio each having up to 6 carbon atoms, or
  denotes straight-chain, branched or cyclic alkyl, alkenyl or alkinyl each having up to 7 carbon atoms, which can be optionally substituted by halogen, hydroxyl, alkoxy or alkylthio having up to 5 carbon atoms, aminocarbonyloxy, acyloxy having up to 10 carbon atoms, or by a pyridinium radical which can be monosubstituted or polysubstituted, or by a radical of the formula

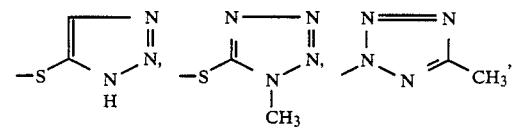

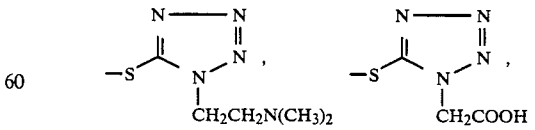

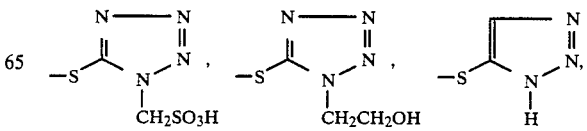

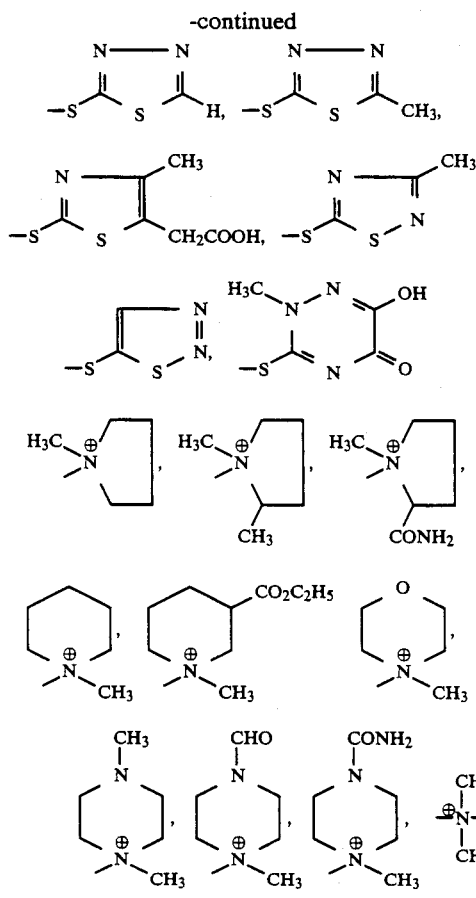

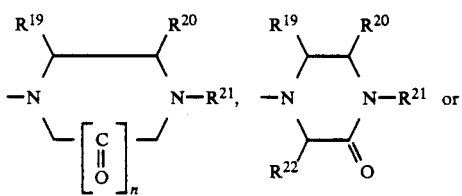

R⁴—stands for hydrogen, or
stands for straight-chain, branched or cyclic alkyl having up to 8 carbon atoms, or
stands for $C_6$–$C_{10}$-aryl, R⁵—stands for hydrogen, or
stands for straight-chain, branched or cyclic alkyl having up to 8 carbon atoms, or
stands for a 5- to 6-membered heterocyclic radical which can contain one to two nitrogen atoms, an oxygen and/or a sulphur atom as hetero atoms and which can be substituted by identical or different, straight-chain, branched or cyclic alkyl, alkenyl or alkinyl each having up to 6 carbon atoms, cycloalkyl having 3 to 7 carbon atoms, alkoxy, alkenyloxy, alkylthio, alkenylthio, alkylsulphonyl or alkenylsulphonyl each having up to 6 carbon atoms, by aryl, aryloxy, arylthio or arylsulphonyl each having 6 to 10 carbon atoms, by an amino group, by oxo, hydroxyl, mercapto, cyano, nitro, by alkylimino having up to 6 carbon atoms or arylimino having 6 to 10 carbon atoms, or R⁴ and R⁵, together with the nitrogen atom, form a ring of the formula

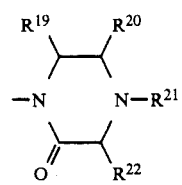

wherein
R¹⁹ and R²⁰ are identical or different and denote hydrogen, straight-chain, branched or cyclic alkyl or alkoxy each having up to 4 carbon atoms, hydroxyl, amino, $C_6$–$C_{10}$-aryl or halogen, or
denote the grouping of the formula

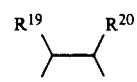

or a grouping of the formula

R²¹—denotes hydrogen, or
denotes straight-chain or branched alkyl or alkenyl each having up to 10 carbon atoms, or
denotes cycloalkyl having 3 to 7 carbon atoms, where one or two $CH_2$ groups can be replaced by CO, CS, $CO_2$, O or S in the said radicals, or
denotes $C_6$–$C_{10}$-aryl or $C_7$–$C_{14}$-aralkyl, or
denotes a heterocyclic radical selected from the group consisting of thienyl, furyl, pyridyl, pyrimidyl, oxazolyl, thiazolyl, oxadiazolyl, thiadiazolyl, benzoxazolyl, benzothiazolyl, benzoxadiazolyl, benzothiadiazolyl, quinolyl, isoquinolyl, and indolyl, where the said heterocycles may be monosubstituted, disubstituted or trisubstituted by identical or different, straight-chain, branched or cyclic alkyl, alkoxy, alkylthio or alkylsulphonyl each having up to 8 carbon atoms, by trifluoromethyl, trifluoromethoxy, halogen, nitro, cyano, $C_6$–$C_{10}$-aryl or $C_7$–$C_{14}$-aralkyl, or R²¹—denotes a group of the formula

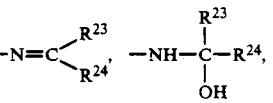

$-SO_2-R^{25}$, $-COR^{25}$ or $-CSR^{25}$,

R²²—denotes hydrogen or straight-chain, branched or cyclic alkyl having up to 6 carbon atoms, R²³ and R²⁴ are identical or different and denote hydrogen, cyano, carboxyl, alkoxycarbonyl having up to 6 carbon atoms, or
denote straight-chain or branched alkyl or alkenyl each having up to 8 carbon atoms, or
denote cycloalkyl having 3 to 7 carbon atoms, or
denote $C_6$–$C_{10}$-aryl or $C_7$–$C_{14}$-aralkyl, or denote a heterocycle selected from the group consisting of furyl, thienyl, pyridyl, pyrimidyl, oxazolyl, thiazolyl, oxadiazolyl, thiadiazolyl, benzoxazolyl and benzothiazolyl, where the said heterocycles may be monosubstituted, disubstituted or trisubstituted by identical or different, straight-chain, branched or cyclic alkyl, alkoxy or alkylthio each having up to 6 carbon atoms, by halogen, nitro, cyano, trifluoromethyl or trifluoromethoxy, or $R^{23}$ and $R^{24}$, together with the carbon atom, form a 3- to 7-membered heterocyclic ring which can contain up to two nitrogens, an oxygen and/or a sulphur atom as heteroatoms, which can be saturated or unsaturated and fused to benzene, and which can be monosubstituted, disubstituted or trisubstituted by straight-chain or branched alkyl or alkoxy each having up to 8 carbon atoms, by cycloalkyl having 3 to 7 carbon atoms, by halogen, cyano, nitro, trifluoromethyl or trifluoromethoxy, and $R^{25}$—denotes hydroxyl, straight-chain or branched alkyl, alkenyl or alkoxy each having up to 8 carbon atoms, or denotes cycloalkyl having 3 to 7 carbon atoms, or denotes $C_6$–$C_{10}$-aryl or $C_7$–$C_{14}$-aralkyl, or denotes an amino group, or denotes a heterocyclic ring selected from the group consisting of furyl, thienyl, pyridyl, pyrimidyl, thiazolyl, oxazolyl, thiadiazolyl and oxadiazolyl, where the said heterocyclic radicals can be monosubstituted, disubstituted or trisubstituted by identical or different, straight-chain or branched alkyl, alkoxy or alkylthio each having up to 6 carbon atoms, by halogen, nitro, cyano, trifluoromethyl or trifluoromethoxy, or a pharmaceutically acceptable salt thereof.

2. A compound or salt according to claim 1, in which
$R^1$—stands for a group of the formula

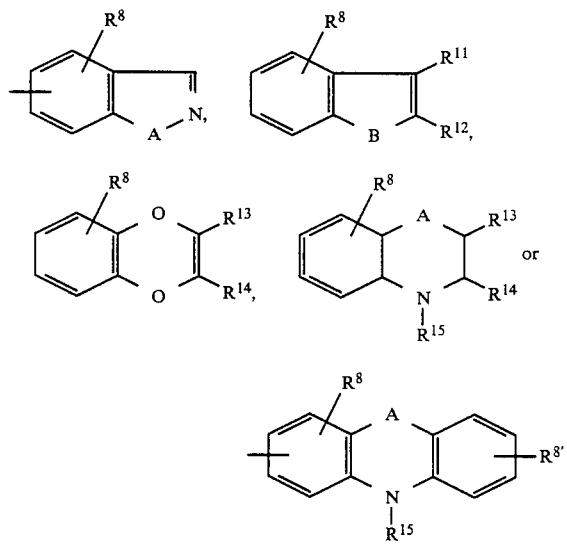

wherein
$R^6$–stands for hydrogen, or
stands for hydroxyl or amino, or
stands for straight-chain, branched or cyclic alkyl or alkenyl each having up to 8 carbon atoms, which are optionally substituted by one or more fluorine, chlorine, bromine, amino, hydroxyl or phenyl substitutents, or
stands for phenyl, $R^7$—stands for hydrogen, or
stands for phenyl, or
stands for straight-chain, branched or cyclic alkyl or alkenyl each having up to 8 carbon atoms, which is optionally substituted by one or more fluorine, chlorine, bromine, alkoxy having up to 4 carbon atoms, hydroxyl, carboxyl, phenyl, sulpho or an amino group, $R^8$ and $R^{8'}$ are identical or different and
stand for hydrogen, or
stand for straight-chain or branched alkyl, alkoxy or alkylthio each having up to 6 carbon atoms, or
stand for trifluoromethyl or trifluoromethoxy, or
stand for hydroxyl, mercapto, nitro, cyano, fluorine, chlorine or bromine, or
stand for an amino group, $R^{11}$ and $R^{12}$ are identical or different and
stand for hydrogen, or
stand for phenyl which is optionally monosubstituted or disubstituted identically or differently by fluorine, chlorine, bromine, alkyl, alkoxy or alkylthio each having up to 4 carbon atoms, halogenoalkyl, halogenoalkoxy or halogenoalkylthio each having up 3 carbon atoms and having one to three halogen atoms, by nitro, cyano, dimethylamino or amino, or
stand for hydroxyl, or
stand for pyridyl, thienyl, furyl or pyrimidyl, or
stand for an amino group having the abovementioned meaning, or
stand for straight-chain, branched or cyclic alkoxy having up to 6 carbon atoms, or
stand for benzoyloxy, alkanoyloxy having up to 4 carbon atoms, or
stand for benzoyl or acetyl, or
stand for alkoxycarbonyl having up to 6 carbon atoms, or
stand for straight-chain, branched or cyclic alkyl having up to 8 carbon atoms and optionally substituted one to three times by fluorine, chlorine, bromine, alkoxy or alkylthio each having up to 4 carbon atoms, halogenalkoxy or halogenoalkylthio each having up to 4 carbon atoms and having one to three halogen atoms, by nitro, cyano, an amino group having the abovementioned meaning, phenyl, sulpho, sulphamoyl, alkylsulphonyl having up to 2 carbon atoms, hydroxyl, mercapto, benzyloxy, alkanoloxy having up to 4 carbon atoms, carbamoyloxy, alkoxycarbonyl having up to 4 carbon atoms, phenyloxy, phenylthio, benzyloxy or benzylthio, or $R^{11}$ and $R^{12}$ together stand for a grouping of the formula

$R^{13}$ and $R^{14}$ are identical or different and
stand for hydrogen, or
stand for straight-chain, branched or cyclic alkyl having up to 8 carbon atoms, which is optionally substituted once or more by fluorine, chlorine, bromine, alkoxy or alkylthio each having up to 4 carbon atoms, halogenoalkoxy or halogenoalkylthio each having up to 4 carbon atoms and having one to three halogen atoms, by nitro, cyano, an amino group having the abovementioned meaning, phenyl, sulpho, sulphamoyl, alkylsulphonyl having up to 2 carbon atoms, hydroxyl, mercapto, benzoyloxy, alkanoloxy having up to 4 carbon atoms, carbamoyloxy or alkoxycarbonyl having up to 4 carbon atoms, or stand for phenyl, which is optionally monosubstituted or disubstituted identically or differently by fluorine, chlorine, bromine, alkyl, alkoxy or alkylthio each having up to 4 carbon atoms, halogenoalkyl, halogenoalkoxy or halogenoalkylthio each having up 3 carbon atoms and one to three halogen atoms, by nitro, cyano, amino or dimethylamino, or stand for alkoxycarbonyl having up to 6 carbon atoms, A—stands for O, S or —NR$^{18}$, B—stands for O or —NR$^{15}$, R$^{15}$—stands for hydrogen, or
stands for phenyl, or
stands for straight-chain, branched or cyclic alkyl having up to 6 carbon atoms, R$^{16}$ has the same meaning as R$^7$ and in addition
stands for fluorine, chlorine, bromine, or
stands for alkoxy, alkylthio or alkylsulphonyl each having up to 6 carbon atoms, or
stands for an amino group, or
stands for phosphino, sulpho, sulphamoyl, hydroxyl, mercapto, phenylthio or phenoxy, or
stands for guanidino, hydrazino, or hydroxylamino, or
stands for pyrrolyl, pyrrolidinyl, pyrazolyl, imidazolyl, pyridyl, quinolyl, isoquinolyl, furyl, thienyl, morpholinyl, piperidinyl, piperazinyl, or pyrimidyl, each of which can be substituted by fluorine, chlorine, methyl, nitro, cyano, hydroxyl, trifluoromethyl, methoxy or amino, or
stands for pyridylthio or pyridyloxy, R$^{17}$ has the same meaning as R$^{16}$, but does not complete a double bond with R$^7$, or R$^{16}$ and R$^{17}$ together stand for a C$_2$-C$_4$-methylene chain which is optionallly interrupted by sulphur, and R$^{18}$ has the same meaning as R$^{15}$ and can be identical or different to this, R$^2$—stands for hydrogen, or
stands for methoxy or methylthio, or
stands for amino, alkylamino or dialkylamino each having up to 3 carbon atoms per alkyl group, phenylamino, benzylamino or acetamido, or
stands for formamidino, R$^3$—stands for hydrogen, or
stands for methyl, ethyl, tert.-butyl, 2-chloroethyl, 2,2,2-trichloroethyl, cyanoethyl, diphenylmethyl, triphenylmethyl, acetoxymethyl, allyl, benzyl, 4-methoxybenzyl, 2,4-dimethoxybenzyl, 1-phenoxyethyl, 2-methyl-2-propenyl, 4-nitrobenzyl, 2-nitrobenzyl, trimethylsilylethyl or tert.-butyldimethylsilylethyl, or
stands for a radical of the formula

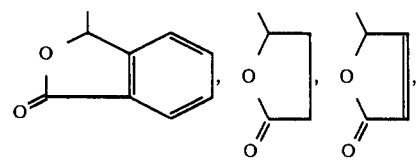

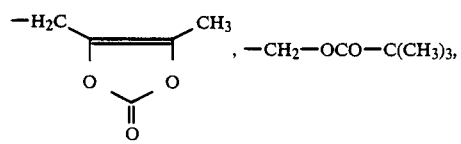

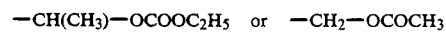

T—denotes hydrogen or fluorine, chlorine or bromine, or
denotes straight-chain, branched or cyclic alkoxy or alkylthio each having up to 3 carbon atoms, or
denotes straight-chain or branched alkyl or alkenyl each having up to 5 carbon atoms, which is optionally substituted once or more by fluorine, chlorine, bromine, alkoxy or alkylthio each having up to 3 carbon atoms, aminocarbonyloxy, acetyloxy, benzoyloxy or by a radical of the formula

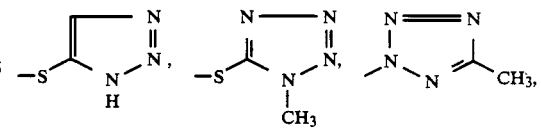

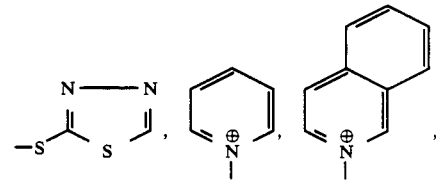

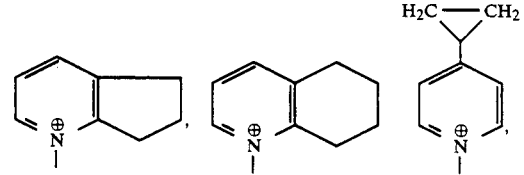

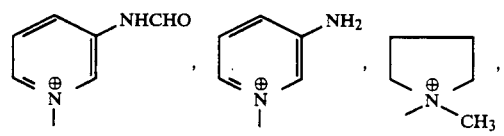

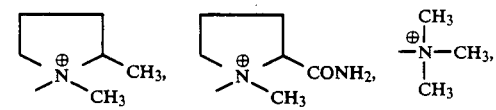

-continued

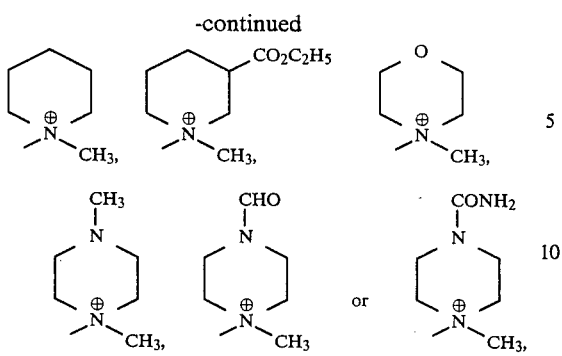

R⁴—stands for hydrogen, or
  stands for straight-chain or branched alkyl having up to 4 carbon atoms, or
  stands for phenyl,
R⁵—stands for hydrogen, or
  stands for straight-chain or branched alkyl having up to 4 carbon atoms, or
  stands for a 5- to 6-membered heterocyclic ring which can contain a nitrogen, oxygen or sulphur atom as heteroatoms and which can be monosubstituted or disubstituted by identical or different alkyl or alkenyl having up to 4 carbon atoms, by cyclopropyl, cyclopentyl or cyclohexyl, by alkoxy, alkenyloxy, alkylsulphonyl or alkenylsulphonyl each having up to 4 carbon atoms, phenyl, phenyloxy, phenylsulphonyl or by amino, alkylamino or dialkylamino each having up to 3 carbon atoms per alkyl group, by oxo, alkylimino having up to 3 carbon atoms or phenylimino, or
R⁴ and R⁵, together with the nitrogen atom, form a ring of the formula

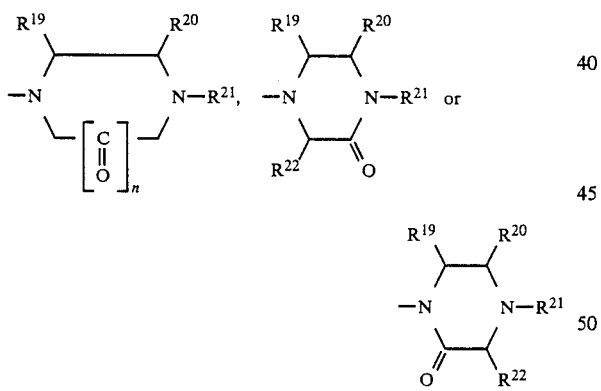

wherein
R¹⁹ and R²⁰ are identical or different and denote hydrogen, methyl, ethyl, methoxy, phenyl, fluorine or chlorine,
R²¹ denotes hydrogen, or
  denotes straight-chain or branched alkyl having up to 6 carbon atoms, or
  denotes straight-chain or branched alkenyl having up to 6 carbon atoms, or
  denotes cycloalkyl having 3 to 6 carbon atoms, where a methylene group in the said radicals can be replaced by CO, SO₂, O or S, or
  denotes phenyl or benzyl, or
  denotes a heterocyclic radical from the series comprising thienyl, furyl, pyridyl, pyrimidyl, oxazolyl, thiazolyl, oxadiazolyl, thiadiazolyl, benzoxazolyl, benzothiazolyl, benzodiazoyl, or benzothiadiazolyl, where the said heterocyclic radicals can be monosubstituted or disubstituted by identical or different, straight-chain or branched alkyl, alkoxy, alkylthio or alkylsulphonyl each having up to 6 carbon atoms, by trifluoromethyl, trifluoromethoxy, fluorine, chlorine, bromine, cyano, phenyl or benzyl, or
a group of the formula

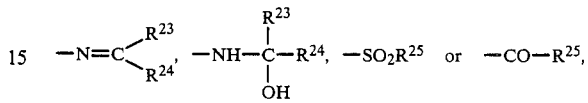

wherein
R²²—denotes hydrogen, or straight-chain or branched alkyl having up to 4 carbon atoms,
R²³ and R²⁴ are identical or different and denote hydrogen, or
  denote alkoxycarbonyl having up to 4 carbon atoms, or
  denote straight-chain or branched alkyl or alkenyl having up to 6 carbon atoms, or
  denote cycloalkyl having 3 to 6 carbon atoms, or
  denote phenyl or benzyl, or
  denote a heterocyclic radical selected from the group consisting of furyl, pyridyl, pyrimidyl, thienyl, oxazolyl and thiazolyl, which can optionally be monosubstituted or disubstituted by identical or different alkyl or alkoxy each having up to 4 carbon atoms, fluorine, chlorine, bromine, nitro, cyano, trifluoromethyl or trifluoromethoxy, or
R²³ and R²⁴, together with the carbon atom, form a 5- or 6-membered heterocyclic ring which can contain up to two nitrogen atoms, one oxygen atom and/or one sulphur atom as heteroatoms, which can be saturated or unsaturated and which can be monosubstituted or disubstituted by identical or different alkyl or alkoxy having up to 6 carbon atoms, cyclopropyl, cyclopentyl or cyclohexyl, or by fluorine, chlorine, bromine, cyano, nitro, trifluoromethyl, or trifluoromethoxy,
R²⁵ stands for hydroxyl or alkoxy having up to 4 carbon atoms, or
  stands for alkyl or alkenyl having up to 6 carbon atoms, or
  stands for cycloalkyl having 3 to 6 carbon atoms, or
  stands for phenyl or benzyl, or
  stands for amino, or
  stands for a heterocyclic radical selected from the group consisting of furyl, pyridyl, pyrimidyl, thiazolyl, oxazolyl, thiadiazolyl and oxadiazolyl, where the said heterocycles can be monosubstituted or disubstituted by identical or different alkyl or alkoxy having up to 4 carbon atoms, fluorine, chlorine, bromine, nitro, cyano, trifluoromethyl or trifluoromethoxy.
3. A compound or salt according to claim 1 in which
R¹—stands for a group of the formula

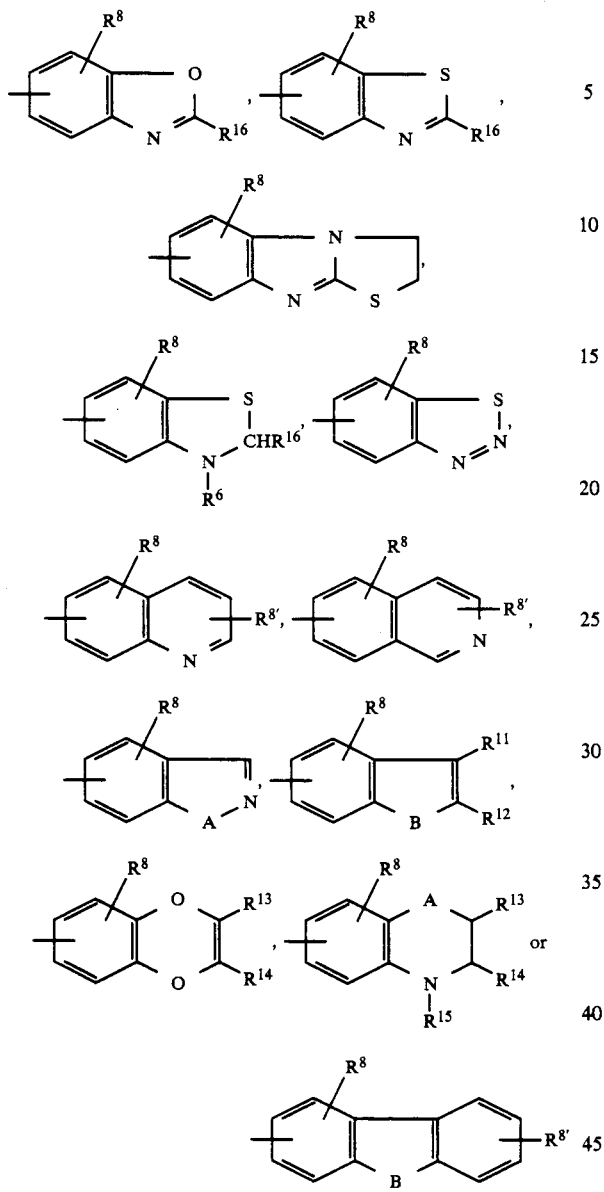

wherein

R⁶—stands for hydrogen, or
stands for straight-chain, branched or cyclic alkyl or alkenyl having up to 6 carbon atoms, which is optionally substituted by fluorine, amino, hydroxyl or phenyl, or
stands for phenyl, R⁸ and R⁸' are identical or different and
stand for hydrogen, or
stand for straight-chain or branched alkyl, alkoxy or alkylthio each having up to 4 carbon atoms, or
stand for trifluoromethyl or trifluoromethoxy, or
stand for hydroxyl, nitro, cyano, fluorine or chlorine, or
stand for amino, methylamino, dimethylamino, phenylamino or acetamido, R¹¹ and R¹² are identical or different and
stand for hydrogen, or
stand for phenyl which is optionally substituted by fluorine, chlorine, alkyl having up to 4 carbon atoms, methoxy, methylthio, trifluoromethyl, trifluoromethoxy, trifluoromethylthio, nitro, cyano, amino or dimethylamino, or
stand for pyridyl, thienyl, furyl, pyrimidyl or hydroxyl, or
stand for amino, methylamino, dimethylamino, phenylamino or acetamido, or
stand for alkoxy having up to 4 carbon atoms, or
stand for benzoyloxy or acetoxy, or
stand for benzoyl or acetyl, or
stand for alkoxycarbonyl having up to 4 carbon atoms, or
stand for straight-chain, branched or cyclic alkyl or alkenyl having up to 6 carbon atoms, which is optionally substituted by fluorine, chlorine, methoxy, methylthio, trifluoromethoxy, cyano, phenyloxy or benzyloxy, R¹³ and R¹⁴ are identical or different and
stand for hydrogen, or
stand for straight-chain, branched or cyclic alkyl or alkenyl having up to 6 carbon atoms, which is optionally substituted by fluorine, chlorine, methoxy, methylthio, trifluoromethoxy or cyano, or
stand for phenyl which is optionally substituted by fluorine, chlorine, alkyl having up to 4 carbon atoms, methoxy, methylthio, trifluoromethyl, trifluoromethoxy, trifluoromethylthio, nitro, cyano, amino or dimethylamino, or
stand for alkoxycarbonyl having up to 4 carbon atoms, A—stands for O, S or —NR¹⁸,
B—stands for O or —NR¹⁵,
R¹⁵—stands for hydrogen, or
stands for phenyl, or
stands for straight-chain or branched alkyl having up to 4 carbon atoms, R¹⁶ stands for hydrogen, or
stands for straight-chain or branched alkyl or alkenyl each having up to 4 carbon atoms, which is optionally substituted by fluorine, chlorine, alkoxy having up to 4 carbon atoms, hydroxyl, carbonyl, phenyl, sulpho, amino, alkylamino or dialkylamino each having up to 3 carbon atoms per alkyl group, phenylamino, benzylamino or by acetamido, or
stands for fluorine, chlorine or bromine, or
stands for alkoxy or alkylthio each having up to 4 carbon atoms, or
stands for phenyl, or
stands for amino, alkylamino or dialkylamino each having up to 3 carbon atoms per alkyl group, phenylamino, benzylamino or acetamido, or
stands for alkylsulphonyl having up to 4 carbon atoms, or
stands for sulpho or sulphamoyl, or
stands for hydroxyl, mercapto, phenyloxy or phenylthio, or
stands for guanidino, hydrazino or hydroxylamino, or
stands for pyrrolyl, pyrrolidinyl, pyrazolyl, imidazolyl, pyridinyl, quinolyl, isoquinolyl, furyl, thienyl, morpholinyl, piperidinyl, piperazinyl, or pyrimidyl, each of which can be substituted by fluorine, chlorine, methyl, nitro, cyano, hydroxyl, trifluoromethyl, methoxy or amino, or
stands for pyridylthio or pyridyloxy $R^{17}$—has the same meaning as $R^{16}$ and can be identical or different to $R^{16}$, and $R^{18}$—has the same meaning as $R^{15}$ and is identical or different to $R^{15}$, $R^2$—stands for hydrogen, or
stands for methoxy or methylthio, or
stands for amino, methylamino, dimethylamino, phenylamino, benzylamino, or acetamido, or
stands for formamidino, $R^3$—stands for hydrogen, or
stands for methyl, ethyl, tert.-butyl, 2,2,2-trichloroethyl, allyl, acetoxymethyl, 4-nitrobenzyl, 2-nitrobenzyl, 4-methoxybenzyl, benzyl or trimethylsilylethyl, or
stands for a radical of the formula

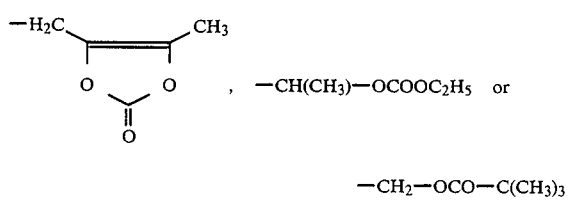

$-CH_2-OCO-C(CH_3)_3$

T—denotes hydrogen, chlorine, fluorine, methyl, methoxy, methylthio, trifluoromethyl, methoxymethyl, vinyl, carbamoyloxymethyl or acetoxymethyl, or
denotes a group of the formula $-CH=CH-CH_3$, $-CH=CH-C_2H_5$, $-CH=CH-CH_2Cl$, $-CH=CH-CH_2OCH_3$, $-CH=CH-CH_2-S-$

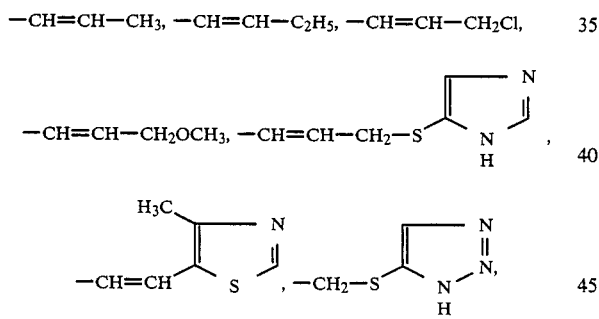

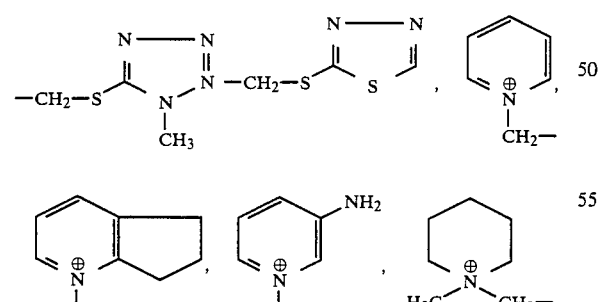

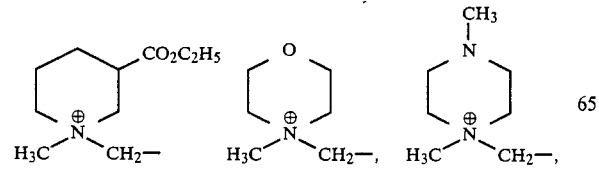

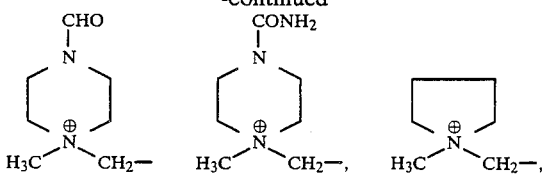

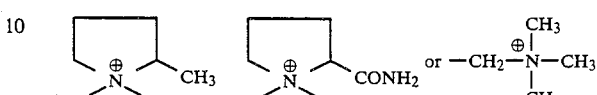

and $R^4$ and $R^5$, together with the nitrogen atom, form a ring of the formula

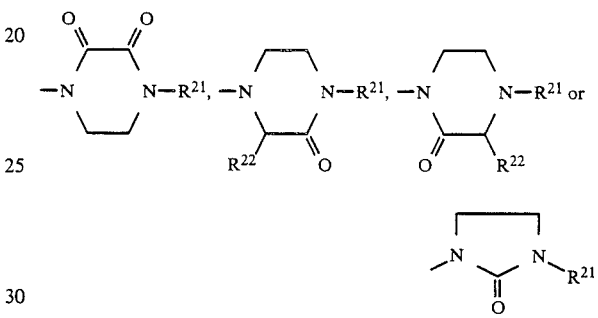

wherein $R^{21}$ denotes hydrogen or alkyl having up to 4 carbon atoms, or
denotes cyclopropyl, cyclopentyl or cyclohexyl, or
denotes phenyl, or
denotes a heterocyclic radical selected from the group consisting of furyl, pyridyl, pyrimidyl, thiazolyl, benzothiazolyl, thiadiazolyl and benzothiadiazolyl, where the said heterocycles can be substituted by straight-chain or branched alkyl, alkenyl, alkoxy, alkylthio or alkylsulphonyl each having up to 4 carbon atoms, by trifluoromethyl, fluorine or chlorine, or
denotes a group of the formula

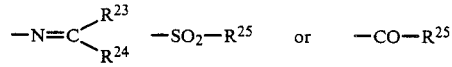

$R^{22}$ denotes hydrogen or methyl, $R^{23}$ and $R^{24}$ are identical or different and denote hydrogen, or
denote straight-chain or branched alkyl or alkenyl each having up to 4 carbon atoms, or
denote cyclopropyl, cyclopentyl, or cyclohexyl, or
denote phenyl or benzyl, or
denote a heterocyclic ring selected from the group consisting of furyl, pyridyl and pyrimidyl, or $R^{23}$ and $R^{24}$, together with the carbon atom, form a ring selected from the group consisting of furyl, pyridyl, pyrimidyl, oxacolyl, thiazolyl, oxadiazolyl and thiadiazolyl, and $R^{25}$—denotes methoxy or ethoxy, or
denotes straight-chain or branched alkyl or alkenyl each having up to 4 carbon atoms, or denotes cyclopropyl, cyclopentyl or cyclohexyl, or denotes phenyl or benzyl, or denotes amino, alkylamino or dialkylamino each having up to 3 carbon atoms per alkyl group, or denotes a heterocyclic ring selected from the group consisting of furyl, pyridyl, pyrimidyl and quinolyl, where the heterocyclic rings can be substituted by methyl, ethyl, propyl, isopropyl, methoxy, fluorine, chlorine or trifluoromethyl.

4. A compound according to claim 1, wherein such compound is D-7-[α-(4-ethyl-2,3-dioxo-1-piperazinocarbonylamino)-α-(2-aminobenzothiazol-6-yl)glycylamido]-3-(1-methyl-1H-tetrazol-5-yl-thimethyl)-3-cephem-4-carboxylic acid of the formula

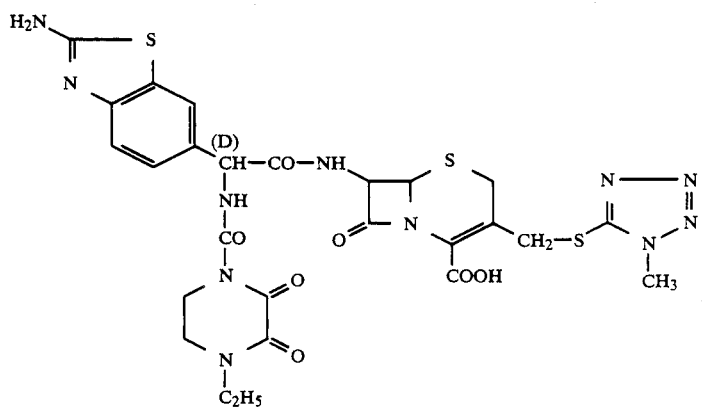

or a pharmacologically acceptable salt thereof.

5. A compound according to claim 1, wherein such compound is D-7-[α-(4-ethyl-2,3-dioxo-1-piperazinocarbonylamino)-α-(2-aminobenzothiazol-6-yl)glycylamido]-3-acetoxy-methyl-3-cephem-4-carboxylic acid of the formula

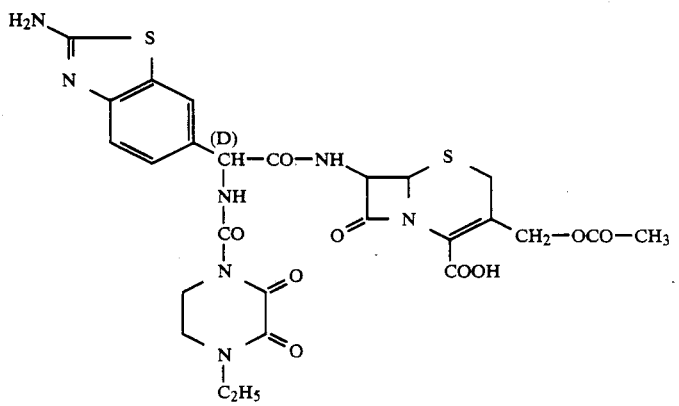

or a pharmacologically acceptable salt thereof.

6. A compound according to claim 1, wherein such compound is 7β{D-α-[(4-ethyl-2,3-dioxopiperazin-1-yl)carbonylamino]-α(2-amino-1H-benzimidazol-5-ylglycylamido}-7β-formamido-3-(pyridinomethyl)-3 cephem-4-carboxylic acid of the formula

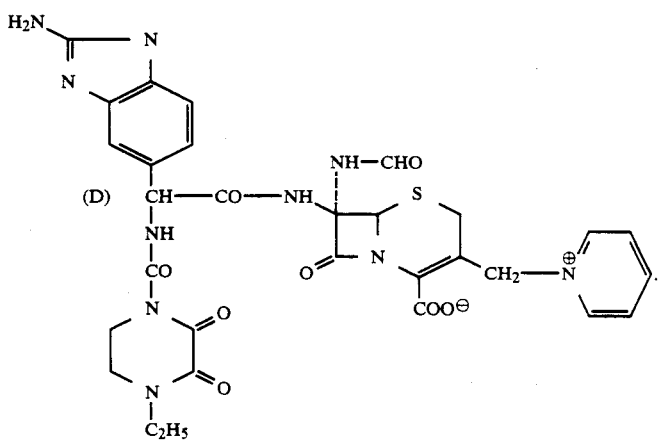

7. An antibiotically active composition comprising an antibacterially effective amount of a phenylglycine-β-lactam according to claim 1 and a pharmaceutically acceptable diluent.

8. A unit does of a composition according to claim 7 in the form of a tablet, capsule or ampoule.

9. A method combating bacteria in a patient in need thereof which comprises administering to such patient an antibacterially effective amount of a phenylglycine-β-lactam according to claim 7.

10. The method according to claim 9, wherein such compound is

D-7-[α-(4-ethyl-2,3-dioxo-1-piperazino-carbonylamino)-α(2-aminobenzothiazol-6-yl)glycylamido]-3-(1-methyl-1H-tetrazol-5-yl-thiomethyl)-3-cephem-4-carboxylic acid, D-7-[α-(4-ethyl-2,3-dioxo-1-piperazinocarbonylamino)-(2-aminobenzothiazol-6-yl)glycylamido]-3-acetoxymethyl-3-cephem-4-carboxyl acid, or 7β-{D-α-[(4-ethyl-2,3-dioxopiperazin-1-yl)carbonylamino]-α(2-amino-1H-benzimidazol-5-ylglycylamido}-7α-formamido-3-(pyridiniomethyl)3-cephem-4-carboxylic acid.

* * * * *

UNITED STATES PATENT AND TRADEMARK OFFICE
CERTIFICATE OF CORRECTION

PATENT NO. : 4,973,685

DATED : November 27, 1990

INVENTOR(S) : Schmidt et al.

It is certified that error appears in the above-identified patent and that said Letters Patent is hereby corrected as shown below:

Col. 107, line 18   After 1st " and " delete " $R^8$ " and substitute -- $R^{8'}$ --

Col. 112, line 12   After 1st " and " delete " $R^8$ " and substitute -- $R^{8'}$ --

Col. 124, line 5    After " ) " insert -- $\alpha$ --

Signed and Sealed this

Tenth Day of November, 1992

Attest:

DOUGLAS B. COMER

*Attesting Officer*    *Acting Commissioner of Patents and Trademarks*